(12) United States Patent
Mavani et al.

(10) Patent No.: US 8,206,416 B2
(45) Date of Patent: Jun. 26, 2012

(54) INFLATABLE DEVICE FOR ENTERIC FISTULA TREATMENT

(75) Inventors: Akshay Mavani, Los Altos, CA (US); Kenton Fong, Mountain View, CA (US); Leif Erik Bansner, Berkeley, CA (US); Nathan Christopher Maier, Hayward, CA (US); Dean Hu, Hayward, CA (US); Moshe Pinto, Mountain View, CA (US); Harold Francis Carrison, Pleasanton, CA (US); Eliot Kim, San Carlos, CA (US)

(73) Assignee: CuraSeal Inc., Santa Clara, CA (US)

( * ) Notice: Subject to any disclaimer, the term of this patent is extended or adjusted under 35 U.S.C. 154(b) by 280 days.

(21) Appl. No.: 12/568,610

(22) Filed: Sep. 28, 2009

(65) Prior Publication Data

US 2010/0249827 A1    Sep. 30, 2010

Related U.S. Application Data

(63) Continuation of application No. 12/554,758, filed on Sep. 4, 2009, now Pat. No. 8,177,809.

(60) Provisional application No. 61/094,378, filed on Sep. 4, 2008.

(51) Int. Cl.
*A61B 17/08* (2006.01)
(52) U.S. Cl. .......................... 606/213; 606/151; 606/157
(58) Field of Classification Search .................. 606/151, 606/153, 157, 213, 215, 142
See application file for complete search history.

(56) References Cited

U.S. PATENT DOCUMENTS

| | | | |
|---|---|---|---|
| 2,324,520 | A | 7/1943 | Lamson |
| 2,510,766 | A | 6/1950 | Surface |
| 2,564,399 | A | 8/1951 | Franken |
| 2,934,068 | A | 4/1960 | Graham, Jr. at al. |
| 3,447,533 | A | 6/1969 | Spicer |
| 3,882,858 | A | 5/1975 | Klemm |
| 4,057,535 | A | 11/1977 | Lipatova et al. |
| 4,241,735 | A | 12/1980 | Chernov |
| 4,365,621 | A | 12/1982 | Brundin |

(Continued)

FOREIGN PATENT DOCUMENTS

WO    WO-89/11301 A1    11/1989

(Continued)

OTHER PUBLICATIONS

International Search Report mailed on Oct. 21, 2009, for PCT Patent Application No. PCT/US09/56114, filed on Sep. 4, 2009, 1 page.

(Continued)

*Primary Examiner* — Corrine M McDermott
*Assistant Examiner* — Alexander Orkin
(74) *Attorney, Agent, or Firm* — Morrison & Foerster LLP

(57) ABSTRACT

Disclosed herein is an implantable fistula closure device. The device may include an expandable longitudinally segmented body including a proximal end and a distal end. The segmented body may further include a plurality of porous bodies and a connecting member operably joining together the plurality of porous bodies. The plurality of porous bodies includes a first porous body with a proximal end and a distal end and a second porous body with a proximal end and a distal end, and the connecting member operably connects the proximal end of the first porous body with the distal end of the second porous body.

21 Claims, 25 Drawing Sheets

U.S. PATENT DOCUMENTS

| | | |
|---|---|---|
| 4,390,018 A | 6/1983 | Zukowski |
| 4,532,926 A | 8/1985 | O'Holla |
| 4,669,473 A | 6/1987 | Richards et al. |
| 4,705,040 A | 11/1987 | Mueller et al. |
| 4,744,364 A | 5/1988 | Kensey |
| 4,795,438 A | 1/1989 | Kensey et al. |
| 4,836,204 A | 6/1989 | Landymore et al. |
| 4,852,568 A | 8/1989 | Kensey |
| 4,890,612 A | 1/1990 | Kensey |
| 4,917,089 A | 4/1990 | Sideris |
| 4,935,028 A | 6/1990 | Drews |
| 4,983,177 A | 1/1991 | Wolf |
| 5,021,059 A | 6/1991 | Kensey et al. |
| 5,053,046 A | 10/1991 | Janese |
| 5,061,274 A | 10/1991 | Kensey |
| 5,122,136 A | 6/1992 | Guglielmi et al. |
| 5,192,301 A | 3/1993 | Kamiya et al. |
| 5,192,302 A | 3/1993 | Kensey et al. |
| 5,222,974 A | 6/1993 | Kensey et al. |
| 5,242,456 A | 9/1993 | Nash et al. |
| 5,258,042 A | 11/1993 | Mehta |
| 5,282,827 A | 2/1994 | Kensey et al. |
| 5,306,254 A | 4/1994 | Nash et al. |
| 5,312,435 A | 5/1994 | Nash et al. |
| 5,334,217 A | 8/1994 | Das |
| 5,350,399 A | 9/1994 | Erlebacher et al. |
| 5,354,295 A | 10/1994 | Guglielmi et al. |
| 5,374,261 A | 12/1994 | Yoon et al. |
| RE34,866 E | 2/1995 | Kensey et al. |
| 5,411,520 A | 5/1995 | Nash et al. |
| 5,441,517 A | 8/1995 | Kensey et al. |
| 5,522,836 A | 6/1996 | Palermo |
| 5,531,757 A | 7/1996 | Kensey et al. |
| 5,531,759 A | 7/1996 | Kensey et al. |
| 5,540,680 A | 7/1996 | Guglielmi et al. |
| 5,549,633 A | 8/1996 | Evans et al. |
| 5,582,619 A | 12/1996 | Ken |
| 5,609,628 A | 3/1997 | Keranen |
| 5,620,461 A | 4/1997 | Muijs Van De Moer et al. |
| 5,624,449 A | 4/1997 | Pham et al. |
| 5,643,254 A | 7/1997 | Scheldrup et al. |
| 5,645,558 A | 7/1997 | Horton |
| 5,662,681 A | 9/1997 | Nash et al. |
| 5,676,689 A | 10/1997 | Kensey et al. |
| 5,681,334 A | 10/1997 | Evans et al. |
| 5,700,277 A | 12/1997 | Nash et al. |
| 5,707,393 A | 1/1998 | Kensey et al. |
| 5,713,891 A | 2/1998 | Poppas |
| 5,725,552 A | 3/1998 | Kotula et al. |
| 5,743,905 A | 4/1998 | Eder et al. |
| 5,749,891 A | 5/1998 | Ken et al. |
| 5,752,974 A | 5/1998 | Rhee et al. |
| 5,766,219 A | 6/1998 | Horton |
| 5,782,860 A | 7/1998 | Epstein et al. |
| 5,785,679 A | 7/1998 | Abolfathi et al. |
| 5,810,884 A | 9/1998 | Kim |
| 5,824,054 A | 10/1998 | Khosravi et al. |
| 5,833,705 A | 11/1998 | Ken et al. |
| 5,855,578 A | 1/1999 | Guglielmi et al. |
| 5,861,004 A | 1/1999 | Kensey et al. |
| 5,879,366 A | 3/1999 | Shaw et al. |
| 5,904,703 A | 5/1999 | Gilson |
| 5,911,731 A | 6/1999 | Pham et al. |
| 5,916,236 A | 6/1999 | Muijs Van de Moer et al. |
| 5,935,147 A | 8/1999 | Kensey et al. |
| 5,990,379 A | 11/1999 | Gregory |
| 6,007,563 A | 12/1999 | Nash et al. |
| 6,010,517 A | 1/2000 | Baccaro |
| 6,045,569 A | 4/2000 | Kensey et al. |
| 6,063,100 A | 5/2000 | Diaz et al. |
| 6,080,183 A | 6/2000 | Tsugita et al. |
| 6,087,552 A | 7/2000 | Gregory |
| 6,090,125 A | 7/2000 | Horton |
| 6,090,130 A | 7/2000 | Nash et al. |
| 6,171,326 B1 | 1/2001 | Ferrera et al. |
| 6,179,857 B1 | 1/2001 | Diaz et al. |
| 6,179,863 B1 | 1/2001 | Kensey et al. |
| 6,183,491 B1 | 2/2001 | Lulo |
| 6,187,027 B1 | 2/2001 | Mariant et al. |
| 6,190,400 B1 | 2/2001 | Van De Moer et al. |
| 6,203,563 B1 | 3/2001 | Fernandez |
| 6,231,562 B1 | 5/2001 | Khosravi et al. |
| 6,238,403 B1 | 5/2001 | Greene, Jr. et al. |
| 6,270,495 B1 | 8/2001 | Palermo |
| 6,287,318 B1 | 9/2001 | Villar et al. |
| 6,296,658 B1 | 10/2001 | Gershony et al. |
| 6,306,153 B1 | 10/2001 | Kurz et al. |
| 6,315,787 B1 | 11/2001 | Tsugita et al. |
| 6,383,204 B1 | 5/2002 | Ferrera et al. |
| 6,454,780 B1 | 9/2002 | Wallace |
| 6,476,069 B2 | 11/2002 | Krall et al. |
| 6,503,527 B1 | 1/2003 | Whitmore et al. |
| 6,538,026 B1 | 3/2003 | Krall et al. |
| 6,551,303 B1 | 4/2003 | Van Tassel et al. |
| 6,551,305 B2 | 4/2003 | Ferrera et al. |
| 6,551,340 B1 | 4/2003 | Kónya et al. |
| 6,565,601 B2 | 5/2003 | Wallace et al. |
| 6,589,236 B2 | 7/2003 | Wheelock et al. |
| 6,592,566 B2 | 7/2003 | Kipke et al. |
| 6,599,308 B2 | 7/2003 | Amplatz |
| 6,605,101 B1 | 8/2003 | Schaefer et al. |
| 6,613,037 B2 | 9/2003 | Khosravi et al. |
| 6,623,493 B2 | 9/2003 | Wallace et al. |
| 6,623,508 B2 | 9/2003 | Shaw et al. |
| 6,635,069 B1 | 10/2003 | Teoh et al. |
| 6,638,291 B1 | 10/2003 | Ferrera et al. |
| 6,656,173 B1 | 12/2003 | Palermo |
| 6,656,201 B2 | 12/2003 | Ferrera et al. |
| 6,656,206 B2 | 12/2003 | Corcoran et al. |
| 6,676,971 B2 | 1/2004 | Goupil et al. |
| 6,682,546 B2 | 1/2004 | Amplatz |
| 6,699,484 B2 | 3/2004 | Whitmore et al. |
| 6,723,108 B1 | 4/2004 | Jones et al. |
| 6,730,108 B2 | 5/2004 | Van Tassel et al. |
| 6,764,500 B1 | 7/2004 | Muijs Van De Moer et al. |
| 6,790,218 B2 | 9/2004 | Jayaraman |
| 6,872,218 B2 | 3/2005 | Ferrera et al. |
| 6,921,410 B2 | 7/2005 | Porter |
| 6,949,113 B2 | 9/2005 | Van Tassel et al. |
| 6,953,468 B2 | 10/2005 | Jones et al. |
| 6,974,862 B2 | 12/2005 | Ringeisen et al. |
| 6,979,344 B2 | 12/2005 | Jones et al. |
| 6,994,717 B2 | 2/2006 | Kónya et al. |
| 6,997,918 B2 | 2/2006 | Soltesz et al. |
| 7,011,677 B2 | 3/2006 | Wallace et al. |
| 7,033,348 B2 | 4/2006 | Alfano et al. |
| 7,049,348 B2 | 5/2006 | Evans et al. |
| 7,070,608 B2 | 7/2006 | Kurz et al. |
| 7,166,133 B2 | 1/2007 | Evans et al. |
| 7,169,168 B2 | 1/2007 | Muijs Van De Moer et al. |
| 7,179,276 B2 | 2/2007 | Barry et al. |
| 7,182,774 B2 | 2/2007 | Barry et al. |
| 7,214,765 B2 | 5/2007 | Ringeisen et al. |
| 7,294,123 B2 | 11/2007 | Jones et al. |
| 7,316,701 B2 | 1/2008 | Ferrera et al. |
| 7,323,000 B2 | 1/2008 | Monstdt et al. |
| 7,326,225 B2 | 2/2008 | Ferrera et al. |
| 7,485,087 B2 | 2/2009 | Burgard |
| 7,491,214 B2 | 2/2009 | Greene, Jr. et al. |
| 2003/0220666 A1 | 11/2003 | Mirigian et al. |
| 2004/0044358 A1 | 3/2004 | Khosravi et al. |
| 2004/0044391 A1 | 3/2004 | Porter |
| 2004/0186464 A1 | 9/2004 | Mamayek et al. |
| 2004/0199175 A1 | 10/2004 | Jaeger et al. |
| 2004/0225183 A1 | 11/2004 | Michlitsch et al. |
| 2004/0236344 A1 | 11/2004 | Monstadt et al. |
| 2004/0236348 A1 | 11/2004 | Diaz et al. |
| 2004/0237970 A1 | 12/2004 | Vournakis et al. |
| 2005/0033401 A1 | 2/2005 | Cunniffe et al. |
| 2005/0049626 A1 | 3/2005 | Burgard |
| 2005/0070759 A1 | 3/2005 | Armstrong |
| 2005/0090860 A1* | 4/2005 | Paprocki .................. 606/213 |
| 2005/0090861 A1 | 4/2005 | Porter |
| 2005/0113858 A1 | 5/2005 | Deutsch |
| 2005/0159776 A1 | 7/2005 | Armstrong |
| 2005/0240216 A1 | 10/2005 | Jones et al. |
| 2005/0251200 A1 | 11/2005 | Porter |

| | | |
|---|---|---|
| 2006/0009797 A1 | 1/2006 | Armstrong |
| 2006/0036282 A1 | 2/2006 | Wahr et al. |
| 2006/0052822 A1 | 3/2006 | Mirizzi et al. |
| 2006/0058834 A1 | 3/2006 | Do et al. |
| 2006/0074447 A2 | 4/2006 | Armstrong |
| 2006/0079929 A1 | 4/2006 | Marks et al. |
| 2006/0122633 A1 | 6/2006 | To et al. |
| 2006/0155303 A1 | 7/2006 | Konya et al. |
| 2006/0200192 A1 | 9/2006 | Fitz et al. |
| 2006/0206140 A1 | 9/2006 | Shaolian et al. |
| 2006/0206196 A1 | 9/2006 | Porter |
| 2006/0265001 A1 | 11/2006 | Marks et al. |
| 2006/0271099 A1 | 11/2006 | Marks et al. |
| 2006/0282112 A1 | 12/2006 | Griffin |
| 2007/0031508 A1 | 2/2007 | Armstrong et al. |
| 2007/0083226 A1 | 4/2007 | Buiser et al. |
| 2007/0088445 A1 | 4/2007 | Patel et al. |
| 2007/0129757 A1 | 6/2007 | Armstrong |
| 2007/0135842 A1 | 6/2007 | Van de Moer et al. |
| 2007/0142859 A1 | 6/2007 | Buiser et al. |
| 2007/0185530 A1 | 8/2007 | Chin-Chen et al. |
| 2007/0198059 A1 | 8/2007 | Patel et al. |
| 2007/0233278 A1 | 10/2007 | Armstrong |
| 2007/0244502 A1 | 10/2007 | Deutsch |
| 2007/0276121 A1 | 11/2007 | Westergom et al. |
| 2008/0004657 A1 | 1/2008 | Obermiller et al. |
| 2008/0015635 A1 | 1/2008 | Olsen et al. |
| 2008/0015636 A1 | 1/2008 | Olsen et al. |
| 2008/0027477 A1 | 1/2008 | Obermiller et al. |
| 2008/0039547 A1 | 2/2008 | Khatri et al. |
| 2008/0039548 A1 | 2/2008 | Zavatsky et al. |
| 2008/0051831 A1 | 2/2008 | Deal et al. |
| 2008/0245374 A1 | 10/2008 | Agnew |
| 2009/0054927 A1 | 2/2009 | Agnew |

FOREIGN PATENT DOCUMENTS

| | | |
|---|---|---|
| WO | WO-00/74576 A1 | 12/2000 |
| WO | WO-2005/070302 A1 | 8/2005 |
| WO | WO-2006/119256 A2 | 11/2006 |
| WO | WO-2006/119256 A3 | 11/2006 |
| WO | WO-2007/002260 A2 | 1/2007 |
| WO | WO-2007/002260 A3 | 1/2007 |

OTHER PUBLICATIONS

Written Opinion of the International Searching Authority mailed on Oct. 21, 2009, for PCT Patent Application No. PCT/US09/56114, filed on Sep. 4, 2009, 11 pages.

* cited by examiner

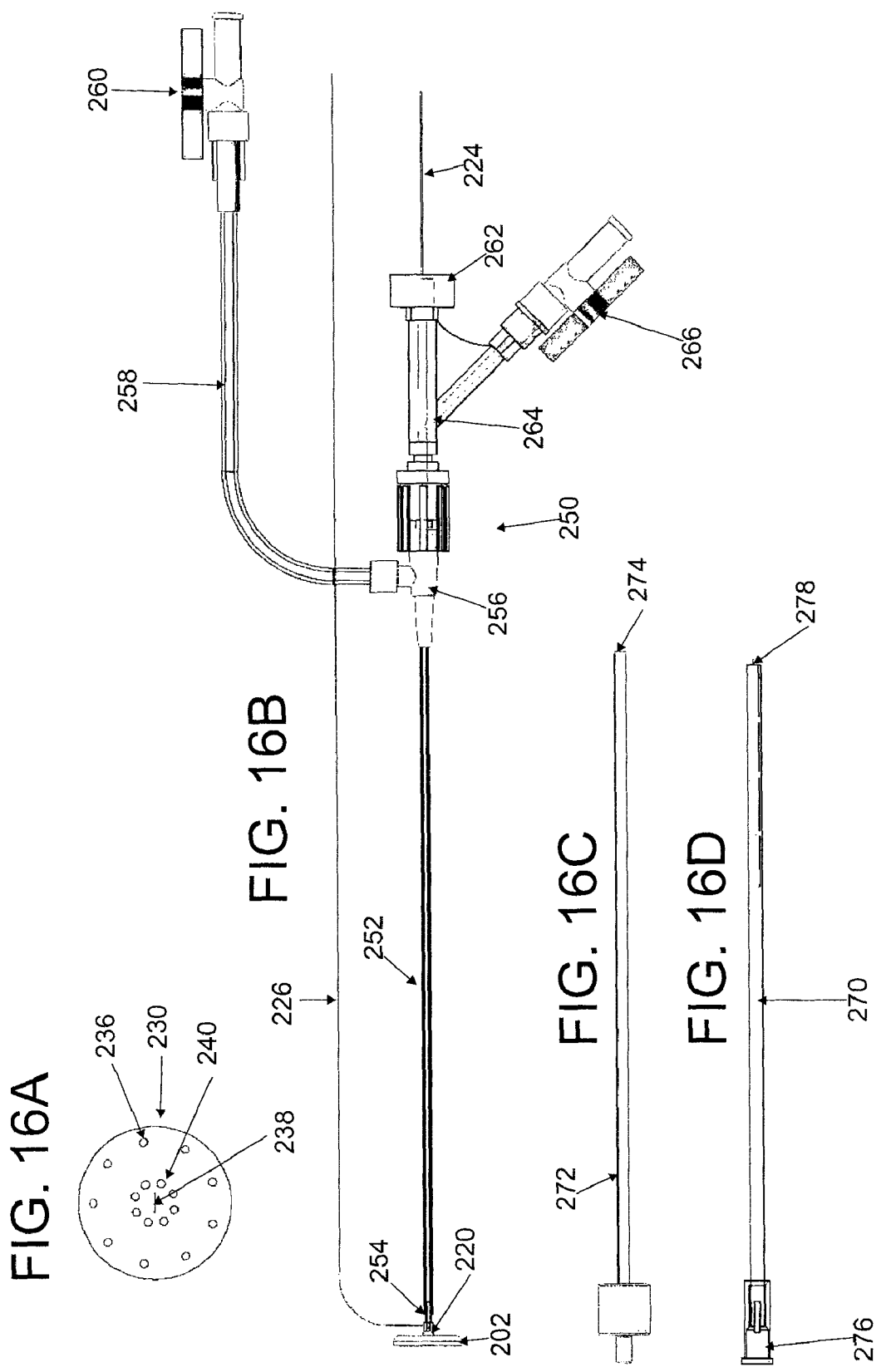

INFLATABLE DEVICE FOR ENTERIC FISTULA TREATMENT

CROSS-REFERENCE TO RELATED APPLICATIONS

The present application is a continuation of U.S. application Ser. No. 12/554,758 filed on Sep. 4, 2009, now U.S. Pat. No. 8,177,809, which claims priority under 35 U.S.C. §119 (e) to U.S. Provisional Application No. 61/094,378 filed on Sep. 4, 2008, the disclosure of which is incorporated by reference herein in its entirety.

FIELD OF THE INVENTION

The present invention relates to medical apparatus and methods. More specifically, the present invention relates to implantable devices for closing fistulas and methods of using such devices.

BACKGROUND OF THE INVENTION

Fistulas are a major cause of morbidity and mortality, as there are over one hundred thousand cases of pathologic fistulas a year, which account for over ten thousand deaths. They cost the healthcare system billions of dollars each year to treat.

Fistulas are tissue-lined connections between body cavities and hollow organs or between such cavities or organs and the surface of the body. The fistula tract includes a void in the soft tissues extending from a primary fistula opening to a blind ending or leading to one or more secondary fistula opening. Fistulas frequently develop as a consequence of infections or accompany abscess formations. Although some fistulas are purposely created for therapeutic purposes such as tracheostomy tracts, gastric feeding tube tracts, or arterio-venous fistulas for dialysis access, pathological fistulas are abnormal tracts that typically occur either congenitally or form after surgery, surgery-related complications, or trauma. They are most often open tracts that have epithelialized, endothelialized, or mucosalized.

Fistulas can form between almost any two-organ systems. For example, they may occur between internal organs and skin (enterocutaneous fistulas, gastrocutaneous fistulas, anal fistulas, rectovaginal fistulas, colocutaneous fistulas, vesiclocutaneous fistulas, intestinocutaneous fistulas, tracheocutaneous fistulas, brochocutaneous fistulas, etc.) or between internal organs themselves (tracheal-esophogeal fistulas, gastrointestinal fistulas, colovesicular fistulas, palatal fistulas, etc.). Fistulas may also form between blood vessels such as arterial-venous fistulas.

Although fistulas may form in many locations in the body, they are almost universally highly morbid to patients and difficult for clinicians to treat. For example, enterocutaneous fistulas are one of the most feared complications of abdominal surgery. Enterocutaneous fistulas are abnormal connections that form between the bowel and skin and can occur after abdominal surgery, after trauma, or as a complication of Crohn's disease. Some reports estimate that enterocutaneous fistulas may form in as many as 1% of patients that undergo major abdominal surgery. They often require months of supportive care and/or major abdominal surgery. The overall mortality rate for patients that develop enterocutaneous fistulas remains high at around 20%.

Current options for treatment of enterocutaneous fistulas include long-term conservative management or major surgery. In a first option, the patients are placed on restricted enteric intake and managed with parenteral nutritional support. The fistula leakage is controlled using a stoma bag. If the fistula output is high, drains are sometimes placed to try and control the fistula output. Spontaneous closure is relatively low at around 25%. If fistulas fail to spontaneously close with current management after 5 weeks of bowel rest, then many surgeons advocate surgical treatment at this point, though supportive care could continue indefinitely. Patients with open fistula tracts often have ongoing associated malnutrition and electrolyte imbalance issues as well as chronic non-healing abdominal wounds.

A second option is a major surgery, which has a mortality rate near 30%. The surgery involves resection of the diseased intestinal segment, extirpation of the fistula, and debridement of the fistulous tract through the abdominal wall and subcutaneous tissue. This major abdominal surgery often requires blood transfusion and post-operative ICU admissions. As a result of chronic inflammation and having previously operated on abdomens, these patients typically form dense adhesions and have highly friable tissues. In addition, these patients can be severely malnourished. These conditions make operations on enterocutaneous fistulas extremely difficult and dangerous. After the surgery the patient is put on total parenteral nutrition ("TPN") for several more days before the patient can be weaned off TPN and slowly introduced to normal foods.

Other treatment options may include implantable devices designed to aid in the closure of the fistula. These devices, however, may cause adverse immunological reactions in patients, may allow leakage of fluid around the device, or the device may migrate or become dislodged when the patient exerts himself, such as during exercise. There is a need in the art for an implantable device for closing a fistula that reduces the chance of adverse immunological reactions, reduces the leakage of fluid through the fistula tract and reduces the chance of migration or dislodgement of the device.

SUMMARY

Disclosed herein is an implantable fistula closure device. In one embodiment, the device includes an expandable longitudinally segmented body including a proximal end and a distal end. In one embodiment, the segmented body further includes a plurality of porous bodies and a connecting member operably joining together the plurality of porous bodies. The plurality of porous bodies includes a first porous body with a proximal end and a distal end and a second porous body with a proximal end and a distal end, and the connecting member operably connects the proximal end of the first porous body with the distal end of the second porous body.

In one embodiment, a method of treating an enterocutaneous fistula is provided, comprising inserting an expandable disc attached to first and second bioresorbable tethers into a enterocutaneous fistula tract, wherein the disc is in a collapsed configuration, positioning the expandable disc distal to a distal tract opening of the enterocutaneous fistula tract, expanding the expandable disc from the collapsed configuration to an expanded configuration, conforming the expandable disc to the distal tract opening by tensioning the first tether attached to the expandable disc, filling the fistula tract with a plurality of elongate bioresorbable foam expansion members using the second tether, and maintaining the expandable disc against the distal tract opening by restraining the first and second tethers in a tensioned state by fixing a proximal anchor to the tethers across a proximal tract opening of the enterocutaneous fistula tract. The expandable disc may comprise an annular member and a plurality of radial members. The method may further comprise threading the second tether through a loop attached to the plurality of a plurality of elongate bioresorbable foam expansion members. The method may further comprise applying suction through the proximal anchor to reduce the pressure within the fistula tract. The method may also further comprise collapsing the expandable disc into the collapsed configuration using negative pressure. Expanding the expandable disc may comprise inflating the expandable disc.

In another embodiment, a fistula treatment kit is provided, comprising a expandable disc with an aspiration lumen, a first and second tether coupled to the disc, a catheter configured to couple to the aspiration lumen of the expandable disc, a plurality of elongate bioresorbable foam expansion members configured for insertion into an enterocutaneous fistula, and a proximal anchor with at least one aperture that permits slidable coupling to the first and second tethers and a tissue contact surface configured to resist passage into the enterocutaneous fistula. At least one elongate bioresorbable foam expansion member may comprise a loop configured to slidably couple to the second tether. The proximal anchor may comprise at least one suction channel.

In another embodiment, a method of treating a tissue tract is provided, comprising inserting a non-resorbable expandable member into a tissue tract in communication with a body lumen, expanding the expandable member, tensioning a first tether attached to the expandable member, placing a bioresorbable material into the fistula tract, and restraining the first tether in a tensioned state. The method may further comprise collapsing the non-resorbable member. Collapsing the non-resorbable member may be performed using negative pressure. The method may further comprise conforming the expandable member to a junction between the tissue tract and the body lumen. The tissue tract may be an enterocutaneous fistula tract, enteroenteral fistula tract, or a gastro-gastric fistula. Restraining the first tether in a tensioned state may comprise attaching a proximal anchor to the first tether, wherein the proximal anchor is located against a tissue surface. The method may further comprise applying negative pressure to the tissue tract using a suction channel of the proximal anchor. The method may further comprise sealing at least a portion of the tissue tract with the expandable member. The bioresorbable material may comprise at least one foam structure. Placing the bioresorbable material into the tissue tract comprises sliding at least one foam structure along a second tether. Sliding at least one foam structure may be performed using a loop attached to at least one foam structure. The method may further comprise threading the loop using the second tether.

In another example, a non-vascular fistula treatment kit may be provided, comprising a collapsible member comprising an aspiration lumen and a tether attachment structure, and wherein the collapsible is configured for positioning within a body lumen, a tether attached to the collapsible member, and a bioresorbable material configured for placement in a non-vascular fistula tract. The kit may further comprise a delivery tool with an aspiration channel, wherein the delivery tool is configured for detachable coupling to the collapsible member. The bioresorbable material may comprise a plurality of foam members, each foam member comprising a first end, a second end, and a body therebetween. Each foam member may be an elongate foam member. The plurality of foam members may be attached using a flexible element comprising a looped end structure. The kit may further comprise a proximal anchor that is attachable to the tether and comprising a tissue contact surface, a delivery cannula configured to permit insertion of the delivery tool, and/or a proximal anchor that is configured for coupling to the tether.

In another embodiment, a non-vascular fistula treatment kit may be provided, comprising an expandable member configured for delivery into an intestinal lumen and comprising a tether attachment structure and an arcuate member, and a tether attached to the expandable member. The expandable member may have a disc-shaped face. The arcuate member is an arcuate channel. The expandable member may further comprise at least one radial member. The arcuate member may be an arcuate channel and the at least one radial member may be at least one radial channel. The arcuate channel may be an arcuate lumen and the at least one radial channel may be at least one radial lumen. The kit may further comprise a proximal anchor that is fixably attachable to the tether and comprising a tissue contact surface. The kit may further comprise a delivery catheter releasably attachable to the expandable member, a plurality of resorbable members located in a cannula, and a cannula push member configured for insertion into the cannula. The plurality of resorbable members may be serially attached. At least one of the plurality of resorbable members may be attached to a loop structure.

In another embodiment, a method of treating a fistula is provided, comprising inserting an expandable occluder attached to at least one tether in its collapsed state through a tissue tract toward a body lumen using a tubular member, wherein the disc occluder is non-resorbable, tensioning at least one tether to conform the expandable occluder against a surface of the body lumen, separating the tubular member from the expandable occluder, removing the tubular member from the tissue tract, implanting a plurality of bioresorbable expansion members within the tissue tract, wherein at least one of the bioresorbable expansion members is attached at least one tether, and restraining the tether in a tensioned state by fixing the tether to a proximal anchor located against a tissue surface different from the surface of the body lumen. The plurality of bioresorbable expansion members may be interconnected.

In still another embodiment, a fistula treatment kit is provided, comprising
at least one tube containing at least four interconnected elongate bioresorbable expansion members, a push member configured to push the expansion members out of the tube, an expandable occluding member comprising a substantially non-elastic polymer material. The fistula treatment kit may further comprise at least two tubes, each containing at least four interconnected expansion members.

In another embodiment, a method of treating a tissue tract is provided, comprising inserting an occluding member into a tissue tract toward an anatomical body space, occluding the tissue tract by applying the occluding member against a surface of the body space, and filling the tissue tract with a first bioresorbable material without pre-coupling the first bioresorbable material to the inserted occluding member. The method may further comprise restraining the occluding member against the surface of the body space by fixing the occluding member against a surface transverse to the tissue tract, and/or positioning a filling device between the occluding member and a wall of the tissue tract. The first bioresorbable material may comprise a plurality of discrete or interconnected bioresorbable structures. The method may further comprise pushing at least two bioresorbable structures out of the filling device, and/or expanding the occluding member. Expanding the occluding member may comprise decreasing a first dimension of the occluding member while increasing a second dimension of the occluding member that is transversely oriented to the first dimension. The first dimension may be a longitudinal length of the occluding member. Expanding the occluding member may comprise expanding the occluding member along a second dimension to a size of at least four times or greater than a size of the occluding member along a first dimension, wherein the second dimension is transversely oriented to the first dimension. The occluding member may be expanded along the second dimension to a size of at least 2 cm or greater. Inserting the occluding member may occur before filling the tissue tract with the bioresorbable material. The method may further comprise evacuating the tissue tract. The method may further comprise sealing the evacuated tissue tract to resist gaseous inflow, which may comprise reducing the pressure of the tissue tract by about 100 mm Hg to about 325 mm Hg from the ambient pressure. The body space is a portion of a gastrointestinal lumen. The portion of the gastrointestinal lumen may be located distal to the ligament of Trietz and proximal to the rectum. The transverse surface may be a skin surface. The method may further comprise, directly visualizing the insertion of the occluding member using a fiberscope. Inserting the occluding member into the tissue tract may be performed using a flexible catheter. Occluding the tissue tract may comprise tensioning a tether of the occluding member. The method may also include debriding the tissue tract before filling the tissue tract with a first bioresorbable material.

In another embodiment, a tissue tract treatment system, comprising an expandable distal anchor comprising an anchor attachment site and having a delivery configuration with a first cross-sectional area and a deployment configuration with a second cross-sectional area greater than the first cross-sectional area, an anchor tether, a first delivery tube configured to deliverably retain the expandable distal anchor and the anchor tether, and a plurality of expandable fill structures located in a second delivery tube. The expandable fill structures may comprise elongate polymeric members. The elongate polymeric members may be compressed elongate polymeric members. The plurality of expandable fill structures may be interconnected.

Disclosed herein is an implantable fistula closure device. In one embodiment, the device includes an expandable feature, a longitudinally extending connecting member extending proximally from the expandable feature, and a body formed of at least one of a liquid-like and gel-like material configured to be deployed along the connecting member subsequent to the connecting member being deployed in a fistula tract.

A method of treating a fistula tract is disclosed herein. In one embodiment, the method includes: providing a fistula closure device including a segmented body; delivering the device with its segmented body in a compressed state into the fistula tract; and allowing the segmented body to expand to approximate the volume of the fistula tract.

A method of treating a fistula tract is disclosed herein. In one embodiment, the method includes: providing a fistula closure device including a thread-like member and a expandable anchor member; delivering the device with its expandable anchor member in a compressed state into the fistula tract, the thread-like member extending along the fistula tract; expanding the expandable anchor member in a distal opening of the fistula tract; and injecting at least one of a fluid, gel and fragmented solid into the fistula tract along the thread-like member.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

In one embodiment, a method of treating an enterocutaneous fistula is provided, comprising inserting an inflatable disc-shaped balloon attached to a bioresorbable tether into a enterocutaneous fistula tract, positioning the disc-shaped balloon at a distal tract opening between the fistula tract and a gastrointestinal tract, inflating the disc-shaped balloon with a curable silicone, conforming the disc-shaped balloon to the distal tract opening by tensioning the tether attached to the disc-shaped balloon, maintaining the tension of the tether at least until the curable silicone is substantially cured in a conformed configuration, filling the fistula tract with a plurality of elongate bioresorbable foam expansion members, and sealing the distal tract opening with the disc-shaped balloon by restraining the tether in a tensioned state by fixing a proximal anchor to the tether across a proximal tract opening of the fistula tract. The disc-shaped balloon may comprise a proximal end and a distal end, a first configuration having a first distance between the proximal end and the distal end, and a second configuration having a second distance between the proximal end and the distal end that is shorter than the first distance. The method may further comprise transitioning the disc-shaped balloon from the first configuration toward the second configuration. The first configuration may have a first transverse dimension and the second configuration has a second transverse dimension that is larger than the first transverse dimension. Filling the fistula tract with a plurality of elongate bioresorbable foam expansion members may comprise sliding the plurality of bioresorbable foam expansion members distally along the tether. The method may also further comprise applying suction through the proximal anchor to reduce the pressure within the fistula tract.

In another embodiment, an enterocutaneous fistula treatment kit is provided comprising a disc-shaped balloon with an inflation lumen, a tether coupled to the balloon, a syringe with an inflation tip configured to couple to the inflation lumen of the disc-shaped balloon, a curable silicone material configured for inflation by the syringe, a plurality of elongate bioresorbable foam expansion members configured for insertion into an enterocutaneous fistula, and a proximal anchor with at least one aperture that permits slidable coupling to the tether and a skin contact surface configured to resist passage into the enterocutaneous fistula. At least one elongate bioresorbable foam expansion member may comprise a through lumen that permits slidable coupling to the tether, and/or the proximal anchor may comprise at least one suction channel.

In another embodiment, a method of treating a tissue tract, comprising inserting a non-resorbable expandable disc-shaped member into a tissue tract in communication with a body lumen, inflating the disc-shaped member, tensioning a bioresorbable tether attached to the disc-shaped member, placing a bioresorbable material into the fistula tract, and restraining the tether in a tensioned state. The disc-shaped member may be inflated with a substance having a flowable state and a non-flowable state. The substance may comprise a curable polymer. The method may also further comprise conforming the disc-shaped member to a junction between the tissue tract and the body lumen and/or maintaining the tension of the tether until the curable polymer is substantially set in a conformed configuration. In some embodiments, restraining the tether in a tensioned state may comprise attaching a proximal anchor to the tether, wherein the proximal anchor is located against a skin surface. The method may further comprise suctioning the enterocutaneous fistula tract using a suction channel of the proximal anchor. The method may also further comprise sealing the tissue tract with the disc-shaped member to resist migration of the bioresorbable material into the body lumen. The bioresorbable material may comprise at least one foam structure. Placing the bioresorbable material into the fistula tract may comprise sliding at least one foam structure along the tether.

In another embodiment, a method of treating a tissue tract is provided, comprising inserting a non-resorbable expandable member into a tissue tract in communication with a body lumen, wherein the expandable member comprises a proximal end, a distal end, and a frame with at least two longitudinally oriented strut members, expanding the expandable member by moving at least two longitudinally oriented strut members in a radially outward direction, tensioning a bioresorbable tether attached to the member, placing a bioresorbable material into the tissue tract, and restraining the tether in a tensioned state. In some embodiments, expanding the expandable member may comprise changing the expandable member from a generally tapered configuration toward a generally planar configuration. The frame may also comprise a slotted tube and wherein each longitudinally oriented strut member has a proximal attached end and a distal attached end. The frame comprises umbrella configuration wherein each longitudinally oriented strut member has a proximal attached end and a distal free end.

In still another embodiment, a non-vascular fistula treatment kit is provided, comprising an inflatable disc-shaped balloon comprising an inflation lumen and a tether attachment structure, and wherein the balloon is configured for positioning within an intestinal lumen, a tether, and a bioresorbable material configured for placement in a non-vascular fistula tract. The kit may also further comprise an inflation tool with an inflation channel configured for detachable coupling to the inflation lumen of the disc-shaped balloon, and wherein the inflation tool may be a syringe filled with a curable liquid. The bioresorbable material may comprise a plurality of elongate foam members, each elongate foam member comprising a first end, a second end, and a body therebetween. The kit may further comprise a proximal anchor that is fixably attachable to the tether and comprising a skin contact surface, a delivery cannula, and/or a proximal anchor that is configured for coupling to the tether.

In one embodiment, a non-vascular fistula treatment kit is provided, comprising an expandable member configured for delivery into an intestinal lumen and comprising a tether attachment structure, a frame with at least two longitudinally oriented strut members and a polymeric covering associated with the frame, a tether, and a bioresorbable material configured for placement in a non-vascular fistula tract. The kit may further comprise an expansion tool with an elongate pull member configured to detachably couple to the frame of the expandable member. In some instances, the bioresorbable material may comprise a plurality of elongate foam members, each elongate foam member comprising a first end, a second end, and a body therebetween. The kit may also further comprise a proximal anchor that is fixably attachable to the tether and comprising a skin contact surface. The frame may comprise a slotted tube configuration or an umbrella configuration, for example. Also, the kit may further comprise a delivery cannula.

A method of treating an enterocutaneous fistula, comprising inserting an inflatable disc occluder attached to a bioresorbable tether in its collapsed state through a fistula tract toward a gastrointestinal lumen using a flexible tubular member, wherein the disc occluder is non-resorbable, filling the inflatable disc occluder with a curable liquid silicone using the flexible tubular member, tensioning the tether to conform the inflatable disc occluder against the gastrointestinal lumen while curing the liquid silicone, separating the flexible tubular member from the inflatable disc occluder, removing the flexible tubular member from the fistula tract, implanting a plurality of bioresorbable foam expansion members within the fistula tract, wherein at least one of the bioresorbable foam expansion members is unattached to the tether, and restraining the tether in a tensioned state by fixing the tether to a proximal anchor located against a skin surface. Each of the plurality of bioresorbable foam expansion members may be unattached to the tether. The method may further comprise evacuating the flexible tubular member before filling the inflatable disc occluder with the curable liquid silicone.

In one embodiment, a fistula treatment kit is provided, comprising one or more tubes containing at least ten elongate bioresorbable foam expansion members, a push member configured to push the elongate bioresorbable foam expansion members out of the tubes, an expandable occluding member comprising a substantially non-elastic polymer material. The fistula treatment kit may further comprise at least two tubes, each containing at least 4 foam expansion members.

In one embodiment, a method of treating a tissue tract, comprising inserting an occluding member into a tissue tract toward an anatomical body space, occluding the tissue tract by applying the occluding member against a surface of the body space, and filling the tissue tract with a first bioresorbable material without pre-coupling the first bioresorbable material to the inserted occluding member. The method may further comprise restraining the occluding member against the surface of the body space by fixing the occluding member against a surface transverse to the tissue tract. The method may also further comprise positioning a filling device between the occluding member and a wall of the tissue tract. Also, the first bioresorbable material may comprise a plurality of discrete bioresorbable structures. The method may also further comprise pushing at least two bioresorbable structures out of the filling device, and/or expanding the occluding member. In some examples, expanding the occluding member may comprise decreasing a first dimension of the occluding member while increasing a second dimension of the occluding member that is transversely oriented to the first dimension. The first dimension may be a longitudinal length of the occluding member. Expanding the occluding member may comprise expanding the occluding member along a second dimension to a size of at least four times or greater than a size of the occluding member along a first dimension, wherein the second dimension is transversely oriented to the first dimension. Sometimes, the occluding member may be expanded along the second dimension to a size of at least 2 cm or greater. The occluding member may comprise an inflatable balloon with a balloon opening and wherein expanding the occluding member may comprise increasing the volume of inflatable balloon from a first volume to a second volume. Expanding the occluding member may also comprise inflating the inflatable balloon with a curable material using an inflation device. The method may further comprise separating the curable material in the inflatable balloon and the curable material in the inflation device by passing a separation structure of the inflation device across the balloon opening. Occasionally, inserting the occluding member may occur before filling the tissue tract with the bioresorbable material. The method may also further comprise evacuating the tissue tract, sealing the evacuated tissue tract to resist gaseous inflow, and/or reducing the pressure of the tissue tract by about 100 mm Hg to about 325 mm Hg from the ambient pressure. The body space may be a portion of a gastrointestinal lumen. The method of claim 61, wherein the portion of the gastrointestinal lumen is located distal to the ligament of Trietz and proximal to the rectum. The transverse surface may be a skin surface, but may also be a wound or fistula surface. The method may also further comprise, directly visualizing the insertion of the occluding member using a fiberscope. Inserting the occluding member into the tissue tract may be performed using a flexible catheter. Also, occluding the tissue tract may comprise tensioning a tether of the occluding member.

In another embodiment, a tissue tract treatment system is provided, comprising an expandable distal anchor comprising an anchor attachment site and having a delivery configuration with a first cross-sectional area and a deployment configuration with a second cross-sectional area greater than the first cross-sectional area, an anchor tether, a first delivery tube configured to deliverably retain the expandable distal anchor and the anchor tether, and a plurality of expandable fill structures located in a second delivery tube. In some embodiments, the expandable fill structures may comprise elongate polymeric members, the elongate polymeric members may be compressed elongate polymeric members, and/or the expandable distal anchor may comprise an inflatable balloon with an inflation lumen. The system may also further comprise a balloon injector, wherein the balloon injector may optionally comprise a distal end and an injection aperture located proximal to the distal end.

BRIEF DESCRIPTION OF THE DRAWINGS

FIG. 16A is a superior view of the proximal retaining structure in FIG. 15. FIG. 16B is a schematic side elevational view of the delivery instrument for the device depicted in FIG. 15. FIGS. 16C and 16D are examples of an expandable member actuator and delivery catheter, respectively.

DETAILED DESCRIPTION

Figure 1A:
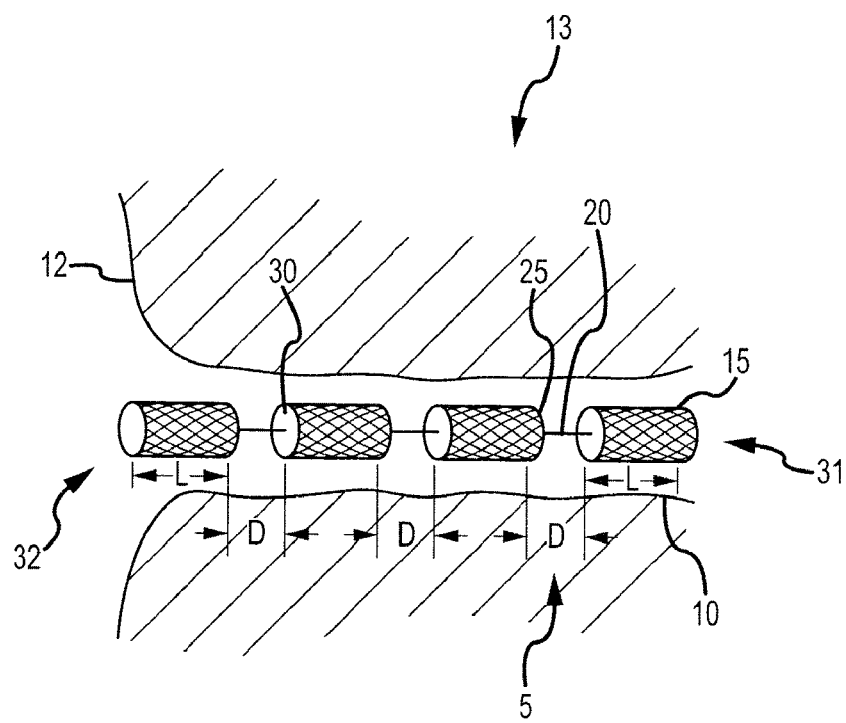
FIG. 1A is an isometric view of an implantable fistula closure device having a segmented body and located in a fistula tract in a compressed or non-expanded state.

Fistula tracts 10 can be nonlinear or curvilinear and contain cavities of varying sizes at different intervals within the tract. An implantable fistula closure device 5 disclosed herein employs advantageous design, configuration techniques and attributes to accommodate such constraints. For example, in one embodiment, the device 5 may have a segmented expandable body 13 formed of a plurality of individual expandable bodies or members 15 coupled together in an immediately adjacent abutting fashion or in a spaced-apart fashion. Upon being inserted into the fistula tract 10 with its expandable members 15 in a collapsed or compressed state, which allows for convenient insertion of the device 5 into the fistula tract 10, the expandable members 15 are allowed to expand to fill the portion of the fistula tract 10 in which each expandable member 15 is located. The segmented nature of the body 13 of the device 5 or, more specifically, the fact the device's body 13 is formed of a plurality of individual members 15 allows the body 13 to be more easily placed in and more readily conform to the tortuous and diametrically varying configuration of a fistula tract 10 when expanded within the fistula tract. Thus, once the body 13 is allowed to expand within the fistula tract, the device generally completely fills the fistula tract. In one embodiment, when the body 13 expands to fill the fistula tract, the device may generally stop fluid flow from the bowel from running out through the fistula tract by occluding the distal end of the tract via a distal end of the device body 13 that is generally non-porous or has an ability to seal the distal end of the tract. However, generally speaking, a fistula tract will leak fluid from within the tissue walls surrounding the fistula tract and some of this fluid will be absorbed by the device and the remaining fluid will drain out of the proximal end of the tract, potentially through the proximal end of the device body 13, which is generally porous or has the ability to allow the passage of fluids while generally occluding or filling the tract.

Preventing bodily fluids that originate at the distal end of the tract (e.g., bowel fluids) from passing through a fistula tract 10 and, in some embodiments, also reducing the amount or rate of flow through the fistula tract for body fluids originating in the tract itself may significantly reduce the time to closure and reduce the necessity for surgery. In one embodiment, the device 5 disclosed herein may reduce or eliminate the passage of fluids through the tract 10 as well as providing a matrix that promotes tissue growth. This device 5 may be utilized to treat a variety of clinically significant fistulas 10, including enterocutaneous fistulas, anal fistulas, bronchopleural fistulas, non-healing g-tube tracts, tracheal-esophogeal fistulas, and others.

Figure 1B:
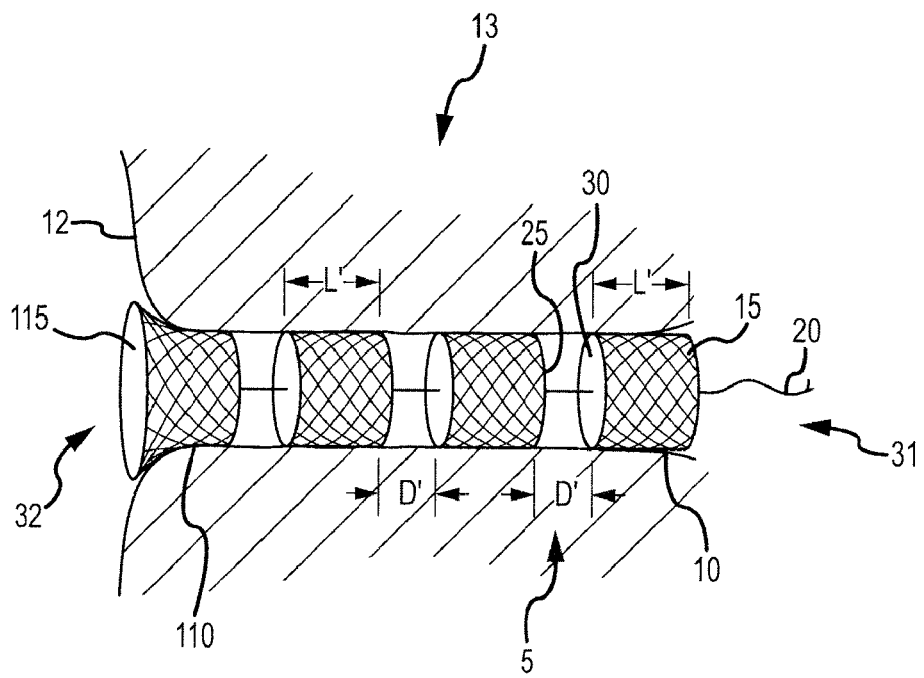
FIG. 1B is the same view as FIG. 1A, except the implantable fistula closure device is in a non-compressed or expanded state within the fistula tract.

For a discussion of an embodiment of the implantable fistula closure device 5, reference is made to FIGS. 1A and 1B. FIG. 1A is an isometric view of the device 5 located in a fistula tract 10 in a compressed or non-expanded state, and FIG. 1B is the same view as FIG. 1A, except the device 5 is in a non-compressed or expanded state. As shown in FIGS. 1A and 1B, the implantable fistula closure device 5 includes a proximal end 31, a distal end 32, and an expandable body 13 formed of a plurality of individual porous bodies 15 operably connected via a connecting member 20. Each porous body 15 includes a proximal end 25 and a distal end 30. Each porous body 15 is adapted to expand from a compressed or non-expanded state (FIG. 1A) to a non-compressed or expanded state (FIG. 1B) after insertion into the tract 10, thereby filling any cavities within the tract 10 and approximating the fistula tract walls.

As can be understood from FIG. 1A, in some embodiments, when the bodies 15 are in a compressed or non-expanded state, the bodies 15 will be spaced-apart from each other along the length of the device 5 to form a segmented configuration for the device body 13. In some embodiments, the spaced-apart distances D between adjacent proximal and distal ends 25, 30 of the bodies 15 in a compressed or non-expanded state is between approximately zero mm and approximately five mm. In one embodiment, the space apart distance D between adjacent proximal and distal ends 25, of the bodies 15 in a compressed or non-expanded state are between approximately zero mm and approximately 25 mm. Where the distance D between immediately adjacent bodies 15 is approximately zero mm when the bodies 15 are in a non-expanded state, the bodies 15 will be said to be in an abutting or touching configuration, as opposed to a spaced-apart condition. Regardless, the device body 13 will still be considered to be segmented on account of the device body 13 being formed of a plurality of individual porous bodies 15.

In some embodiments, the spaced-apart distances D between adjacent proximal and distal ends 25, 30 of the bodies 15 in a compressed or non-expanded state are between approximately zero percent and approximately two and one-half percent of the overall non-expanded length L of a body 15. Where the distance D between immediately adjacent bodies 15 is approximately zero percent of the length L of a body 15 when the bodies 15 are in a non-expanded state, the bodies 15 will be said to be in an abutting or touching configuration, as opposed to a spaced-apart condition. Regardless, the device body 13 will still be considered to be segmented on account of the device body 13 being formed of a plurality of individual porous bodies 15.

Regardless of whether the bodies are in a spaced-apart configuration or an abutting or touching configuration when the bodies 15 are in the compressed state depicted in FIG. 1A, the segmented configuration of the device body 13 facilitates the device body 13 being inserted in and conforming to the tortuous diametrically varied route formed by the tract 10.

As can be understood from FIG. 1B, when the bodies 15 are fully expanded within the tract 10, the spaced-apart distances D' between adjacent proximal and distal ends 25, 30 of bodies 15 in a non-compressed or expanded state is between approximately zero mm and approximately five mm. In some embodiments, the spaced-apart distances D' between adjacent proximal and distal ends 25, 30 of the bodies 15 in a non-compressed or expanded state is between approximately zero percent and approximately two and one-half percent of the overall expanded length L' of a body 15. The expansion of the bodies 15 after insertion into the fistula tract 10 allows the device body 13 to approximate the walls of the fistula tract, as well as fill open cavities. Because the segmented configuration of the device body 13 allows the device to closely conform to the tortuous and diametrically varied route formed by the tract 10, the bodies 15, when in an expanded state within the tract 10 generally fill the tract 10 in a manner that minimizes voids and dead space. Minimizing voids and dead space lowers the chance of sepsis and other complications.

While multiple bodies 15 are used for a segmented body 13 and such a segmented body 13 is contemplated for the various embodiments disclosed herein, a non-segmented body (i.e., a body 13 that is a continuous, single-piece body 13 as opposed to being formed from multiple bodies 15) is also contemplated for most, if not all of the embodiments disclosed herein pertaining to various distal and/or proximal anchors such as, for example, those similar to the proximal and distal anchors depicted in the various figures as 50 and 900. An example of a non-segmented body 15 is depicted in FIGS. 1E and 1F. Such embodiments will may have a single porous body 15 forming the porous non-segmented body 13.

In one embodiment, one or more of the porous bodies 15 of the device 5 may be a compressed open cell polymer and may be made of any synthetic or natural biodegradable, resorbable, biocompatible polymer, such as collagen, hyaluronic acid and polyglycolic acid ("PGA"). The biodegradability allows for degradation at a specified rate that matches the rate of tissue ingrowth and fistula tract healing, such that by the time the fistula tract is healed, the material is completely absorbed by the body. It should be noted that the fistula tract may heal before the material is completely absorbed by the body. That is, the degradation rate of the device does not match, or is slower than, the rate of tissue ingrowth and fistula tract healing. It should also be noted that a mixture of different biodegradable polymers may also be utilized.

Expansion of the bodies 15 within the tract 10 provides a porous scaffold to the fistula tract and may partially or entirely stop the flow of bodily fluids through the tract. The scaffold provides a matrix that may promote tissue in-growth allowing the fistula to close. The incorporation of an antimicrobial agent, such as silver, in the porous bodies 15 or in the insertion methodology may also be incorporated to actively prevent infection and/or sepsis formation and aid in the healing of the tract. The porous bodies 15 may include wound-healing agents, such as growth factors. In some embodiments, the porous bodies include fibrosis-promoting agents.

The porous body may be adapted and configured to expand after placement in the fistula tract and absorb fluid thereby approximating closely the tract intra-luminal walls. The porous body may include a porous resorbable open cell polymer foam adapted to expand and serve as a scaffold for tissue growth and closure of the fistula tract.

In one embodiment, the porous body comprises collapsed or compressed pores, adapted and configured to increase in size after placement in a fistula tract, thus filling the fistula tract. In some embodiments, the pores of the bodies are of a reduced size, which is advantageous. For example, the pore size may vary from 5 to 1000 microns in size with an overall porosity of 25-95%. In one embodiment, bodies with a controlled pore size of between approximately 50 microns and approximately 100 microns may be used. A body with a controlled pore size, that is, a body without a broad distribution of pore sizes, may promote greater angiogenesis, which, in turn, may promote better wound-healing. Examples of materials that may provide some or all of the controlled pore size and porosities include various biomaterials manufactured by Kensey Nash Corporation, CollaPlug or other collagen products as manufactured by Integra Corporation, and STAR materials as manufactured by Healionics Corporation.

In one embodiment, the fluid permeability (i.e., porosity or pore size) of the bodies 15 may increase from the distal end of the device 5 to the proximal end of the device 5. For example, a first body 15 at the distal end of the device 5 may have a lower fluid permeability than other bodies 15 of the device 5. That is, in a segmented body 13, a most distal body 15 or the most distal several bodies 15 (i.e., the single body 15 or the few multiple bodies 15 in closest proximity to the distal end of the tract, e.g., at the bowel end of the tract) may have a lowest fluid permeability and the bodies 15 extending proximally away from the most distal body 15 may have a higher fluid permeability. In some embodiments, the fluid permeability of the bodies 15 proximal of the most distal body or bodies 15 may increase from body to body moving in the proximal direction. A most distal body 15 or bodies 15 with a lowest fluid permeability may further enhance occlusion of the distal end 12 of the fistula tract 10 and prevent unwanted fluid from the bowel from entering the fistula tract. The bodies 15 proximal of the most distal body 15 or bodies 15 may have a higher fluid permeability to permit drainage of fluids accumulating in the tract and to promote tissue ingrowth to facilitate healing of the fistula tract.

In a non-segmented body 13, the single, continuous body 15 forming the non-segmented body 13 may have a fluid permeability (i.e., porosity or pore size) that changes along the length of the single, continuous body. For example, the distal portion of the single, continuous body 15 forming the non-segmented body 13 may have a lower fluid permeability as compared to the fluid permeability of the proximal portion of the single, continuous body 15.

The porous bodies 15 may be in the form of polymer members that are anisotropic. For example, in one embodiment, the polymer members 15 may be anisotropic such that they have substantial radial expansion, but minimal, if any, longitudinal expansion.

In one embodiment, the porous bodies 15, when in a compressed or non-expanded state, have a volume that is significantly less than the volume of the bodies 15 when in a non-compressed or expanded state. For example, in one embodiment, the compressed or non-expanded volume of the bodies 15 will be between approximately 10% and approximately 60% of the non-compressed or expanded state volume. In one embodiment, the compressed volume will be between approximately 20% and approximately 25% of the expanded volume. As a result, the bodies 15 may expand between approximately four and approximately five times their compressed volumes when expanding from a compressed state to an expanded state. For example, a body 15 with a porosity of 80% can be compressed to 20% of its expanded state. In other words, the body 15 may expand approximately five times its compressed volume when expanding from a compressed to a non-compressed state. The body 15 may expand even more if it retains any absorbed fluid from the fistula tract 10.

The porous bodies 15, when in a compressed or non-expanded state, may be easier to insert in the fistula tract 10 and may cause less damage upon insertion due to the reduced size. The compressed porous bodies 15 also allow controlled expansion. In other words, the expanded size of the compressed porous body 15 is generally known and may be chosen and optimized based upon the configuration of the fistula tract 10. Thus, use of a compressed porous body 15 may permit greater occlusion of the fistula tract 10 because the compressed porous bodies 15 conform to the tract 10 as opposed to making the tract 10 conform to the body of the device, as in prior art devices. The porous bodies 15 also do not require fluid to cause expansion or maintain the body 15 in an expanded state. Such controlled expansion porous bodies 15 may be formed of hyaluronic acid, hyaluronic acid mixed with collagen, or other materials as listed in this detailed disclosure offering control or specific pore size or porosity.

In one embodiment, the controlled expansion of the bodies 15 is a function of precompressing the bodies 15 a certain extent (e.g., approximately 80 percent of its non-compressed state) and then releasing the bodies 15 to resume their non-compressed state. Thus, it is possible to readily determine the final fully expanded condition of the bodies 15 because they will only expand to their non-compressed state upon being released to resume the non-compressed state.

As mentioned above with respect to FIG. 1A, the porous bodies 15 of the device 5 may be operably connected by a connecting member 20. The connecting member 20 may be a bioresorbable and biocompatible filament or string. In some embodiments, the connecting member 20 may also be a filamentous string, which enables the decoupling of the plurality of porous bodies 15 from the connecting member subsequent to implantation of the device 5 in the tract 10.

As mentioned above with respect to FIGS. 1A and 1B, in one embodiment, the device 5 includes at least two porous bodies 15 which are adapted and configured to work together to form the device's overall body 13 and separately to allow the device body 13 to conform to the tract 10 and fill all of the tract voids. In other words, the bodies 15 are separate individual bodies joined together via the connecting member 20 along the length of the device 5 such that the resulting device body 13 has a segmented configuration. In one embodiment, when the bodies 15 are in an expanded state or even in a non-expanded state, the spaced-apart distances D, D' may be zero such that the proximal and distal ends 25, 30 of adjacent bodies 15 abut. In such an embodiment, the bodies 15 appear to form a generally continuous porous device body 13 that is segmented by the interfaces of the adjacent proximal and distal ends 25, 30 of adjacent bodies 15. Thus, regardless of the magnitude of the spaced-apart distances D, D', in one embodiment, the device body 13 can be considered to be a chain or series of individual porous bodies 15 configured to work together and separately, resulting in an overall body 13 of the device 5 that is segmented and capable of conforming to the tract 10. It should be noted that the device 5 does not stent open the tract 10, but rather, the device 5, when in an expanded or non-compressed state, is capable of conforming to the tract 10

In some embodiments, the device 5 will be configured to fill multi-tract fistulas. For example, the device 5 may have multiple device bodies 13 joined together at a common point of the device 5. In other words, the device may have at least two chains of porous bodies 15 joined together to allow a segmented device body 13 to be inserted into each of the tracts 10 of a multi-tract fistula. Alternatively, at least two chains of porous bodies 15 may be joined together to create a device 5 with at least two segmented device bodies 13.

Figure 13A:
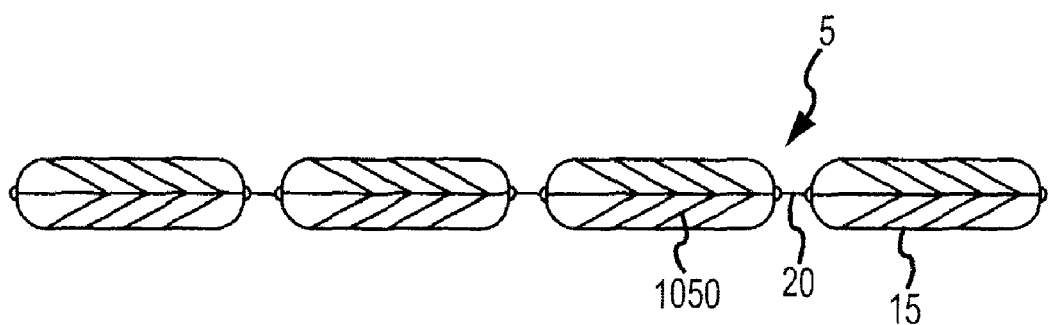
FIG. 13A depicts a fistula closure device in a non-expanded state and having bodies with engagement features.
Figure 13B:
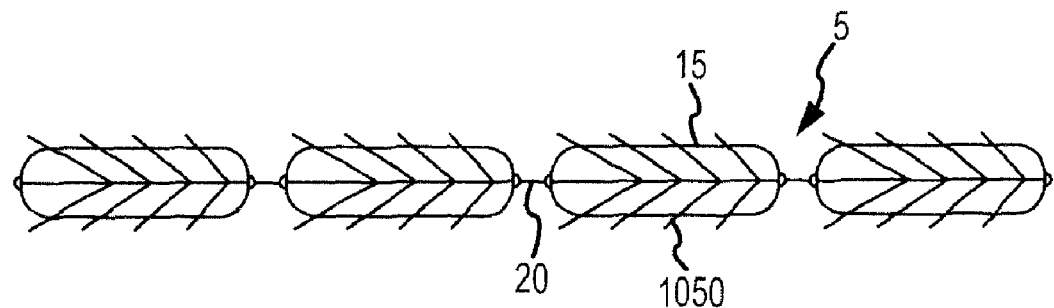
FIG. 13B depicts a fistula closure device of FIG. 13B in an expanded state with the engagement features projecting from the bodies.

As can be understood from FIGS. 13A and 13B, in some embodiments, the porous bodies 15 may also include attachment members 1050 that are configured to attach and engage the bodies 15 with the tract 10. The attachment members 1050 deploy when the bodies 15 are in a non-compressed or expanded state. The attachment members 1050 may be unidirectional (e.g., comparable or similar to a fish hook barb or have a compressed fishbone-like structure and may be made of any biocompatible, resorbable material). The attachment members 1050 permit outward removal but not inward traction. That is, when the attachment members are deployed, the bodies 15 may be retracted towards the proximal end without damaging the fistula tract 10, but the bodies 15 are engaged with the tract 10 such that they will not migrate towards the distal end 12 of the tract 10.

Figure 8A:
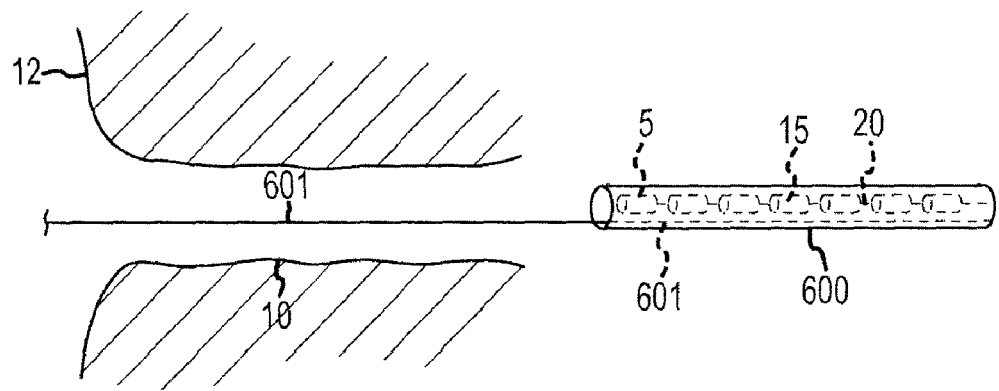
FIG. 8A is a side view of one embodiment of a delivery device for the implantable fistula closure device disclosed herein, wherein a portion of the delivery device is inserted into a fistula tract.
Figure 8B:
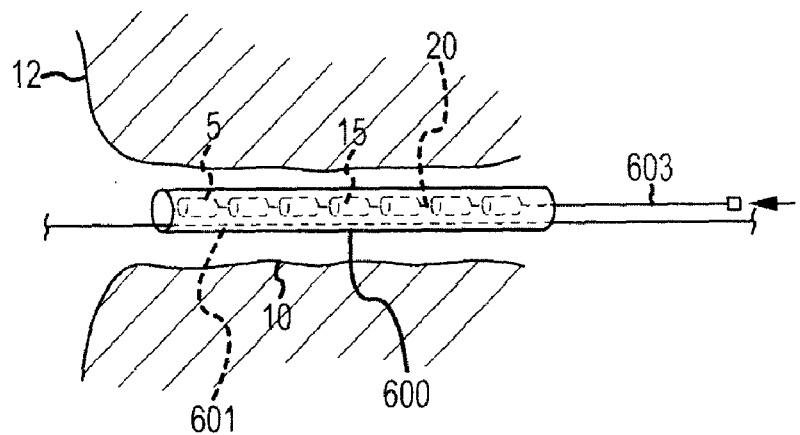
FIG. 8B is the same view as FIG. 8A, except the entire delivery device is shown inserted into the fistula tract.

As can be understood from FIG. 8B, in one embodiment, the device 5 may be deployed from the lumen of a delivery sheath 600 via a long, flexible rod or a "pusher" 603. The pusher 603 may be inserted through the delivery device 600 and may enable the clinician to push or otherwise direct the segmented device body 13 into the tract 10, thereby minimizing the dead space or void that may be left between the individual segments of the device body 13 or between the body 13 and tract 10. In some embodiments, the porous bodies 15 may not be connected via a connecting member 20, but instead may be multiple free bodies 15 that are inserted into the lumen of the sheath 600 for delivery into the tract. Thus, a pusher may enable the clinician to push or otherwise direct the unconnected bodies 15 into the fistula tract 10.

Figure 12A:
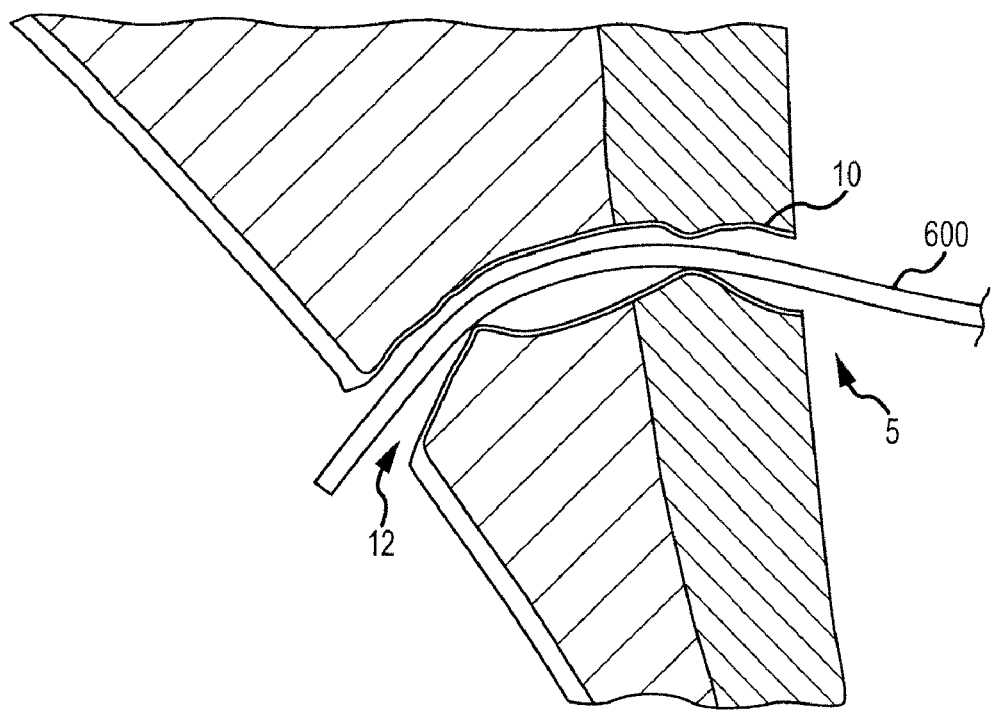
FIGS. 12A-12F are isometric views of the fistula closure device illustrating one embodiment of a method of treating a fistula.
Figure 12B:
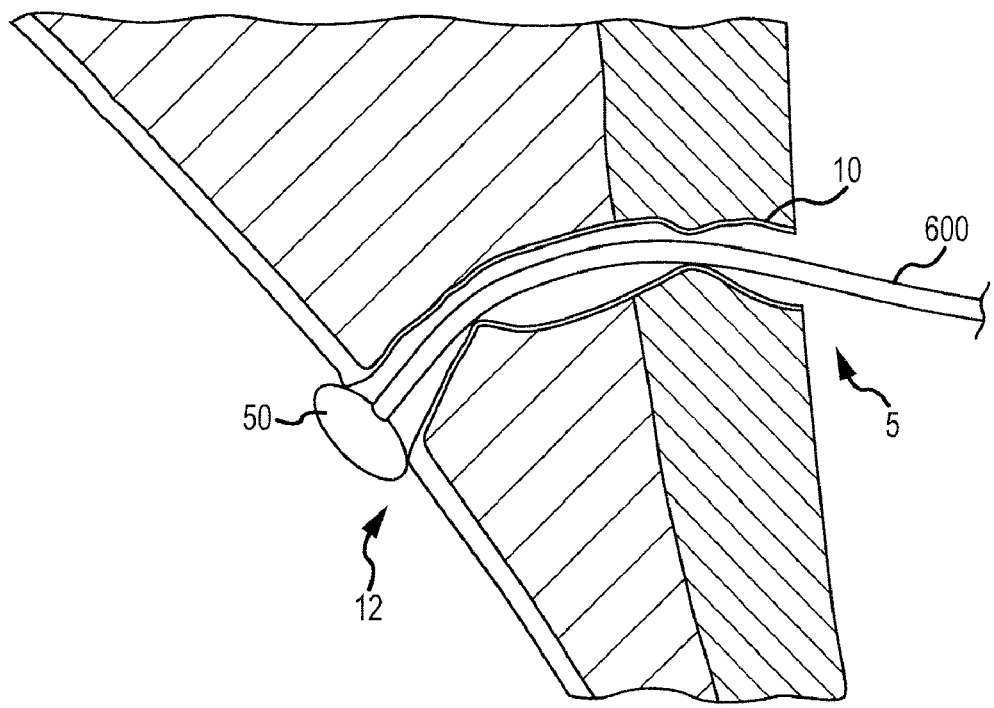
Figure 12C:
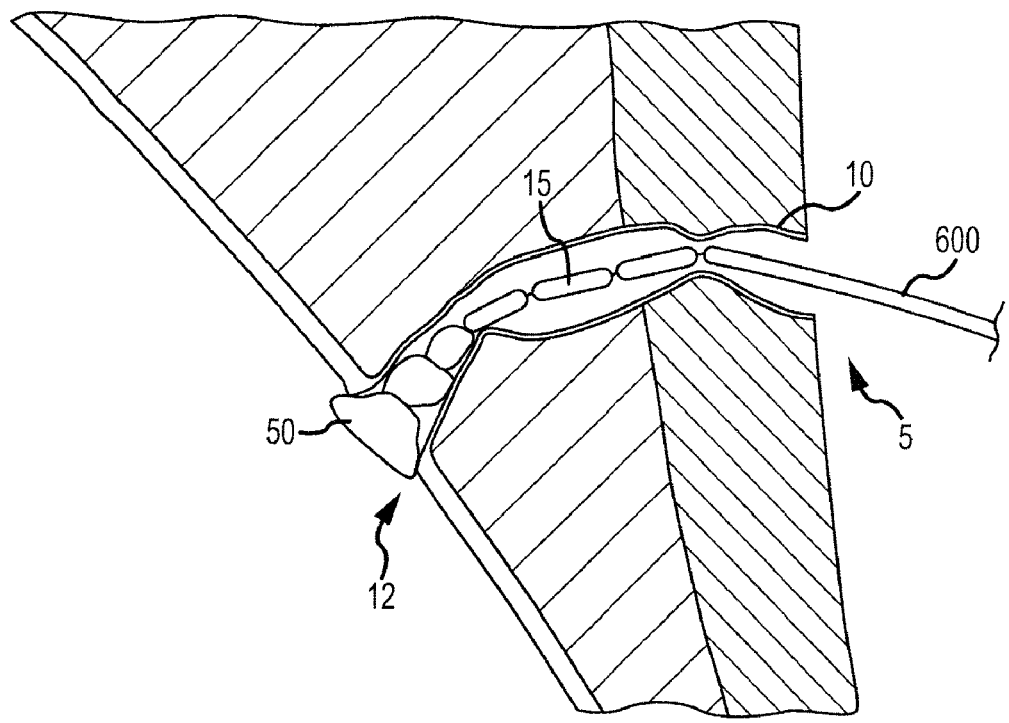
Figure 12D:
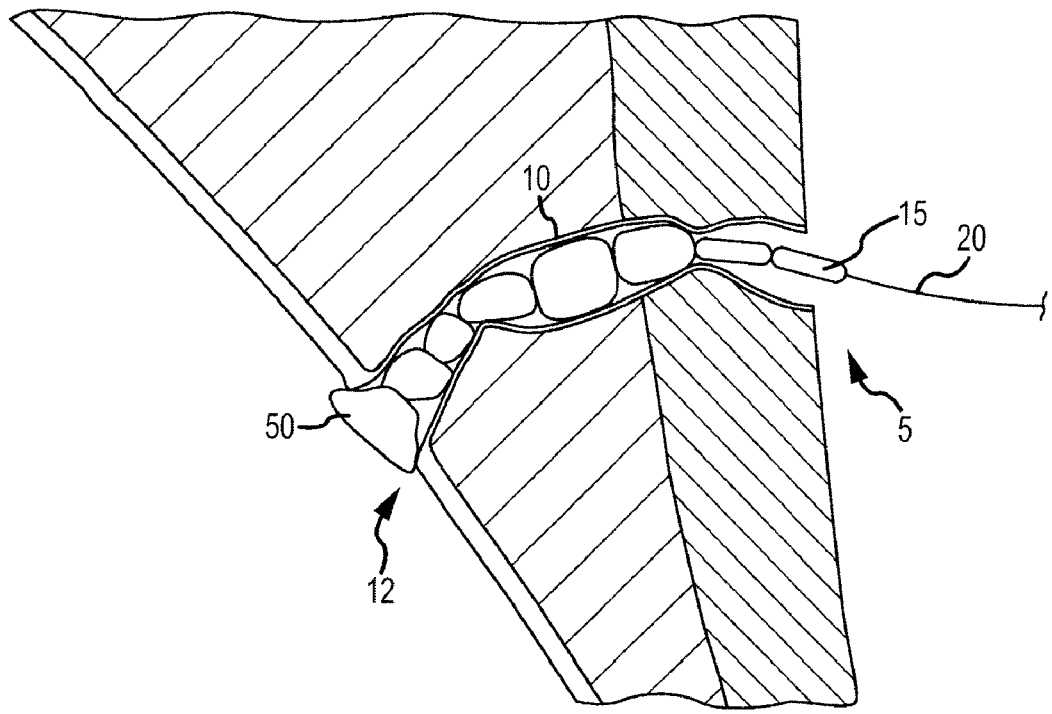
Figure 12E:
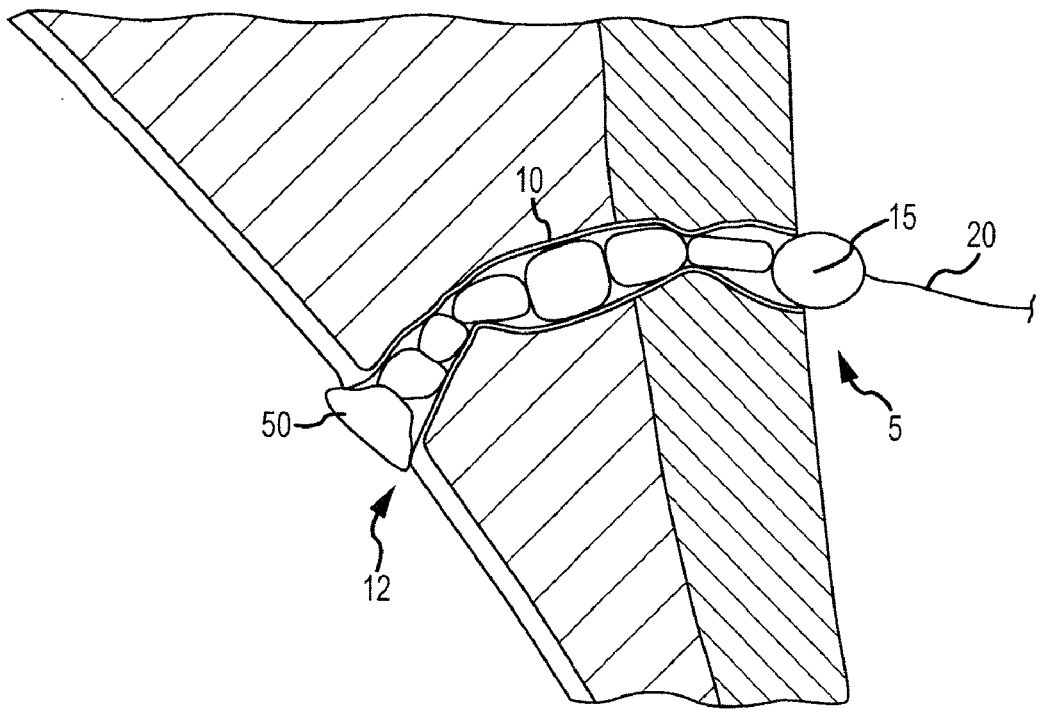
Figure 12F:
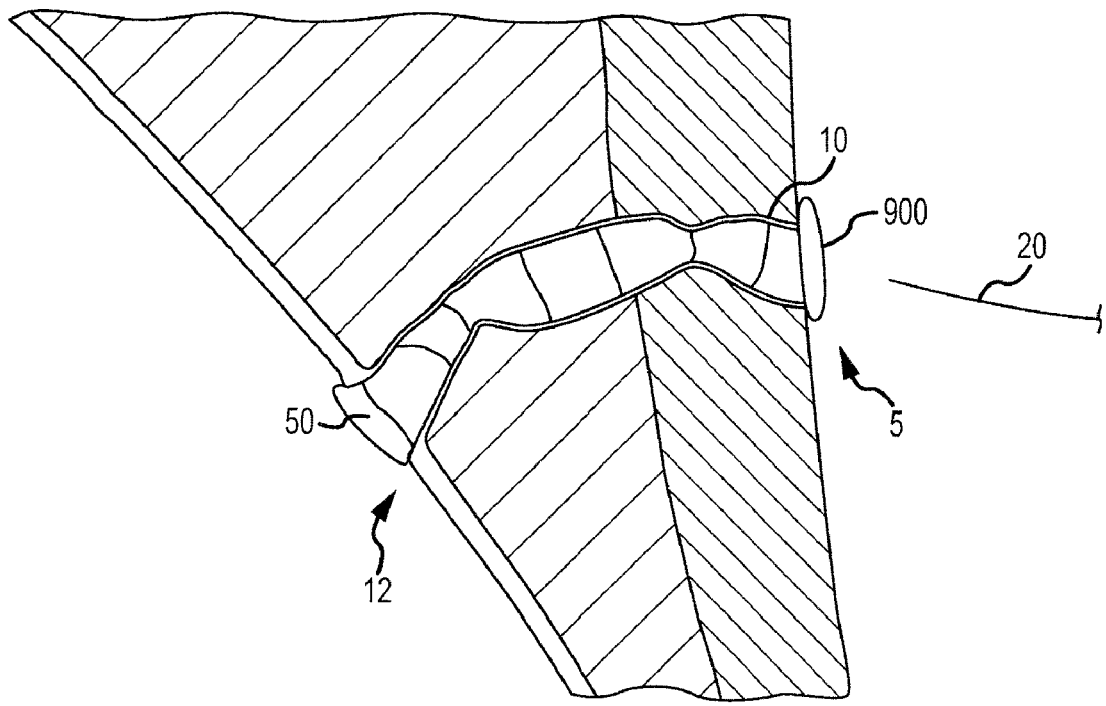

In one embodiment, as illustrated in FIGS. 12A-12G, the device 5 is loaded in a lumen of a catheter, sheath or guidewire. As can be understood from FIGS. 12A-12B, the loaded catheter, sheath or guidewire 600, 601 is then inserted into the tract 10 and then, as shown in FIG. 12C, withdrawn from about the device body 13 to leave the device body 13 within the tract 10. As indicated in FIGS. 12C-12F, the device body 13 then expands to fill and occlude the tract 10. As illustrated in FIG. 12F, and as described in more detail below, the proximal end of the tract 10 may include a proximal clip 900 to further secure the device 5 in the tract 10.

Figure 8C:
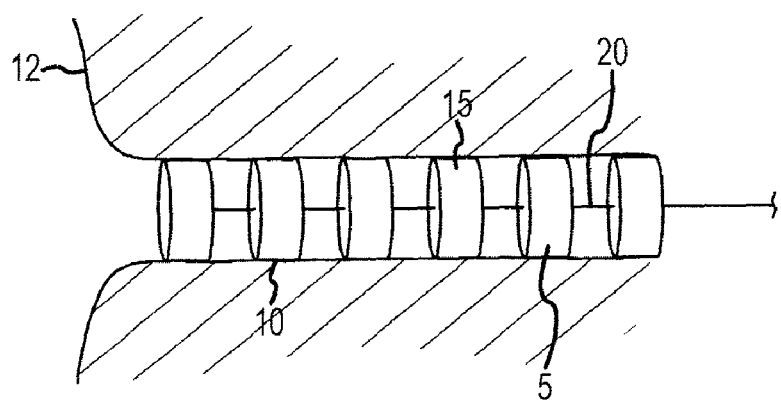
FIG. 8C is the same view as FIG. 8A, except the delivery device is withdrawn from about the device body and the device body is fully expanded.

In another embodiment, as shown in FIGS. 8A-8F, the catheter or sheath may be a dual lumen catheter 600, where one lumen contains the device 5 and the other lumen contains a guidewire 601. In one embodiment, the catheter may be a multi-lumen catheter where at least one lumen is shaped like a "D". As can be understood from FIGS. 8A-8B, the guidewire 601 is inserted into the fistula tract 10 and the catheter 600 is tracked over the guidewire 601. As shown in FIG. 8C, the device 5 is deployed and the catheter 600 is withdrawn from about the device body 13 to leave the device body within the tract 10. The device body 13 then expands to fill and occlude the tract 10.

Figure 8D:
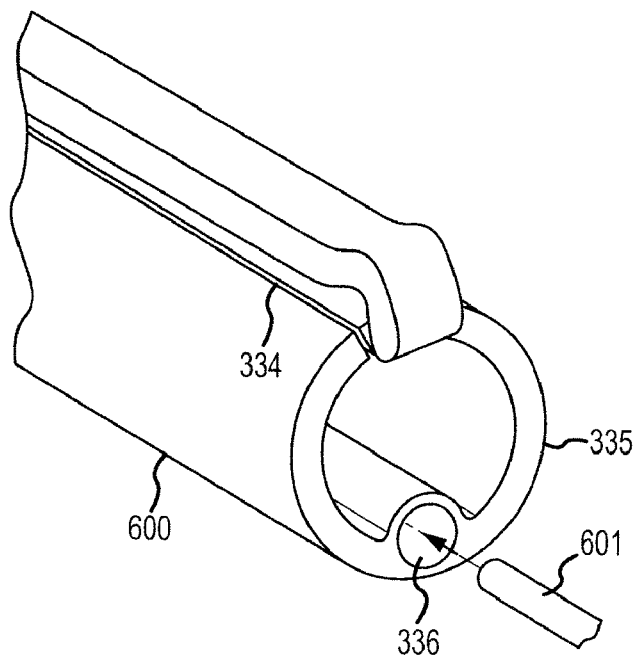
FIG. 8D is an end isometric of one embodiment of the delivery device of FIG. 8A.
Figure 8E:
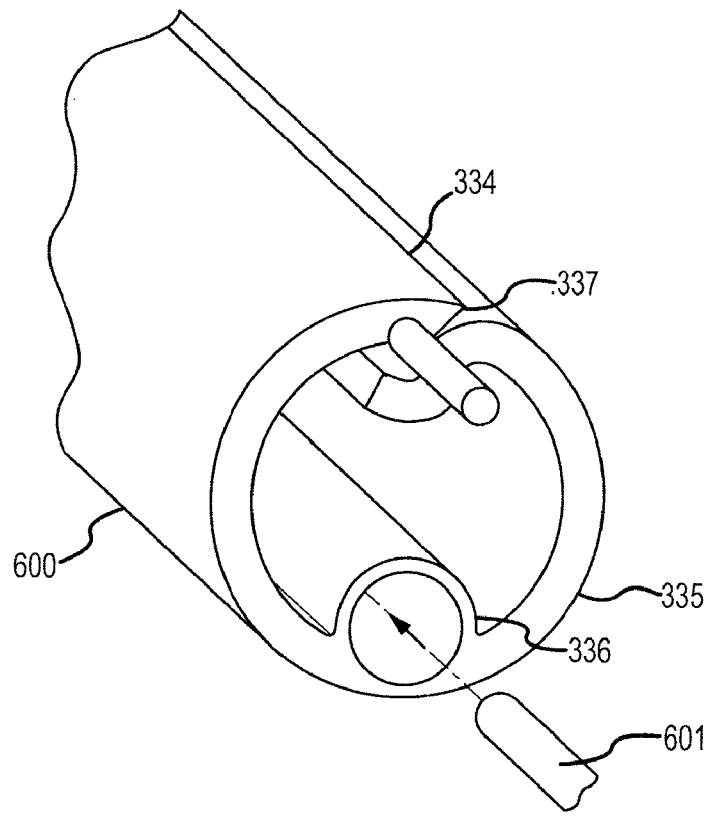
FIG. 8E is an end isometric view of an alternative embodiment of the delivery device of FIG. 8A.

As illustrated in FIGS. 8D-8E, which show various embodiments of the delivery device of FIG. 8A, the catheter 600 may be a peel away sheath. For example, a skive, score, partial cut, mechanical joint or formed groove may create a longitudinally extending stress concentration 334 for causing the catheter to peal along the stress concentration 334. As indicated in FIG. 8E, the stress concentration 334, which may be a mechanical joint, may include a grasping member 337 that may be used to exert the necessary force on the stress concentration to bring about its separation.

Figure 8F:
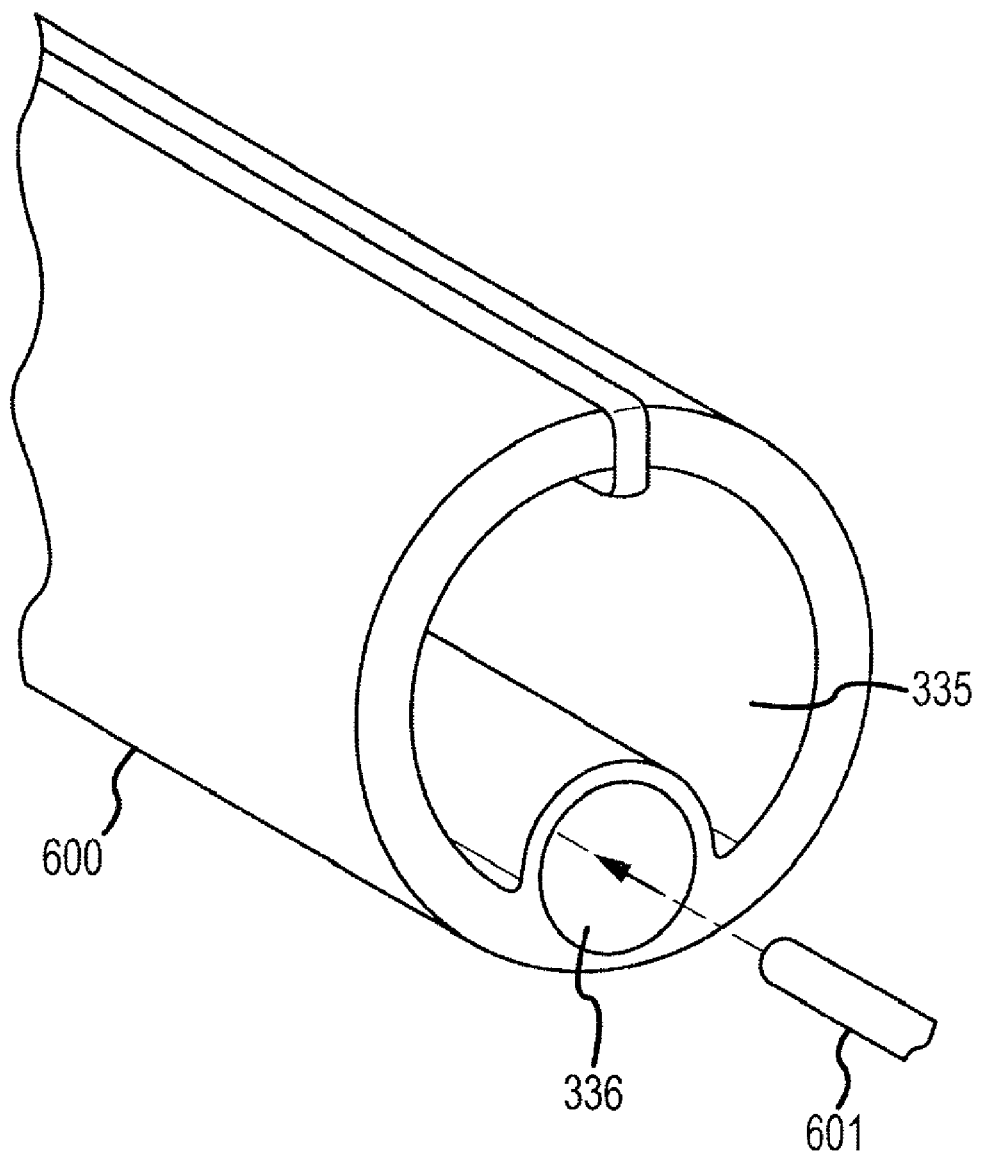
FIG. 8F is an end isometric view of another alternative embodiment of the delivery device of FIG. 8A.

The delivery devices depicted in FIGS. 8D-8F may include a central or main lumen 335 through which the fistula closure device 5 may pass and a secondary lumen 336 through which the guidewire 601 may pass.

As can be understood from FIGS. 8D-8F, the delivery device 600 may be tracked over a guidewire 601 with the fistula occlusion device 5 residing in the main lumen 335. Once properly positioned in the fistula tract, the delivery device 600 can be removed from about the closure device 5. The removal of the delivery device 600 from about the closure device 5 may be accomplished by grasping an exposed portion of the delivery device 5 or a grasping member 337 (see FIG. 8E) and then pulling or pushing the delivery device relative to the closure device 5. Alternatively, a hooked member 340 having a hook or other engagement feature 341 that engages an end of the delivery device 600 may be employed where the hooked member 340 can be used to pull the delivery device 600 from about the closure device 5, as can be understood from FIGS. 8D and 8F.

Figure 9A:
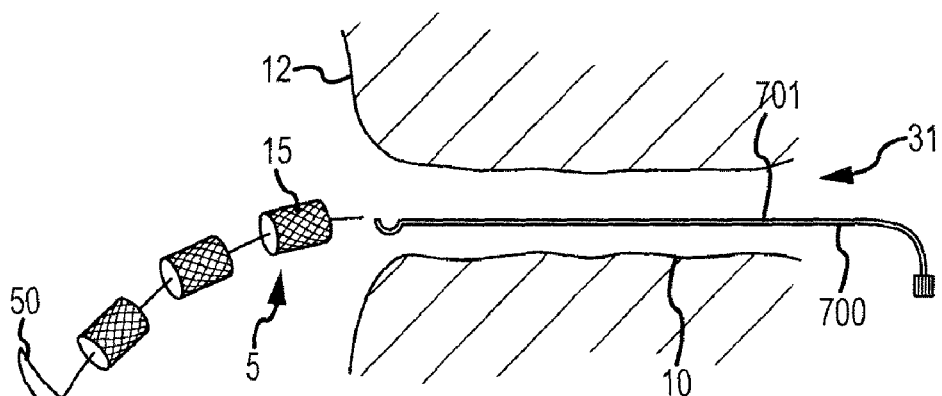
FIG. 9A is a side view of still another alternative embodiment of a delivery device for the implantable fistula closure device disclosed herein, wherein the delivery device includes a hook-like feature.
Figure 9B:
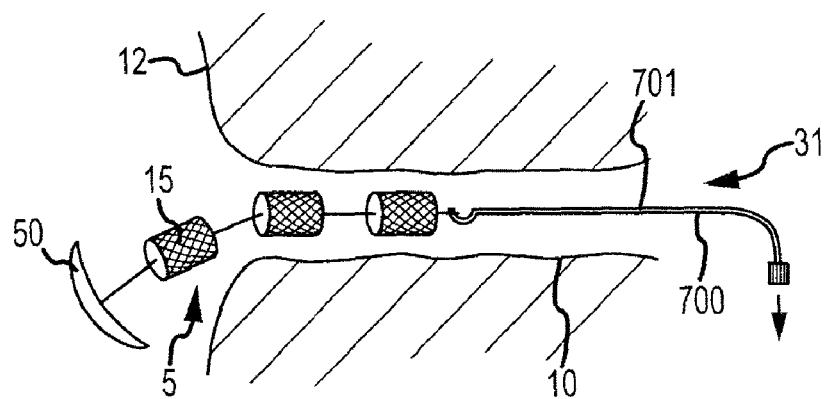
FIG. 9B is the same view as FIG. 9A, except the fistula closure device is shown partially pulled through the tract via the delivery device.
Figure 9C:
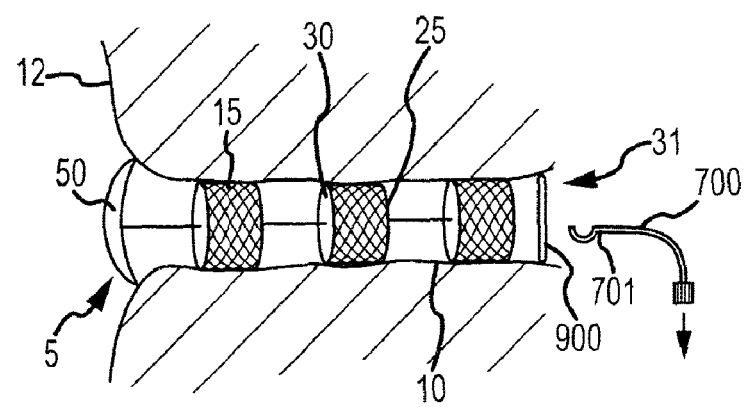
FIG. 9C is the same view as FIG. 9A, except the fistula closure device is shown pulled through the tract and the device body is expanded.

As shown in FIGS. 9A-9C, in still another embodiment, the device 5 is deployed via a guidewire 700 with a hook-like feature 701 at one end. Such a delivery device can be used for an anal fistula 10, where there is access at both a proximal and a distal end of the fistula tract 10 (in contrast to an enterocutaneous fistula, which has one external access point). The guidewire 700 with the hook-like feature 701 is inserted into the fistula tract at a first end and passed through the tract 10 such that it can be used to pull the device 5 through the tract 10 by the hook 701 to a second end. The distal end 50 of the device 5, which is already in an expanded state, anchors the device 5 into the fistula tract. This embodiment of the delivery device may reduce the amount of work required of the surgeon as the hook may be used to pull the delivery device into place. In another embodiment, a guidewire or stylet is extended through the device body 13 generally parallel to the connecting member 20. In other words the device body 13 is threaded onto the guidewire or stylet. The guidewire or stylet is then used to negotiate the device body 13 into the tract 10. Once positioned in the tract 10, the stylet or guidewire can be withdrawn from the device body 12. Where the device body 13 is threaded onto the stylet or guidewire, the bodies 15 may have holes therein for receiving the stylet or guidewire. Also, the bodies 15 may have slots through their sides that lead to the holes so the stylet or guidewire can be inserted into the holes without having to be placed therein via a threading motion. In versions of such embodiments, the slots and/or holes in the bodies 15 for receiving the stylet or guidewire in a threaded arrangement are configured to close after the stylet or guidewire is withdrawn from the bodies 15. The closer of the slots and/or holes may result from the expansion of the bodies 15.

Figure 9D:
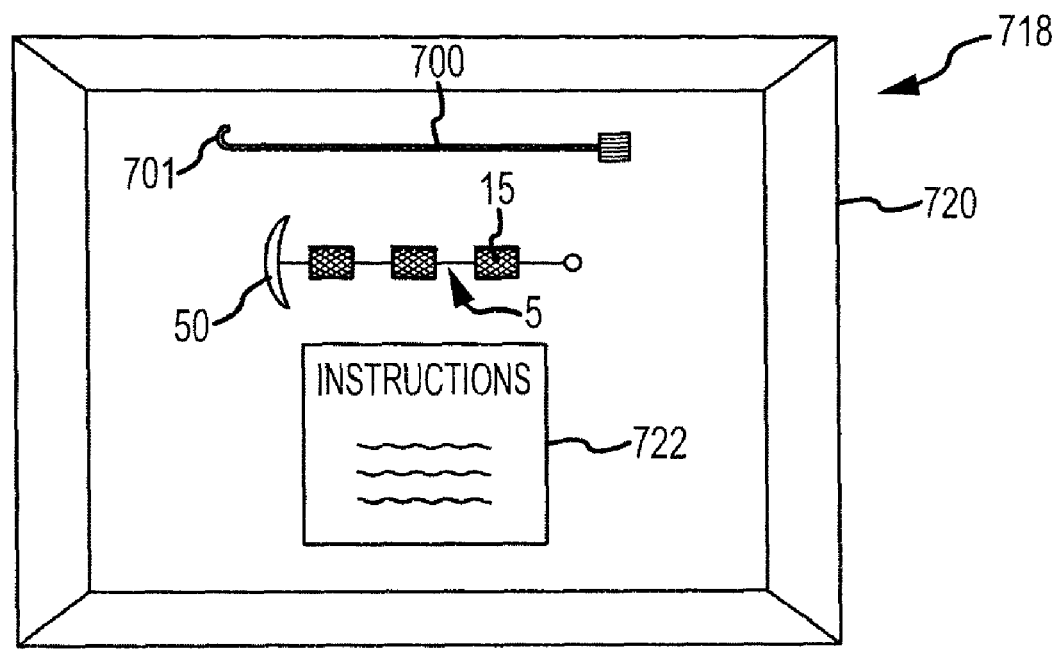
FIG. 9D is a depiction of a medical kit for closing a fistula and, in some embodiments, containing at least some of the components depicted in FIGS. 9A-9C.

As can be understood from FIG. 9D, the embodiment described with respect to FIGS. 9A-9C can be provided as a kit 718 wherein the delivery tool 700 and the fistula closure device 5 are provided in a sterile package 720. Instructions 722, which may be provided on or with the kit 718, or alternatively via the internet or another indirect method, provide direction on how to employ the kit. The instructions may outline a deployment method similar to that described immediately above.

Regardless of whether a catheter, sheath, guidewire or stylet or combination thereof is used to deploy the device 5 in the tract 10, once located within the tract 10, the device body 13 will begin to expand and fill the voids of the tract 10. Expansion of the bodies 15 may be a result of being free of the constraints of the lumen of the sheath, catheter or guidewire used to deliver the device 5. Expansion of the bodies 15 may be a result of being free of the constraints of a restraining mechanism such as a biodegradable ring, sheath, member, etc. extending about the bodies 15 when first deployed in the tract 10. Expansion may be a result of being exposed to body fluids or temperature within the tract 10. Expansion may be a result of any one or more of these aforementioned expansion methods.

As can be understood from FIG. 1B, the porous bodies 15 at the proximal and/or distal ends 31, 32 of the device 5 may be configured to protrude from the distal and/or proximal fistula openings when implanted in the fistula tract 10. As depicted in FIG. 1B, the protruding end 115 of the most distal body 110, or the entirety of the most distal body 110, may be configured to expand more than the rest of the porous bodies 15. Such an over-expanding capability at the distal ends 32 of the device 5 when within the fistula tract may produce an occluding and anchoring effect. Additionally or alternatively, the same concept may be applied to the most proximal body 15 at the device proximal end 31. Such embodiments can be considered to have at least one body 15 with a magnitude of expansion that is different from (i.e., exceeds) the magnitude of expansion of the other bodies 15. In one embodiment, a device 5 with a distal most body 110 that is configured to have increased expansion as compared to its fellow bodies 15 will be positioned in the tract 10 such that the most distal body 110 is partially within the tract 10 and partially extending from the distal opening 12 into, for example, the bowel lumen. Thus, as illustrated in FIG. 1B, once the distal portion of the device 5 is in place, the distal most body 110 of the device 5 expands to contact the edges of distal opening 12 of the fistula tract 10, thereby occluding the distal opening 12 of the fistula tract 10. The device 5 also expands to fill the rest of the fistula tract 10. To facilitate a generally complete sealing of the distal opening 12, the distal most body 110 of the device 5 may include an impermeable coating.

In a manner similar to that discussed above with respect to the distal most body 110, the proximal most body at the proximal end 31 of the device 5 may be adapted and configured to anchor or otherwise hold the device 5 in place within the fistula tract. Where both the distal and proximal most bodies are so configured, the distal and proximal most bodies will provide a counter force or counter balance to each other through the connecting member 20. In some embodiments, the proximal most and/or distal most bodies may be or include an adhesive layer to further strengthen the seal around the respective fistula tract openings.

Figure 1C:
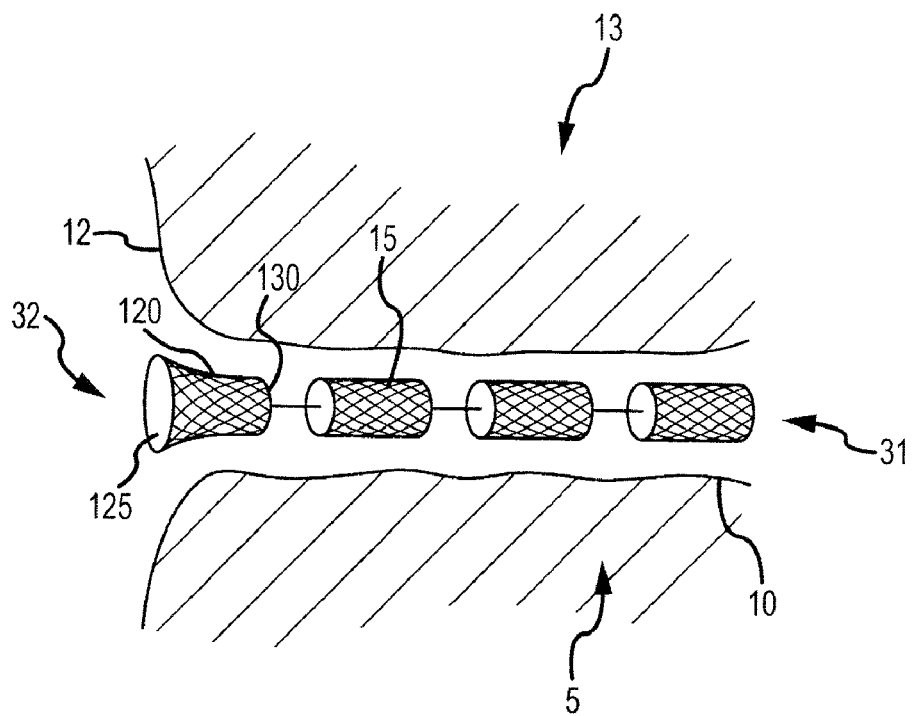
FIG. 1C is an isometric view of the implantable fistula closure device located in a fistula tract in a compressed or non-expanded state, wherein the distal most body of the device body has a conical shape, as opposed to a cylindrical shape.
Figure 1D:
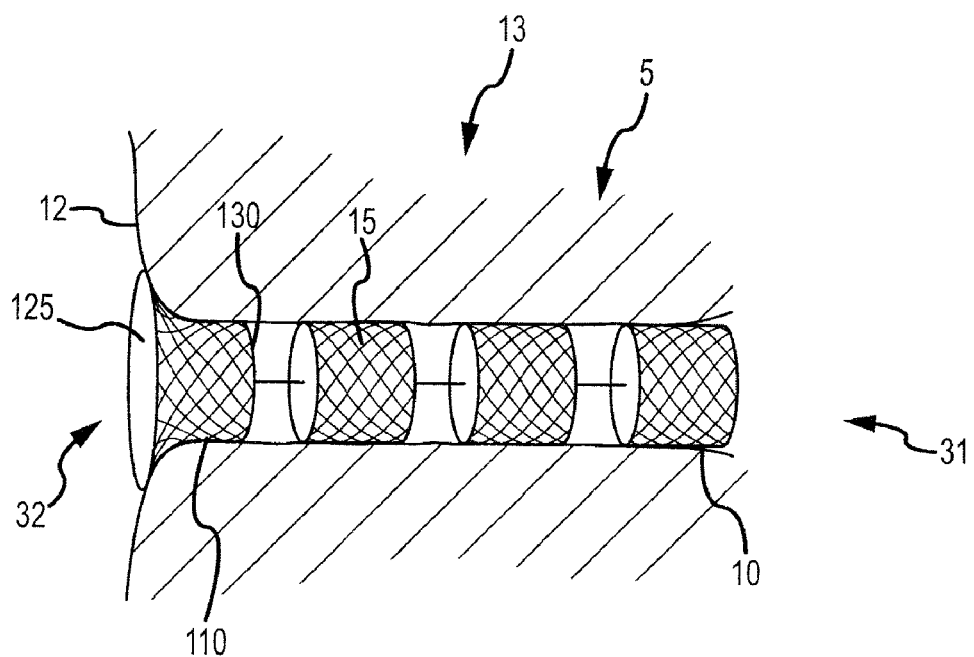
FIG. 1D is the same view as FIG. 1C, except the implantable fistula closure device is in a non-compressed or expanded state within the fistula tract.
Figure 1E:
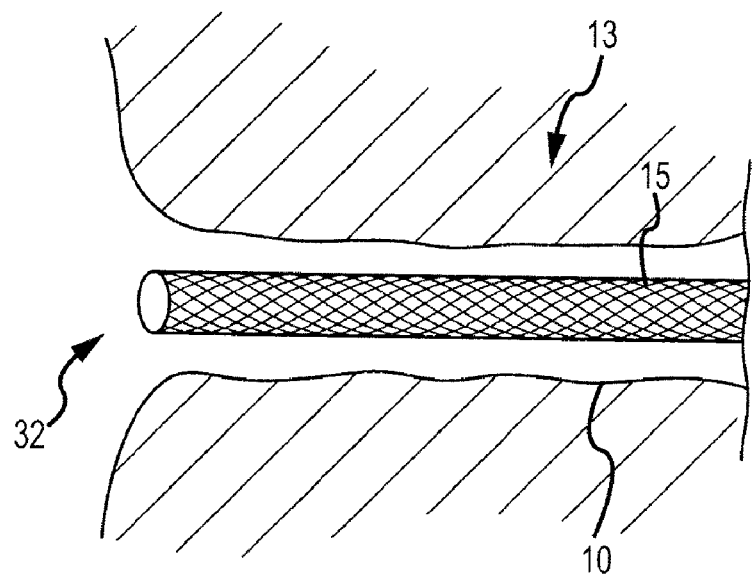
FIG. 1E is an isometric view of an implantable fistula closure device having a non-segmented body and located in a fistula tract in a compressed or non-expanded state.
Figure 1F:
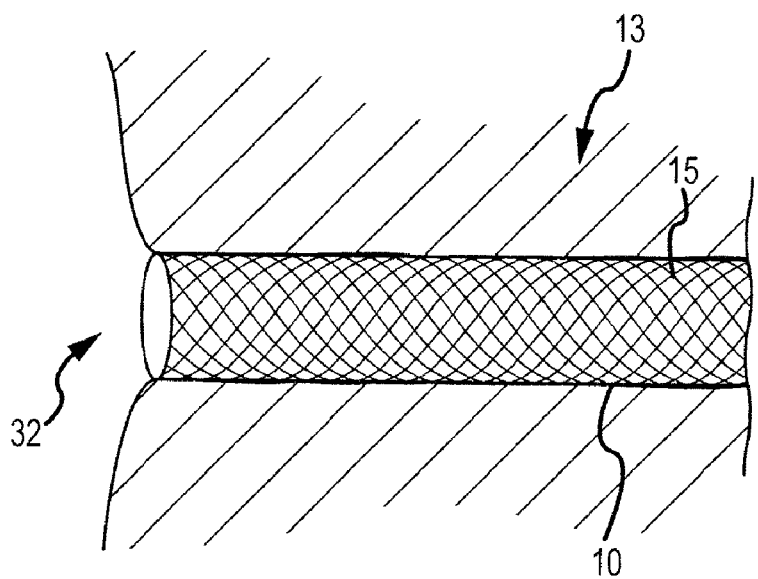
FIG. 1F is the same view as FIG. 1E, except the implantable fistula closure device is in a non-compressed or expanded state within the fistula tract.

For a discussion of distal most or proximal most bodies 15 having shapes other than generally cylindrical, reference is made to FIGS. 1C and 1D, which are respectively the same as FIGS. 1A and 1B, except illustrating the differently shaped bodies 15. As shown in FIGS. 1C and 1D, the distal most body 120 may have a shape that is non-cylindrical and, more specifically, conical. The proximal most body 15 at the proximal end 31 of the device 5 may also have a conical shape as opposed to a cylindrical shape.

In some embodiments, the conically shaped most distal body 120 is generally shaped such that its distal end 125 is generally greater in diameter than on its proximal end. The distal end 32 of the device 5 may be advanced into the distal opening 12 of the fistula tract 10 such that a distal portion 125 of the body 120 extends from the tract opening 12 into, for example, the bowel lumen. As illustrated in FIG. 1B, once the distal end of the device 5 is in place, the distal end 125 of the body 120 expands to contact the edges of the distal opening 12 of the fistula tract 10, thereby occluding the distal opening 12 of the fistula tract 10. The rest of the device body 13 also expands to generally fill the rest of the fistula tract 10 as described above. In some embodiments, the proximal end 31 of the device 5 does not extend beyond the edge of the fistula tract, while in other embodiments it does.

In some embodiments, the difference in diameter of the distal end 125 could be a result of a difference in the distance by which the different parts of the distal body 120 can expand. For example, the diameter of the cylinder in the compressed or non-expanded state is uniform, however when the cylinder expands, the proximal end of the cylinder may reach the wall of the fistula tract 10, but the distal end may have a greater distance to expand before reaching the wall of the fistula tract 10 which corresponds to its target area of expansion. In this case, the diameter of the cylinder in a non-expanded state is uniform, but the diameter of the cylinder in the expanded state forms a conical shape.

Figure 11A:
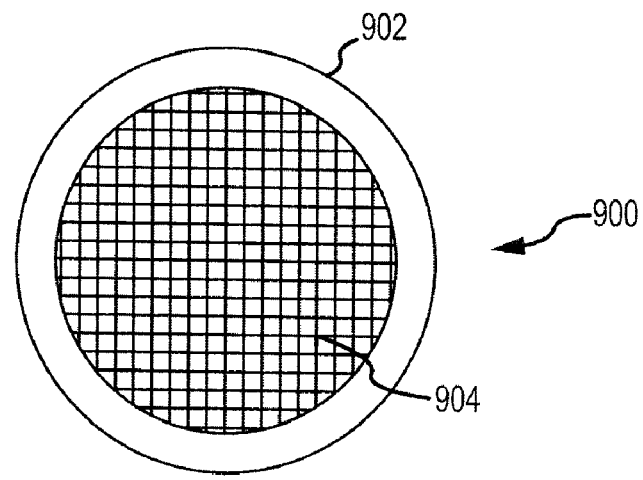
FIG. 11A is a front view of a proximal clip.
Figure 11B:
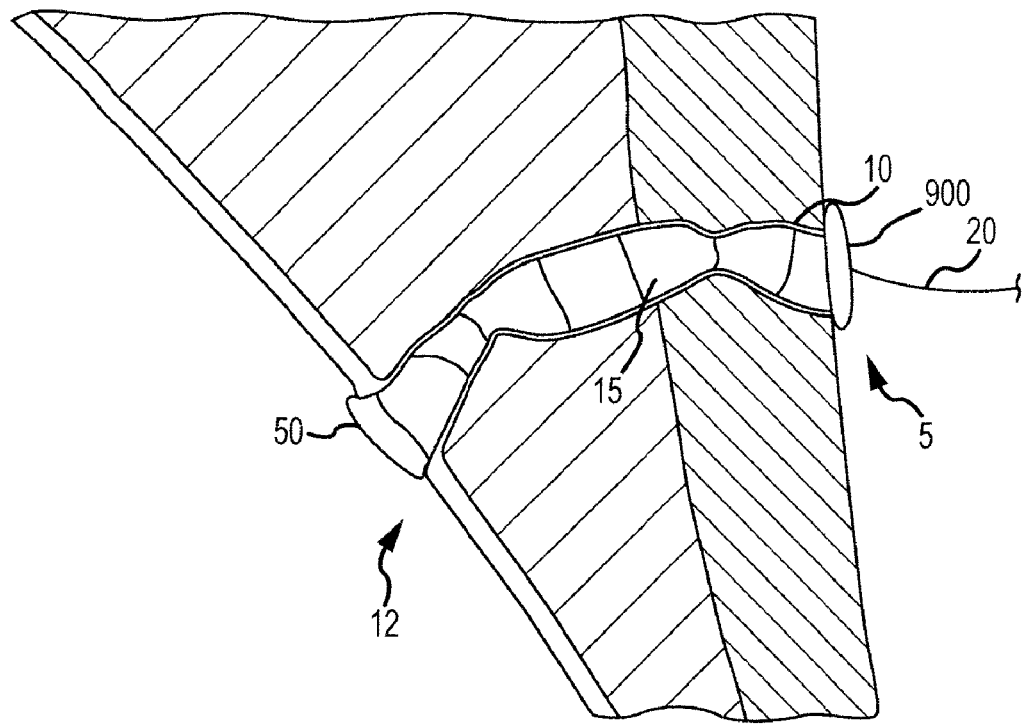
FIG. 11B is a side view of the clip of FIG. 11A.

In some embodiments of the device, as can be understood from FIGS. 11A and 11B, the proximal end 31 may be adapted and configured to receive a proximal clip 900 that secures the device 5 in place. As shown in FIG. 11A, which illustrates a front view of one embodiment of such a clip 900, the clip 900 may include an outer ring 902 and a mesh-like membrane 904 that extends across the clip 900. In one embodiment, as illustrated in FIG. 11B, which is a side view of the clip, the clip 900 is disc-shaped. In alternative embodiments, the clip 900 is a shape other than a disc, such as a polygon. The clip 900 may be made of any biocompatible material, such as PGLA, PVA or PVC or other suitable biocompatible plastic. The material may also be resorbable.

As can be understood from FIG. 11B, the clip 900 extends across the proximal end of the fistula tract 10 and is generally flush or slightly raised relative to the proximal end of the fistula tract 10. The clip 900 helps to maintain tension on the connecting member 20 that couples the expanding member 50 with the clip 900 thus helping to maintain or anchor the device 5 in the tract 10. The clip 900 may be coupled to the connecting member 20 via friction, pinching, suturing or other suitable method.

Features of the clip 900 and/or proximal end 31 of the device 5 may be transparent to allow visual inspection of the tract. In some embodiments, the clip 900 and/or proximal end of the device may be adapted to cover the proximal end of the fistula tract without completely sealing the proximal end of the tract, thereby allowing accumulating fluids to drain or escape from the proximal end of the tract. In addition, the mesh-like membrane 904 permits drainage of accumulating fluids from the proximal end of the tract. After the tract 10 heals, the proximal clip 900 will resorb or otherwise be removed.

In some embodiments, the distal end of the device body 13 may include an expandable feature 50 that may serve to anchor the device distal end in place at the fistula distal opening 12 and/or seal the fistula distal opening 12. For a discussion of a first embodiment of such an expandable feature 50, reference is made to FIGS. 2A and 2B, which are respective isometric views of the device 5 located in the fistula tract 10 and the expandable feature 50 in a non-expanded state and an expanded state.

Figure 2A:
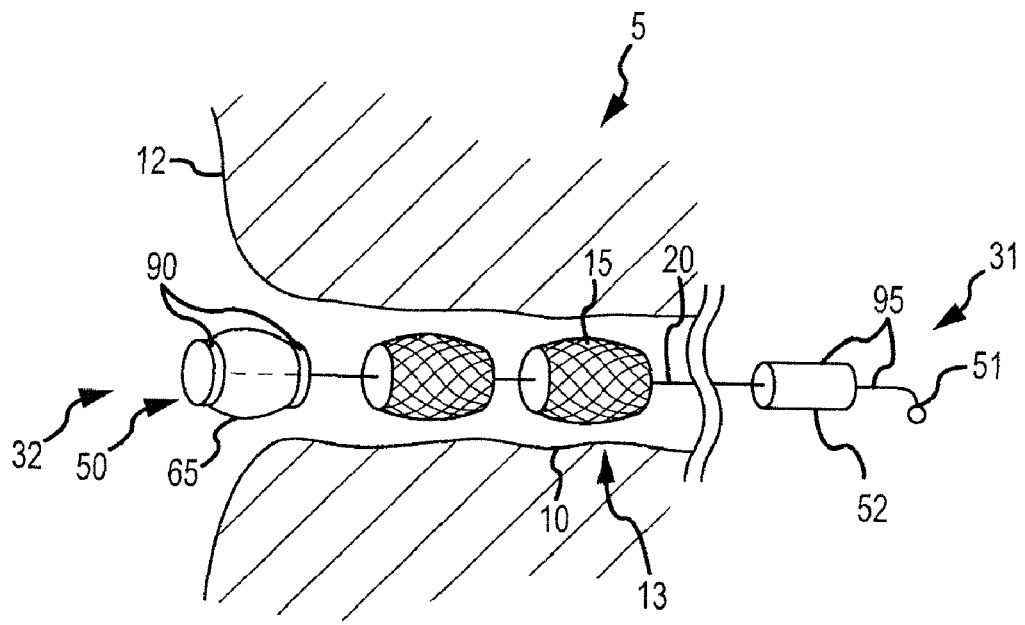
FIG. 2A is an isometric view of the implantable fistula closure device located in a fistula tract in a compressed or non-expanded state, wherein the distal end of the device includes an expanding feature in the form of a gel-filled expandable member sandwiched between discs.
Figure 2B:
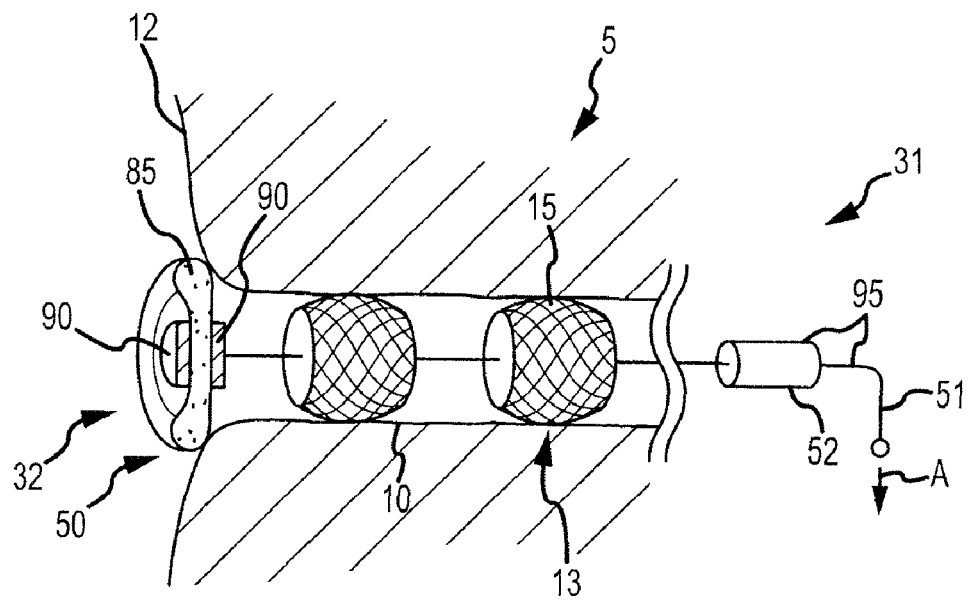
FIG. 2B is the same view as FIG. 2A, except the implantable fistula closure device and its expanding feature are in a non-compressed or expanded state.

As shown in FIGS. 2A and 2B, the device body 13 is generally the same as discussed above with respect to the embodiments depicted in FIGS. 1A and 1B such that the device body 13 includes individual porous bodies 15 coupled together via a connecting member 20. However, as indicated in FIGS. 2A and 2B, the distal end 32 of the device 5 terminates in the expandable feature 50, which is coupled to the distal end of the connector member 20. The expandable feature 50 may include a gel-filled or otherwise readily deformable member 85 sandwiched between a pair of generally rigid discs 90. An actuation mechanism 95 extends along the connector member 20 to couple with the feature 50. The actuation mechanism 95 may be filamentous or bioresorbable thread. Alternatively or additionally, the actuation mechanism may include a catheter 52 and one or more wires 51 longitudinally displaceable within lumens of the catheter 52. The catheter 52 may extend through the bodies 15 the entire length of the device 5 and terminate at or near the expandable feature 50. In some embodiments, the expandable feature 50 may expand without an actuation mechanism 95, e.g., the expandable feature expands upon exposure to body fluids or a temperature differential within the tract 10 or via its own biased nature.

The proximal end of the actuation mechanism 95 may be pulled or otherwise displaced relative to the rest of the actuation mechanism such that the actuation mechanism may cause the feature 50 to expand. For example, in one embodiment, the feature 50 is biased in a non-expanded state and pulling on the mechanism 95, as indicated by arrow A in FIG. 2A, causes the discs 90 to converge towards each other, eventually engaging each other to become fixed in the converged state, as depicted in FIG. 2B. The discs 90 converging causes the deformable member 85 to squish or deflect outward, as illustrated in FIG. 2B, thereby serving as an anchor and/or sealing the tract opening 12. The device body 13 expands to generally fill the rest of the fistula tract 10 as described above.

In another embodiment, the feature 50 is biased in an expanded state and operating the mechanism 95 forces the discs 90 away from each other to cause the feature 50 to assume the generally cylindrical configuration depicted in FIG. 2A as the device 5 is being negotiated through the tract 10. Once the feature 50 passes through the tract opening 12, the mechanism 95 can be released to allow the feature 50 to bias into the expanded state depicted in FIG. 2B. The feature 50 may then serve as an anchor and/or seal for the tract opening 12. The device body 13 expands to generally fill the rest of the fistula tract 10 as described above.

Figure 2C:
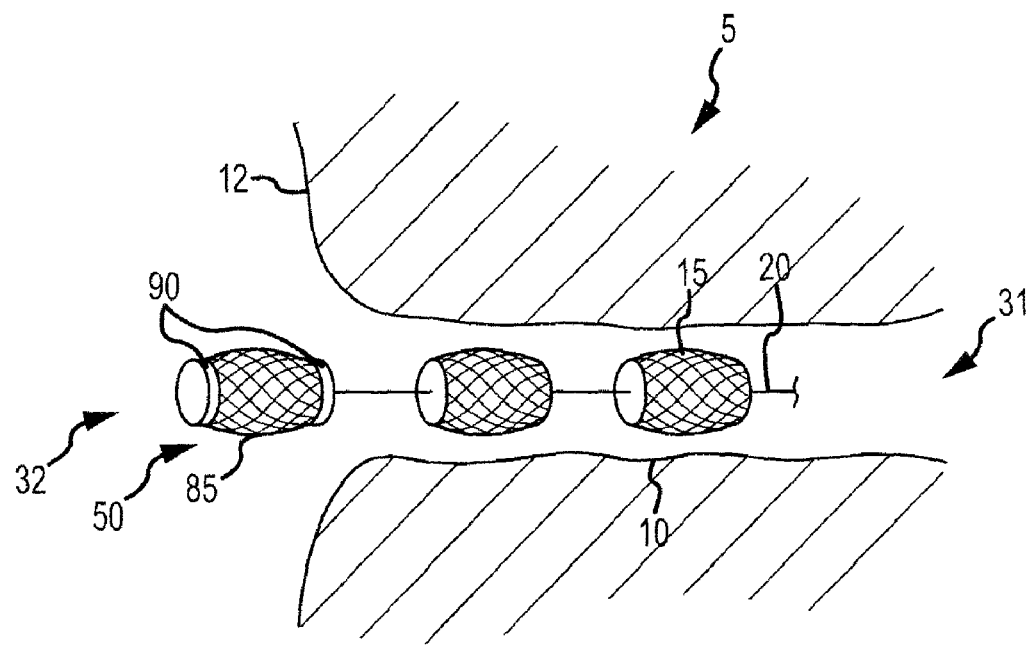
FIG. 2C is the same view as FIG. 2A, except the expanding feature includes a porous expandable member sandwiched between discs.
Figure 2D:
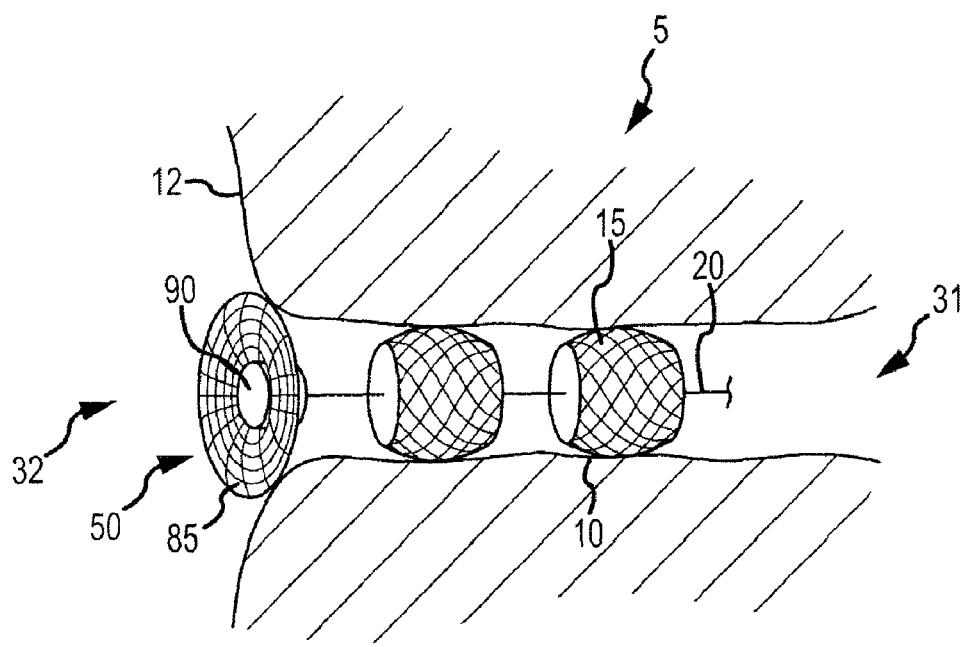
FIG. 2D is the same view as FIG. 2C, except the implantable fistula closure device and its expanding feature are in a non-compressed or expanded state.

As indicated in FIGS. 2C and 2D, which are the same respective views as FIGS. 2A and 2B, in another embodiment, the feature 50 may have the same configuration and operation as discussed above with respect to FIGS. 2A and 2B. However, the readily expandable member 85 depicted in FIGS. 2A and 2B does not have a gel-filled member 85 but instead has a porous member 85 formed from a material similar to that employed for the various bodies 15. In one embodiment, the expandable member 85 may be a super compressed collagen. Like the member 85 depicted in FIGS. 2A and 2B, the member 85 depicted in FIGS. 2C and 2D may be caused or allowed to expand laterally to serve as an anchor and/or seal, as can be understood from FIG. 2D. Expansion in the lateral direction may be advantageous in that it reduces the profile of the distal portion of the device 5 in the bowel lumen. The device body 13 expands to fill the remainder of the fistula tract 10 as described above.

In an alternative to the embodiments discussed above with respect to FIGS. 2A-2D, the expanding feature 50 may be biased to assume the biased configuration of FIGS. 2B and 2D. However, the device 5 will not employ an actuation mechanism 95 to retain the feature 50 in a non-expanded state until properly located in the fistula tract 10. Instead, the feature 50 will be maintained in the non-expanded state via the lumen walls of a catheter, sheath or guidewire employed to deliver the device 5. Once the device 5 is properly located within the tract 10, the catheter, sheath or guidewire can be withdrawn from about the device 5 to allow the feature 50 to bias into its expanded state.

Figure 3A:
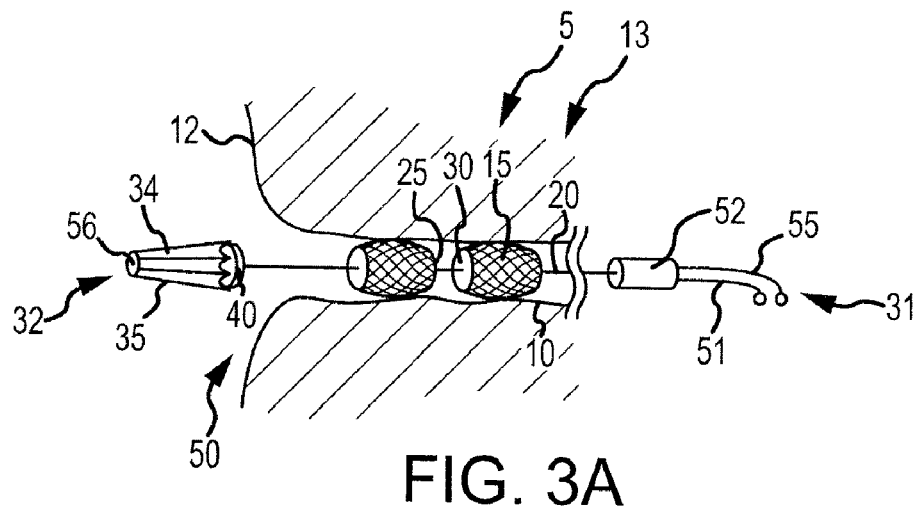
FIG. 3A is an isometric view of the implantable fistula closure device located in a fistula tract in a compressed or non-expanded state, wherein the distal end of the device includes an umbrella-like expanding feature.
Figure 3B:
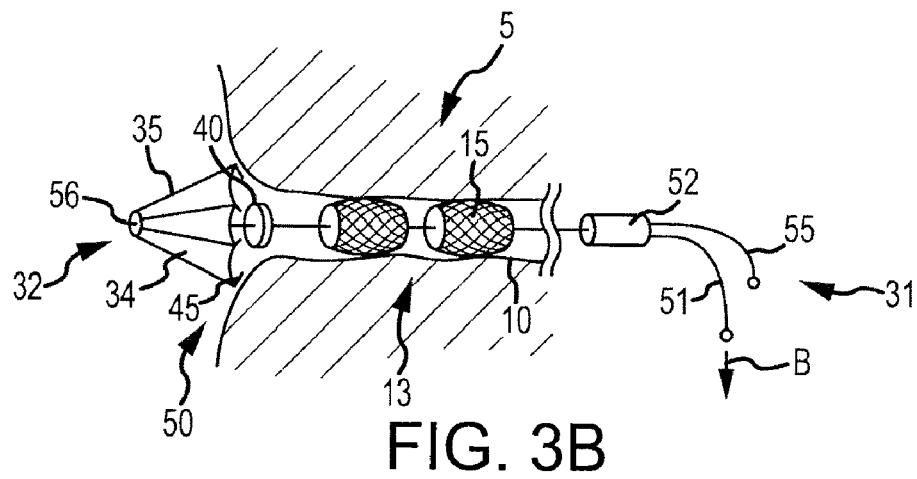
FIG. 3B is the same view as FIG. 3A, except the expanding feature of the implantable fistula closure device is in a partially non-compressed or expanded state.
Figure 3C:
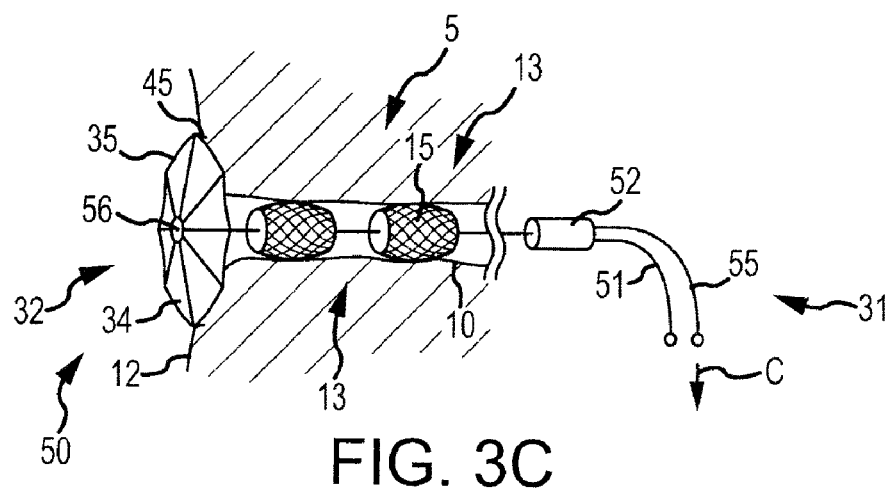
FIG. 3C is the same view as FIG. 3A, except the implantable fistula closure device and its expanding feature are in a non-compressed or expanded state.

For a discussion of a second embodiment of an expandable feature 50, reference is made to FIGS. 3A-3C, which are respective isometric views of the device 5 located in the fistula tract 10 and the expandable feature 50 progressively expanding from a non-expanded state to an expanded state. As shown in FIGS. 3A-3C, the device body 13 is generally the same as discussed above with respect to the embodiments depicted in FIGS. 1A and 1B such that the device body 13 includes individual porous bodies 15 coupled together via a connecting member 20. However, as indicated in FIGS. 3A-3C, the distal end 32 of the device 5 terminates in the expandable feature 50, which is coupled to the distal end of the connector member 20. The expandable feature 50 may be umbrella-like in that it assumes a generally conical configuration when in the non-expanded state (FIG. 3A) and opens up similar to an umbrella when transitioning to the expanded state (FIG. 3C).

As can be understood from FIG. 3C, the expandable feature 50 may include a flexible sheet or membrane 34 that extends over an expandable framework 35 similar to an umbrella and may be impermeable. The sheet 34 may be a biocompatible polymer or a bioresorbable material. The framework 35 may be a collapsible frame of thin ribs radiating from the center tip of the umbrella-like configuration. The framework 35 may be formed of a bioresorbable material. The expandable feature 50 is configured to occlude the distal tract opening 12 when fully expanded.

The expandable feature 50 may include attachment members 45 that are configured to attach to or engage the distal opening 12 of the tract 10. The attachment members 45 may be, for example, tines 45. Depending on the embodiment, the attachment members 45 may dissolve over time or be capable of being withdrawn out of the fistula in a manner similar to that discussed with respect to the framework 35.

A ring 40 or similar retention device 40 may maintain the expandable feature 50 in the non-expanded state depicted in FIG. 3A. The ring 40 may be configured to provide a tensile force that helps the distal end of the device 5 to stay in place and occlude the distal opening 12 of the fistula tract 10.

One or more actuation mechanisms 51, 55 extend along the connector member 20 to couple with the feature 50. The actuation mechanism 51, 55 may be filamentous or bioresorbable thread. Alternatively or additionally, the actuation mechanism may include a catheter 52 and one or more wires 51, 55 longitudinally displaceable within lumens of the catheter 52. The catheter 52 may extend through the bodies 15 the entire length of the device 5 and terminate at or near the ring 40 or the expandable feature 50. In such an embodiment, the framework 35 may be adapted to be removed from the sheet 34 by being pulled through the catheter after securing the conical member to the distal tract opening 10, leaving in place the occlusive polymer sheet 34 attached to the distal tract opening 10.

In one embodiment, an actuation mechanism 51 on the device proximal end 31 is pulled relative to the rest of the actuation mechanisms 51, 55, as indicated by arrow B, to disengage the retention device 40 such that the expandable feature 50 can bias at least partially open, as shown in FIG. 3B. In some embodiments, the feature 50 will be sufficiently biased in the open direction such that disengagement of the ring 40 from the feature 50 allows the feature 50 to fully deploy, as depicted in FIG. 3C. In other embodiments, once the ring 40 is disengaged via a first actuation mechanism 51, a second actuation mechanism 55 is pulled relative to the rest of the actuation mechanisms 51, 55, as indicated by arrow C, to cause the feature 50 to fully deploy, as depicted in FIG. 3C. In one embodiment, pulling the second mechanism 55 causes the proximal edges of the umbrella-like feature 50 to abut against the edges of the tract opening 12 and force the feature fully open 50. In another embodiment, pulling the second mechanism 55 causes a center portion 56 of the umbrella-like feature 50 to abut against the ring 40 and force the feature fully open 50.

As can be understood from FIGS. 3A-3C, the feature 50 expands in the lateral direction, which may be advantageous in that it reduces the profile of the distal portion of the device 5 in the bowel lumen. The device body 13 expands to fill the remainder of the fistula tract 10 as described above. Tension may be placed on the device 5, which may cause the expanding feature 50 to occlude to the distal end of the fistula tract 10. The tension may cause tines 45, where present, to more positively engage the surface of the tract distal opening 12.

In one embodiment, the ring 40 maintains the feature 50 in a non-expanded state, but the device does not include an actuation mechanism 51 to cause ring 40 to disengage from the feature 50. Instead, the act of negotiating the ring through the tract 10 causes the ring to slide out of engagement with the feature 50, thereby allowing the feature 50 to expand. Alternatively, exposure of the ring 40 to body fluids and/or body temperature causes the ring 40 to deteriorate such that the feature 50 is freed to expand.

In an alternative to the embodiments discussed above with respect to FIGS. 3A-3C, the expanding feature 50 may be biased to assume the biased configuration of FIG. 3C. However, the device 5 will not employ a retention ring 40 and an actuation mechanism 51 to retain the feature 50 in a non-expanded state until properly located in the fistula tract 10. Instead, the feature 50 will be maintained in the non-expanded state via the lumen walls of a catheter, sheath or guidewire employed to deliver the device 5. Once the device 5 is properly located within the tract 10, the catheter, sheath or guidewire can be withdrawn from about the device 5 to allow the feature 50 to bias into its expanded state.

In some embodiments, the feature 50 will not have a framework but will simply be a body or membrane that is self-supporting and biased to assume an expanded state.

Figure 4A:
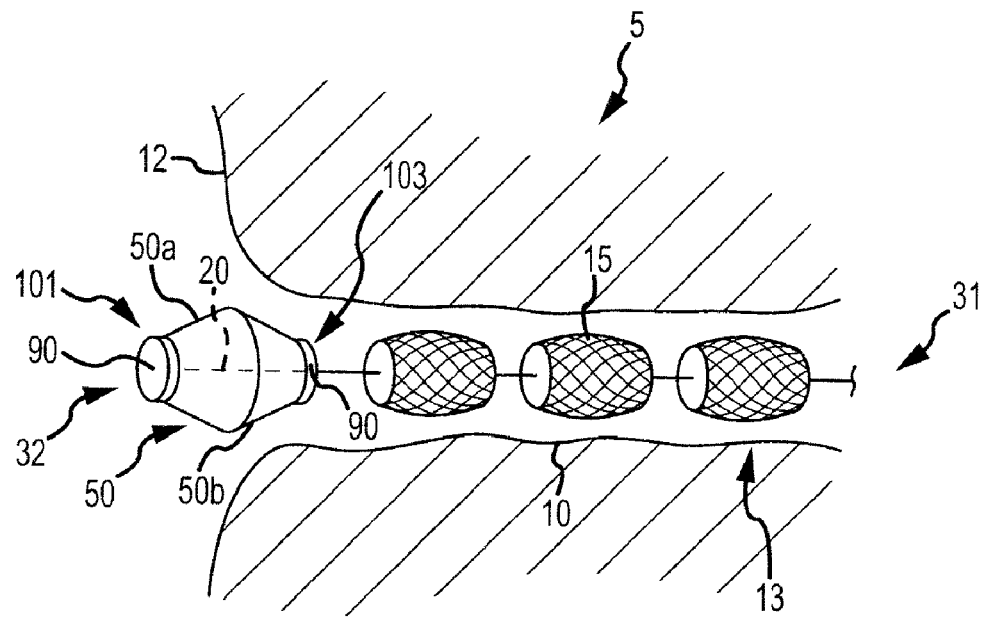
FIG. 4A is an isometric view of the implantable fistula closure device located in a fistula tract in a compressed or non-expanded state, wherein the distal end of the device includes an expanding feature in the form of an expandable member having a dual conical configuration.
Figure 4B:
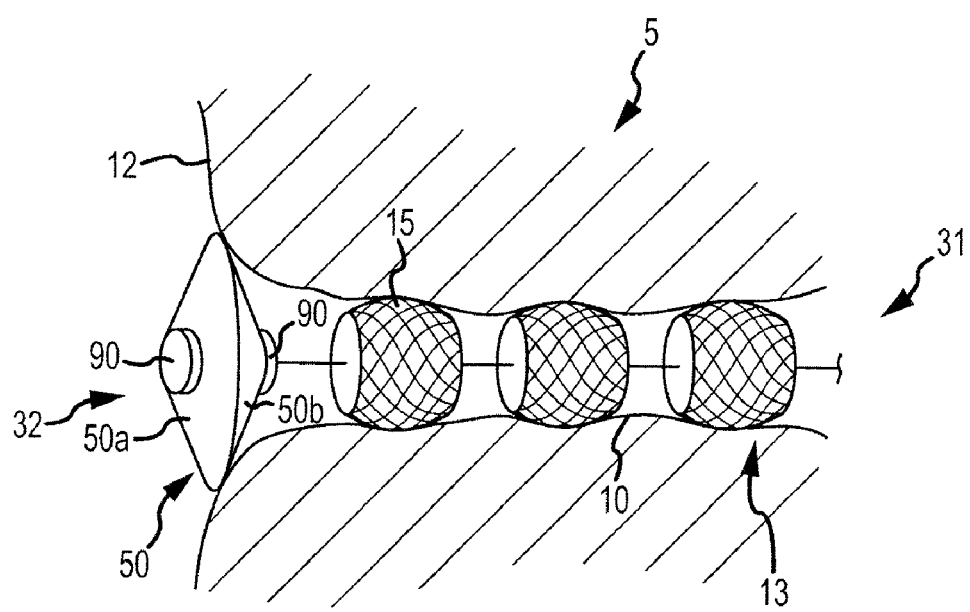
FIG. 4B is the same view as FIG. 4A, except the implantable fistula closure device and its expanding feature are in a non-compressed or expanded state.

For a discussion of a third embodiment of an expandable feature 50, reference is made to FIGS. 4A-4B, which are respective isometric views of the device 5 located in the fistula tract 10 and the expandable feature 50 is in non-expanded and expanded states. As shown in FIGS. 4A and 4B, the device body 13 is generally the same as discussed above with respect to the embodiments depicted in FIGS. 1A and 1B such that the device body 13 includes individual porous bodies 15 coupled together via a connecting member 20. However, as indicated in FIGS. 4A and 4B, the distal end 32 of the device 5 terminates in the expandable feature 50, which is coupled to the distal end of the connector member 20 and has a dual-conical configuration when in a non-expanded state.

As depicted in FIG. 4A, in one embodiment, the expandable feature 50 when in its dual-conical non-expanded state has a tip 101 of a first conical section 50a pointing distally, a tip 103 of a second conical section 50b pointing proximally, and the wide bases of each conical section 50a, 50b joined together. The tips 101, 103 may terminate in discs 90, the proximal of which may be connected to the connection member 20. As shown in FIG. 4B, when the expandable feature 50 is in an expanded state, the feature 50 mushrooms laterally.

In one embodiment, the conical sections 50a, 50b may be a gel-filled or otherwise readily deformable member sandwiched between the pair of generally rigid discs 90. The conical sections 50a, 50b may be a porous member formed from a material similar to that employed for the various bodies 15. The conical sections 50a, 50b may be a super compressed collagen.

Similar to the embodiment discussed with respect to FIGS. 2A-2D, in some embodiments, an actuation mechanism may extend along the connector member 20 to couple with the feature 50. The actuation mechanism may be filamentous or bioresorbable thread. Alternatively or additionally, the actuation mechanism may include a catheter and one or more wires longitudinally displaceable within lumens of the catheter. The catheter may extend through the bodies 15 the entire length of the device 5 and terminate at or near the expandable feature 50.

The proximal end of the actuation mechanism may be pulled or otherwise displaced relative to the rest of the actuation mechanism such that the actuation mechanism may cause the feature 50 to expand. For example, in one embodiment, the feature 50 is biased in a non-expanded state and pulling on the mechanism causes the discs 90 to converge towards each other, eventually engaging each other to become fixed in the converged state, as depicted in FIG. 4B. The discs 90 converging causes the deformable member 50a, 50b to squish or deflect outward, as illustrated in FIG. 4B, thereby serving as an anchor and/or sealing the tract opening 12. Expansion in the lateral direction may be advantageous in that it reduces the profile of the distal portion of the device 5 in the bowel lumen. The device body 13 expands to generally fill the rest of the fistula tract 10 as described above.

In another embodiment, the feature 50 is biased in an expanded state and operating the mechanism forces the discs 90 away from each other to cause the feature 50 to assume the dual-conical configuration depicted in FIG. 4A as the device 5 is being negotiated through the tract 10. Once the feature 50 passes through the tract opening 12, the mechanism can be released to allow the feature 50 to bias into the expanded state depicted in FIG. 4B. The feature 50 may then serve as an anchor and/or seal for the tract opening 12. The device body 13 expands to generally fill the rest of the fistula tract 10 as described above.

In an alternative to the embodiments discussed above with respect to FIGS. 4A-4B, the expanding feature 50 may be biased to assume the biased configuration of FIG. 4B. However, the device 5 will not employ an actuation mechanism to retain the feature 50 in a non-expanded state until properly located in the fistula tract 10. Instead, the feature 50 will be maintained in the non-expanded state via the lumen walls of a catheter, sheath or guidewire employed to deliver the device 5. Once the device 5 is properly located within the tract 10, the catheter, sheath or guidewire can be withdrawn from about the device 5 to allow the feature 50 to bias into its expanded state.

Figure 5A:
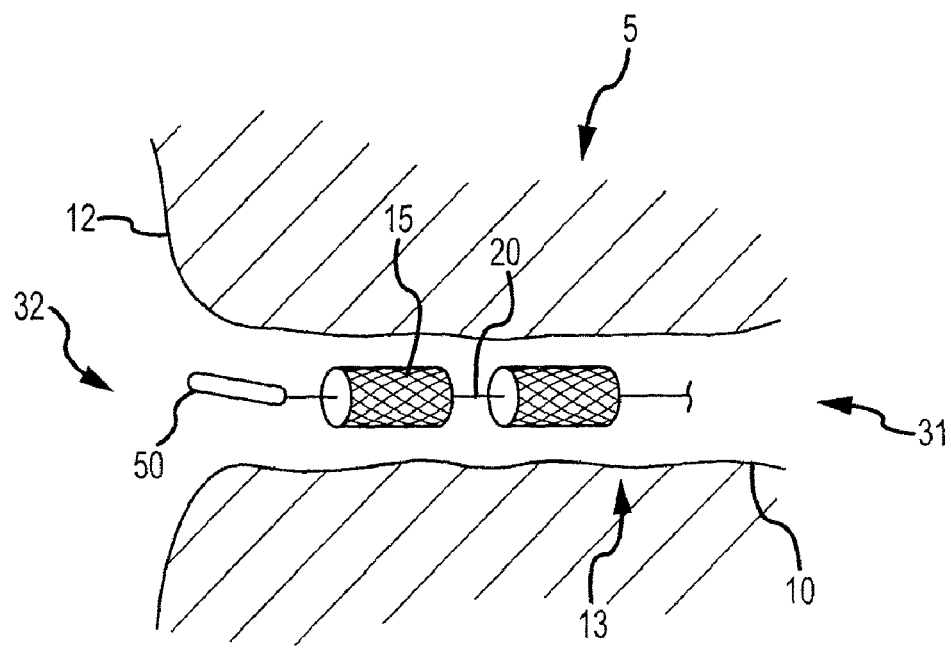
FIG. 5A is an isometric view of the implantable fistula closure device located in a fistula tract in a compressed or non-expanded state, wherein the distal end of the device includes an expanding feature in the form of an expandable balloon.
Figure 5B:
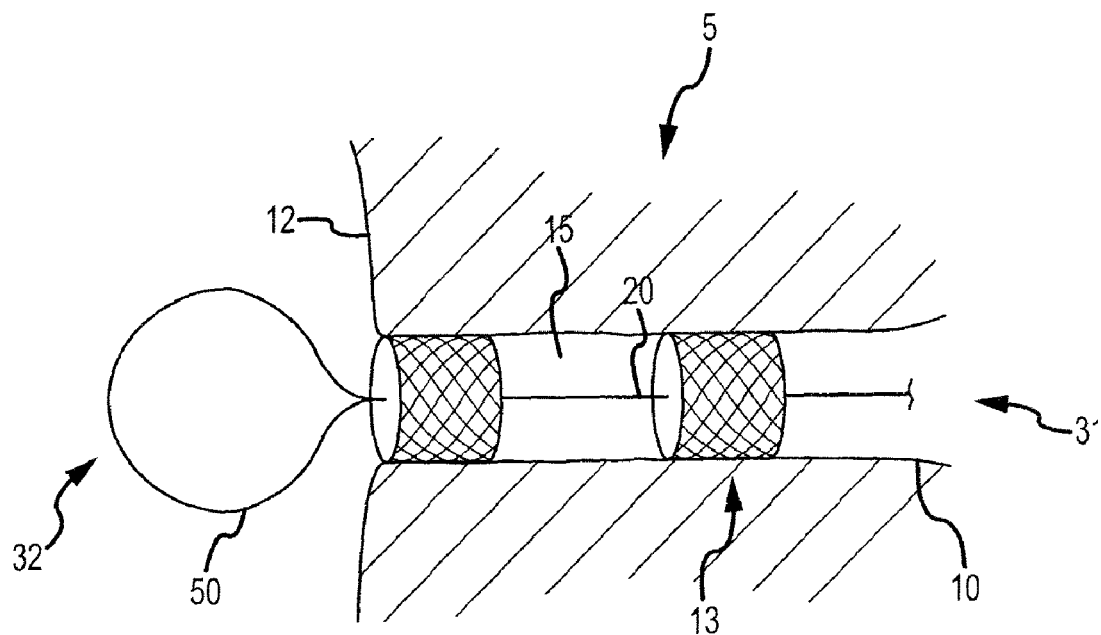
FIG. 5B is the same view as FIG. 5A, except the implantable fistula closure device and its expanding feature are in a non-compressed or expanded state.
Figure 5C:
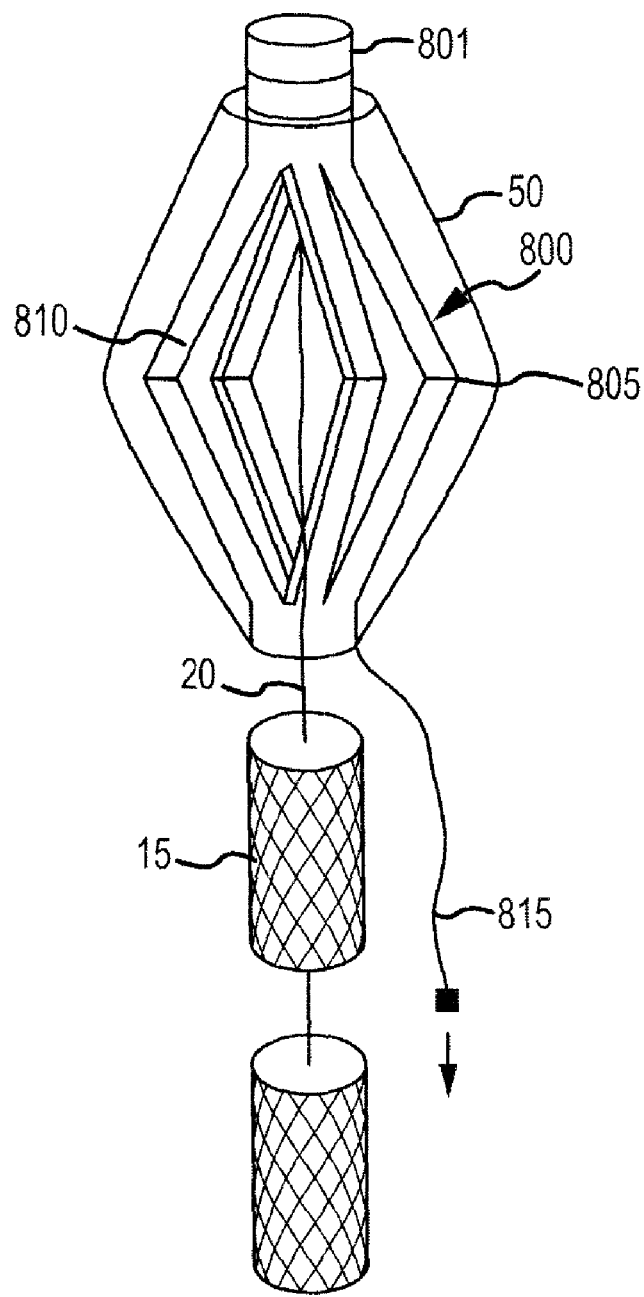
FIG. 5C is an isometric view of the expanding feature of FIG. 5A, wherein the expanding feature is in a slightly expanded state and includes a jack-like feature.
Figure 5D:
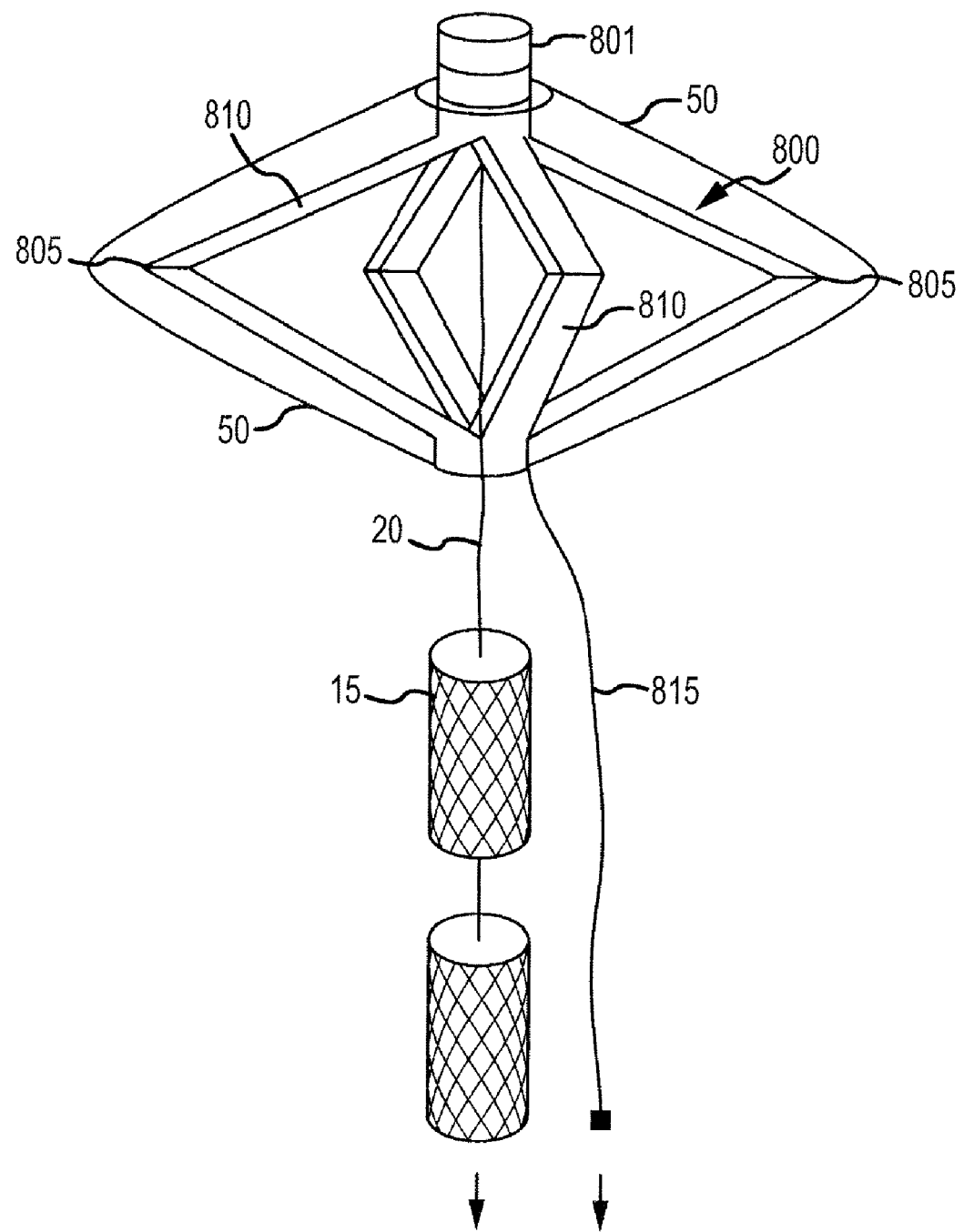
FIG. 5D is an isometric view of the expanding feature of FIG. 5B, wherein the expanding feature includes a jack-like feature.

In one embodiment, the dual-conical configured expandable feature 50 may be formed of a sheet or membrane extended over a collapsible and expandable framework similar in configuration, operation and material to those discussed with respect to FIGS. 5C-5D. In such an embodiment, the device 5 may include an actuation mechanism similar to that discussed with respect to FIG. 5C-5D.

For a discussion of a fourth embodiment of an expandable feature 50, reference is made to FIGS. 5A-5B, which are respective isometric views of the device 5 located in the fistula tract 10 and the expandable feature 50 in non-expanded and expanded states. As shown in FIGS. 5A and 5B, the device body 13 is generally the same as discussed above with respect to the embodiments depicted in FIGS. 1A and 1B such that the device body 13 includes individual porous bodies 15 coupled together via a connecting member 20. However, as indicated in FIGS. 5A and 5B, the distal end 32 of the device 5 terminates in the expandable feature 50, which is coupled to the distal end of the connector member 20 and is in the form of an inflatable balloon 50.

As depicted in FIGS. 5A and 5B, the balloon 50 may be coupled to the connector member 20. The connector member 20 may be a lumen 20 through which an inflation fluid may be transferred to the balloon 50 for its inflation. Alternatively, the lumen may be a separate structure that extends along or near to the connector member 20.

As indicated in FIG. 5A, the expandable feature or, more specifically, balloon member 50 of the device 5 is advanced in a non-inflated state through the distal opening 12 of the fistula tract 10. As can be understood from FIG. 5B, once the balloon 50 of the device 5 is in position, the balloon 50 may be inflated via the lumen 20 with a material such as air, saline or other biocompatible fluid or solidifying gel. Tension may then be applied to the device 5 via the connector member 20, which causes the balloon member 50 to occlude the distal opening 12 of the fistula tract 10. In some embodiments, tension may be applied to the device 5 via the connector member 20 where the connector member 20 is only connected to the balloon member 50 and is not otherwise connected to the device body 13. The balloon member 50 may also be retracted back against the distal opening 12 of the tract 10. The device body 13 expands to generally fill the rest of the fistula tract 10 as described above.

In one embodiment, the balloon 50 may include an adhesive coating adapted to adhere to the tissue surface of the region adjacent the distal opening 12 of the fistula tract 10. The balloon 50 may include micropores on the side of the balloon 50 intended to face towards the tissue to be contacted by the balloon 50. The micropores may allow any inflating fluid to leak out of said pores, thereby allowing the delivery of an adhesive/sealant to the distal opening 12.

Depending on the embodiment, the balloon 50 may be a fluid inflatable or expandable disc-shaped balloon adapted to occlude the distal tract opening. Alternatively, the balloon 50 may be a fluid inflatable or expandable flat cone-shaped balloon adapted to occlude the distal tract opening. The balloon 50 may be formed of a biocompatible polymer. Alternatively, the balloon 50 may be formed of a biodegradable or bioabsorbable material.

In one embodiment, the balloon 50 may be injected with a time curing liquid material, e.g., a scone material such as that manufactured by Nusil Silicone Technology (Carpinteria, Calif.). Once the liquid material starts to cure, the clinician may force the balloon against the peri-opening area at the distal opening of the fistula tract, thereby causing the balloon and the liquid material contained therein to assume the shape of the peri-opening area. Once the liquid material is substantially cured, the balloon 50 will retain the shape it assumed, resulting in a balloon that is custom shaped for the distal tract opening and creating a seal of the distal tract opening that is potentially more likely to be fluid-tight as compared to other distal anchor configurations.

Alternatively, the balloon 50 may be mechanically inflated or expanded, as can be understood from FIG. 5C, which shows a side view of such a device 5. The mechanically inflatable or expandable balloon 50 includes a jack-like feature 800 and a radio-opaque marker band 801 on a first central axis point 802 of the jack-like feature 800. In one embodiment, the jack-like feature also includes a connecting member 20 to connect the jack-like feature 800 to porous bodies 15 of the device 5. In one embodiment, the jack-like feature 800 includes four arms 810 with weak points 805 which aid in the transition between non-expanded and expanded states. In other embodiments, the jack-like feature 800 may have more than four arms or less than four arms. The arms 810 are joined at least one of a first or second central axis point 802.

The balloon 50 generally conforms to the jack-like feature 800. That is, when the jack-like feature 800 is in a non-expanded state, the balloon 50 is not inflated. When the jack-like feature 800 is in an expanded state, the balloon 50 is inflated and, when in the appropriate position, occludes the distal tract opening. Following installation of the balloon 50 at the distal end 12 of the tract 10, the jack-like feature 800 may be collapsed and removed from the fistula closure device 5 via a recoil member 815, which may be a filamentous string or suture line.

Regardless of whether the balloon 50 is expanded via injection of a fluid or via an expanding mechanical framework 800, the material forming the balloon 50 may provide a resilient distal anchor 50 that may readily conform to irregular distal tract openings. As a result, the balloon 50 may be able to readily seal an irregular distal tract opening.

Figure 6A:
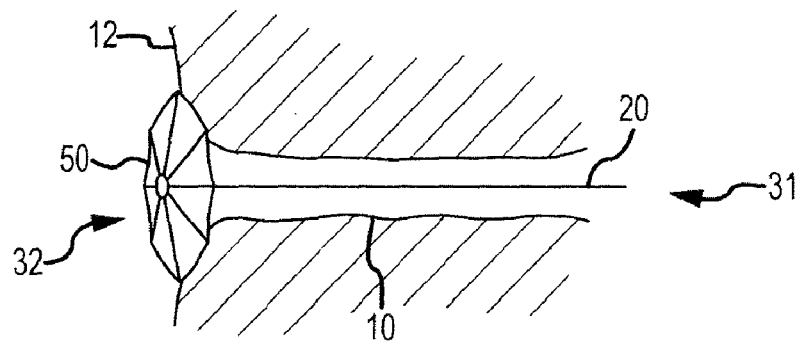
FIG. 6A is an isometric view of the device in the tract with the expandable feature fully expanded, but the device is lacking a body.
Figure 6B:
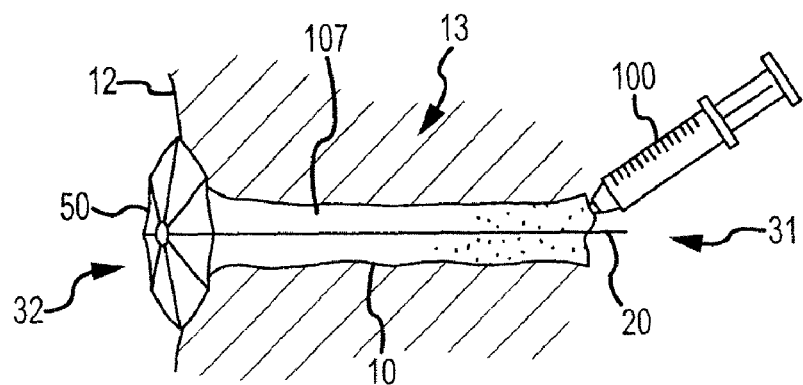
FIG. 6B is the same view as FIG. 6A, except the device has a body of an injected material.
Figure 6C:
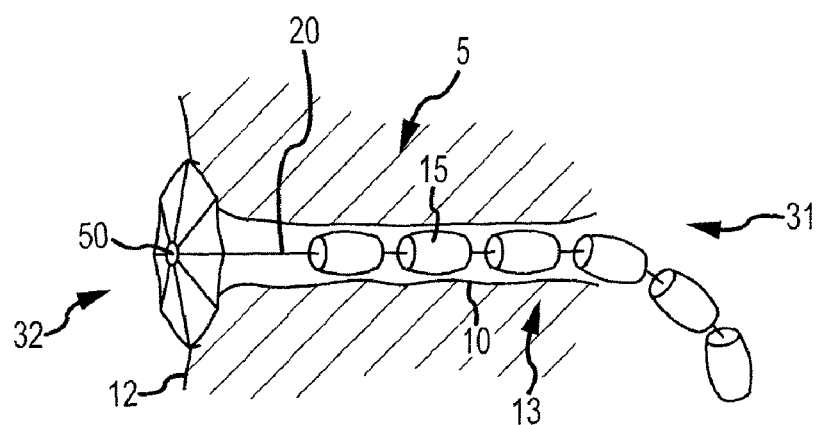
FIG. 6C is the same view as FIG. 6A, except the device has a body of porous individual bodies.

For a discussion of a fifth embodiment of the fistula closure device 5 employing an expandable feature 50, reference is made to FIGS. 6A-6C. FIG. 6A is an isometric view of the device 5 in the tract 10 with the expandable feature 50 fully expanded, but the device 5 is lacking a body 13. FIGS. 6B and 6C are the same respective views as FIG. 6A, except the device 5 has a body 13 or an element that serves a purpose similar to the body 13.

As shown in FIG. 6A, the device 5 may simply include an expandable feature 50 and a connecting member 20, such that the device 5 initially lacks a body 13 or an element that serves a purpose similar to the body 13. The feature 50 may be like any of the above-described expandable features 50 discussed with respect to FIGS. 2A-5B. The feature 50 and member 20 may be deployed within the tract 10 via any of the above-described methods.

As can be understood from FIG. 6B, in one embodiment, once the device 5 is deployed in the tract such that the expanding feature 50 occludes the distal opening 12 of the tract 10, a biocompatible gel material or a foam 107 adapted to promote healing of the fistula tract 10 may be inserted into the fistula tract 10 proximal of the expanding feature 50. The material 107 thereby further occludes the tract 10 and forms the body 13 of the device 5. The biocompatible gel material or foam 107 may harden into a consistency such as an open-cell foam, further promoting tissue ingrowth.

The biocompatible gel or foam 107 may also be an injectable polymer that may fill and occlude the fistula tract 10 and may be a biodegradable scaffold for tissue replacement and fistula tract healing. The injectable polymer 107 may be injected into the fistula tract via a syringe 100 or other delivery device. The material 100 may also be delivered into a porous scaffold previously placed into the fistula tract. The injectable polymer 100 may improve the occlusive properties of the porous scaffold placed into the tract. The injectable polymer may improve the healing properties of the porous scaffold placed into the tract.

It should be noted that while the injection of a biocompatible gel material or foam 107 is discussed with respect to FIG. 6B in the context of a device 5 that is deployed without a body 13 or a similarly functioning element, those skilled in the art will readily understand that the same or similar gel material or foam 107 may be injected into the fistula tract 10 prior to or subsequent to the delivery of the rest of the device embodiments disclosed herein with respect to FIGS. 1A-5B and 6C. Thus, any one of the device embodiments disclosed herein with respect to FIGS. 1A-5B and 6C may be deployed in the tract 10 with their respective bodies 13, and the material 107 may be injected into the tract 10 prior or subsequent to the device deployment. Also, in some embodiments, the gel or foam material may be delivered into the fistula tract via a frame or member, as opposed to be injected.

Figure 10:
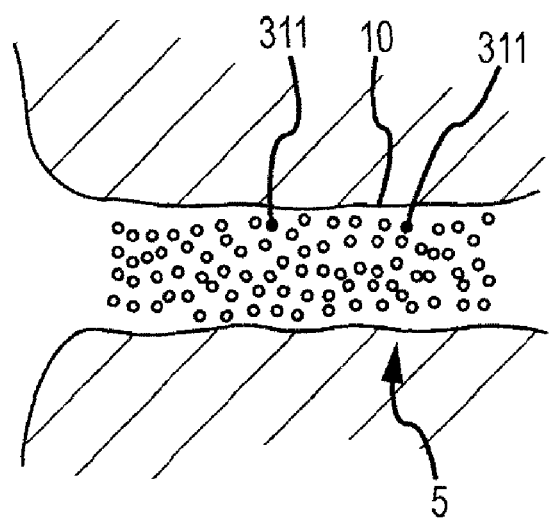
FIG. 10 is a side view of a fistula tract occluded by fragmented solids such as pellets.

In some embodiments, as indicated in FIG. 10, the closure device 5 is a material other than a gel or foam 107, such as pellets 311, may be inserted (e.g., injected) into the fistula tract 10 to fill and occlude the tract 10. The pellets 311 are made of a material similar to the gel material 107 and may possess similar expansion, occlusive, and healing properties. The pellets 311 may be inserted in a compressed or a non-compressed state. The pellets 311 may provide the ability to more efficiently and fully fill, occlude and conform to the tract 10. This may especially be the case if the pellets 311 are inserted into the tract 10 in a compressed state. In one embodiment, the pellets 311 are micro pellets or micro spheres such as the STAR materials as manufactured by Healionics Corporation (Redmond, Wash.). Depending on the embodiment, the micro pellet or spheres 311 may or may not expand once inserted in the tract 10. The micro pellets may have a specific controlled pore size, porosity and even a specific controlled expansion percentage. Micro pellets or spheres similar to the STAR materials have been shown to promote the growth of larger vessels through the spaces between adjacent pellets, thereby increasing and encouraging tissue ingrowth.

In some embodiments, micro pellets or spheres are injected or otherwise inserted into the tract 10 suspended in a gel, saline or other fluid. In some embodiments, the suspension fluid need not convert to a structure, but can drain out of the tract or be resorbed, leaving behind the micro pellets.

The micro pellets or spheres, regardless if they expand or not, can function to occlude and conform to the tract 10. This is due in part to there being millions of tiny micro pellets, which will easily infill any voids in the tract.

Figure 6D:
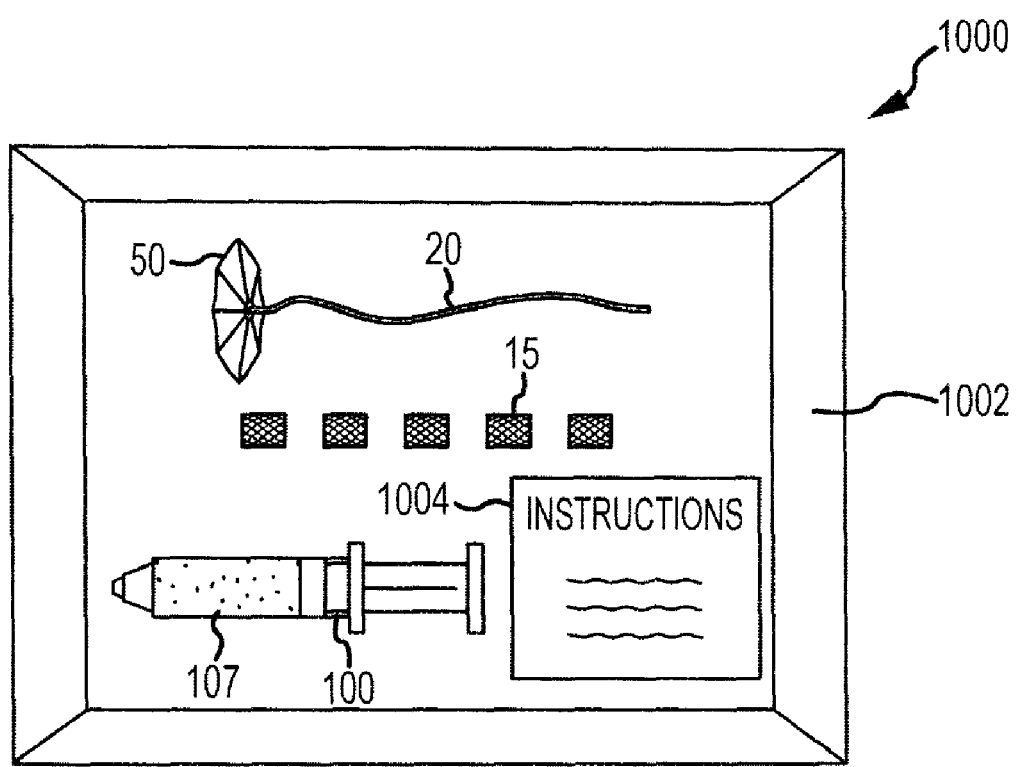
FIG. 6D is a depiction of a medical kit for closing a fistula and, in some embodiments, containing at least some of the components depicted in FIGS. 6A-6C or FIG. 10.

As can be understood from FIG. 6D, the embodiments described with respect to FIGS. 6A-6C can be provided as a kit 1000 wherein at least some of the components of the fistula closure device 5 are provided in a sterile package 1002. For example, the sterile package 1002 may contain the delivery device 100, the gel or liquid material 107, the connector member 20 and the distal anchor 50. The sterile package 1002 may also or alternatively contain individual porous bodies 15 for threading over the connecting member 20. Instructions 1004, which may be provided on or with the kit 1000, or alternatively via the internet or another indirect method, provide direction on how to employ the kit. The instructions may outline a deployment method similar to those described immediately above. While FIGS. 6D and 9D depict medical kits for the embodiments respectively depicted in FIGS. 6A-6C and 9A-9C, the concept of kits may readily be applied to the rest of the embodiments disclosed herein.

As indicated in FIG. 6C, in one embodiment, once the device 5 is deployed in the tract such that the expanding feature 50 occludes the distal opening 12 of the tract 10, bodies 15 such as those discussed above may be threaded over the connecting member 20 to generally create a device 5 similar to those discussed above with respect to FIGS. 2A-5B. Depending on the embodiment, the connecting member 20 may or may not span the entire length of the fistula tract 10, and the connecting member may or may not be a simple suture line. Similarly, the bodies 15 threaded over the connector member 20 may or may not fill the entire length of the fistula tract 10. The bodies 15 may be of the same porous type and construction as discussed above. As with the above-described embodiments, the expandable bodies 15 may expand to fill the fistula tract 10 and form the body 13 of the device 5.

Figure 7A:
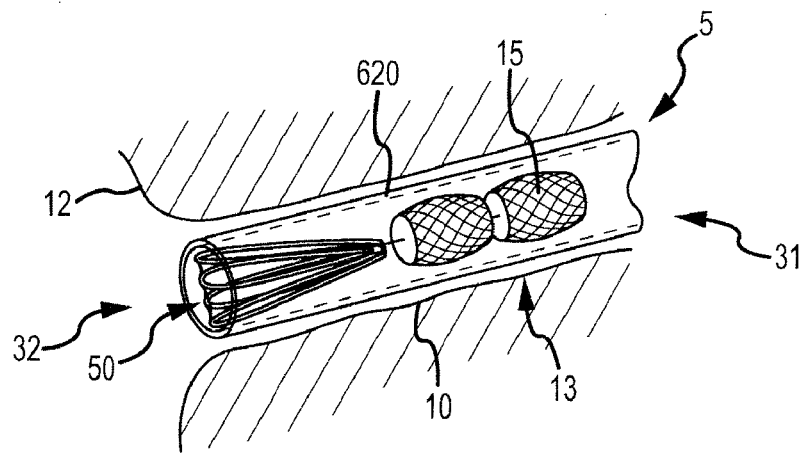
FIG. 7A is an isometric view of the implantable fistula closure device located in a fistula tract in a compressed or non-expanded state, wherein the distal end of the device includes an expanding feature that is temperature activated.
Figure 7B:
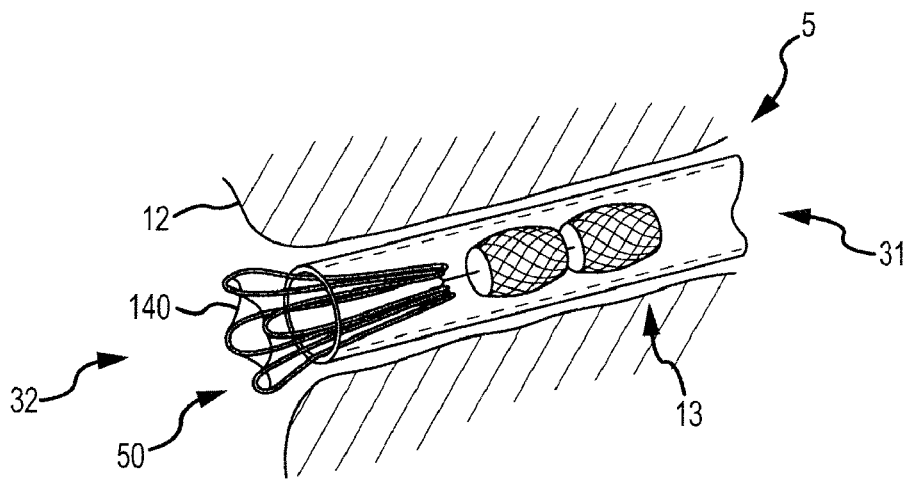
FIG. 7B is the same view as FIG. 7A, except the device and its expanding feature are in a partially non-compressed or partially expanded state after retraction of the delivery sheath.
Figure 7C:
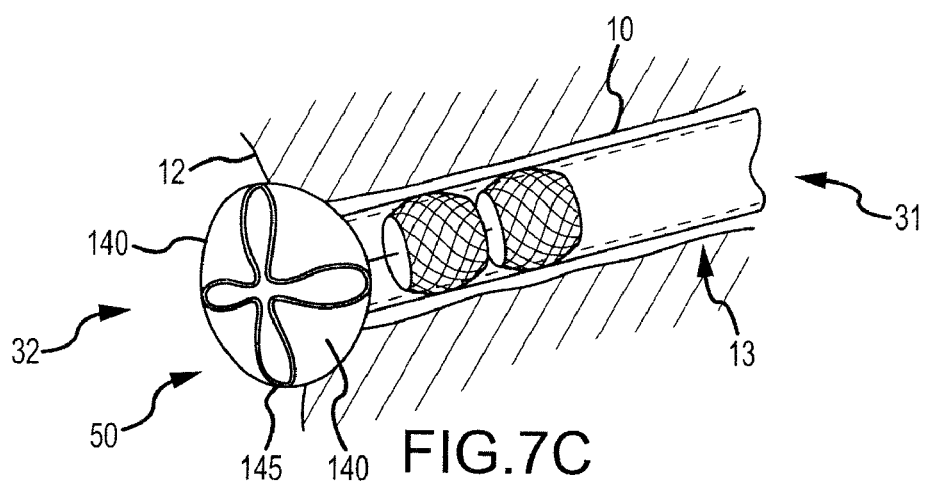
FIG. 7C is the same view as FIG. 7A, except the device and its expanding feature are in a non-compressed or expanded state.

For a discussion of yet another embodiment of the fistula closure device 5 employing an expandable feature 50, reference is made to FIGS. 7A-7C. FIG. 7A is an isometric view of the implantable fistula closure device located in a fistula tract in a compressed or non-expanded state, wherein the distal end of the device includes an expanding feature that is temperature activated. FIG. 7B is the same view as FIG. 7A, except the implantable fistula closure and its expanding feature are in a partially non-compressed or partially expanded state after retraction of the delivery sheath. FIG. 7C is the same view as FIG. 7A, except the implantable fistula closure and its expanding feature are in a non-compressed or expanded state.

As shown in FIG. 7A, the device body 13 is generally the same as discussed above with respect to the embodiments depicted in FIGS. 1A and 1B such that the device body 13 includes individual porous bodies 15 coupled together via a connecting member 20. However, as indicated in FIGS. 7A-7C, the distal end 32 of the device 5 terminates in the expandable feature 50, which is coupled to the distal end of the connector member 20 and is in the form of a star-shaped framework supporting a membrane.

As can be understood from FIGS. 7A-7C, the expanding feature 50 may be biased to assume the biased configuration of FIG. 7C. As shown in FIG. 7A, the feature 50 may be maintained in the non-expanded state via the lumen walls 620 of a catheter, sheath or guidewire employed to deliver the device 5. As indicated in FIG. 7B, once the device 5 is properly located within the tract 10, the catheter, sheath or guidewire can be withdrawn from about the device 5 to allow the feature 50 to bias into its partially expanded state. As can be understood from FIG. 7C, upon exposure to body fluids or body temperature, the feature 50 is allowed to expand into its expanded state. It should be noted that the feature 50 may be in a partially expanded state within the delivery device or before complete withdrawal of the delivery device from about the device 5. The feature 50 may then serve as an anchor and/or seal for the tract opening 12. The device body 13 expands to generally fill the rest of the fistula tract 10 as described above.

In one embodiment, the feature 50 has a star shaped framework 145 supporting a webbing-like membrane 140 between the tines of the star. In other embodiments, the framework 145 may be a different shape, such as a polygon, and the webbing 140 is included as needed to occlude the distal opening 12 of the fistula tract 10. Different aspects of the feature 50 may be formed from a temperature dependent polymer or metal, such as nitinol, or other self-expanding, temperature dependent material. The feature 50 may also simply be biased and expand once freed from the confines of the lumen walls 620.

In some embodiments of each of the fistula closure devices 5 equipped with an expandable feature 50, as discussed above with respect to FIGS. 2A-7C, the device 5 and its expandable feature 50 in a non-expanded state are configured to pass through a lumen of catheter size of nine French or smaller, and in some embodiments, twenty French or smaller. The expandable feature 50 or portions thereof may be adapted to adhere to the tissue surface area forming a distal tract opening 12. For example, the expandable feature 50 may include a biocompatible adhesive surface of the feature 50 intended to contact the tissue surface area forming the opening 12. The adhesive may activate after exposure to a fluid (e.g., body fluid) or body temperature. The adhesive may initially strengthen the bond of the feature 50 to the tissue and then gradually degrade in strength as fistula tract healing occurs or after fistula tract healing. Depending on the embodiment, the adhesive may create a fluid impermeable seal for at least 7, 14, 21, 28, 35, 60 or any other number of days.

In some embodiments of each of the expandable features 50 discussed above with respect to FIGS. 2A-7C, the expandable feature 50 may include attachment members 45 such as micro hooks or tines. Such attachment members 45 may be located on a surface of the feature 50 intended to contact the tissue surface area forming the opening 12, thereby facilitating the adherence of the feature to the tissue surface bordering the distal tract opening 10 and the occlusion thereof.

In some embodiments of each of the expandable features 50 discussed above with respect to FIGS. 2A-7C, the expandable feature 50 or various components thereof may be resorbable and adapted to occlude the fistula tract and then resorb after the tract 10 has closed at least about 45%, 55%, 65%, 75%, 85%, 95%, 100% or any other percentage. The feature 50 or various components thereof may be biodegradable and/or adapted to fall away from the distal fistula opening 12 and be extruded through the gastrointestinal tract. For example, the feature 50 or various components thereof may be secreted from the body after the tract 10 has progressed towards closure (e.g., after at least 7, 14, 21, 28, 35 or any other number of days adequate to achieve sufficient closure.

In some embodiments of the devices 5 employing each of the expandable features 50 discussed above with respect to FIGS. 2A-7C, the connecting member 20 may be a biocompatible polymer string extending through the tract from the expanding feature 50. The connecting member 20 may be formed of a resorbable material and may resorb after the tract 10 has closed at least about 45%, 55%, 65%, 75%, 85%, 95%, 100% or any other percentage. The member 20 may provide tensile force substantially perpendicularly to the feature 50, thereby pulling the feature 50 against the tract's distal opening 12 and anchoring the feature 50 in place to occlude the distal tract opening. As explained above with respect to FIGS. 11A and 11B, the device 5 may include a clip 900 at the proximal end, which may generally occlude, but not seal, the proximal end of the tract and allow tension in the member 20, which extends between the clip 900 and feature 50.

The fistula closure devices 10 as described herein may be implanted into a fistula tract 10 via various methods. For example, the fistula tract 10 may be visualized via direct visual inspection or medical imaging methods (e.g., Fluoroscopy, CT scan, MRI, etc.). A guidewire may be negotiated through the tract 10. The tract 10 may then be de-epithelializing irrigated. The device 5 may then be threaded over the guidewire and pushed into the tract 10. The distal fistula opening 12 may be occluded via elements of the device 5 (e.g., the most distal body 110 and/or expanding feature 50). The device 5 may be trimmed to the length of the tract 10, after which the guidewire is removed. The device 5 and, more specifically, the device body 13 may be irrigated to cause expansion of the body 13. The device 5 may be anchored at the proximal fistula opening with a proximal end piece. For example, a retaining member may be connected to the distal end of the device 5 and secured to the region surround the proximal end opening of the tract 10, thereby creating tension in the device 5. The proximal fistula opening may then be covered with a dressing.

In another method of implanting the fistula closure device 5 in a fistula tract 10, a compressed porous scaffold 13 is placed in the fistula tract 10, wherein the scaffold 13 is at least partially inserted into the tract 10. The porous scaffold may be filled with an injectable polymer fluid 100, which may form an occlusive plug and may promote tissue growth and hence healing of the fistula tract. The method may further include fixating the device 5 in the tract 10 using a biocompatible connecting member 20, such as a string, which is attached to the device 5. The polymer 100 injected into the tract 10 may be in a form that allows the foam to approximate the walls of the fistula tract 10 and fill any voids in the tract.

In another method of implanting the fistula closure device 5 in a fistula tract 10, a distal end 32 of the device 5 may be placed in such a way as to protect and occlude the distal end 12 of a fistula tract 10. The body 13 of the device 5 may be inserted into the fistula tract 10 in such a way as to at least partially fill the fistula tract 10. The surface load or point load dependant expansion of porous bodies 15 may then be activated within the fistula tract and the device 5 can be anchored in place at the distal and/or proximal ends 32, 31 as discussed above. For purposes of this disclosure, surface load or point load dependent expansion refers to the expansion of the porous bodies where, upon contact between the fistula tract wall (the "load") and a point on the porous body, that point of the porous body will stop expanding. The points on any or all of the rest of the porous body will continue to expand until the remaining points also make contact with the fistula tract wall. Thus, unlike the occluding bodies of fistula closure devices known in the art, the surface load or point load dependant expansion of the bodies 13 of the device 5 disclosed herein allows the body 13 to generally fill and conform to the tract 10 without distorting the tract 10 or causing the tract to conform or deform due to the expansion of the body 13 in the tract. This ability of the body 13 can be a result of pre-compression of the body 13 and/or the nature of the material used. Examples of materials from which to form the bodies 15 of the device 5 include: AngioSeal-like products, collagen sponge or other biomaterial materials as manufactured by Kensey Nash Corporation (Exton, Pa.); CollaPlug® or other collagen products as manufactured by Integra Corporation (Plainsboro, N.J.); and STAR® materials as manufactured by Healionics Corporation (Redmond, Wash.).

With respect to the CollaPlug® material, in some embodiments, the CollaPlug® material may be compressed prior to delivery into the tract 10, the CollaPlug® material being approximately 90% porous.

With respect to the STAR® materials, some such materials are know to have a specific pore size that promotes better angiogenesis. The STAR® materials and some of the materials and products discussed above are capable of achieving the controlled pore size and overall porosity discussed earlier in this Detailed Discussion.

In another method of implanting the fistula closure device 5 in a fistula tract 10, the tract is visualized and a guidewire is routed into the tract 10. The tract 10 is de-epithelialized and irrigated to remove any unwanted internal matter. The fistula closure device 5 may be tracked over the guidewire and the device 5 may then be received into the fistula tract until the distal end of the device 5 extends beyond the distal fistula opening 12. The device 5 may be expanded by irrigation so as to approximate the fistula tract 10. The device 5 may be trimmed if required. The method may include clipping or otherwise securing the proximal end of the device 10 at the proximal tract opening to provide a secure anchor. The proximal opening may then be coved with a dressing. In one embodiment, the segmented body 13 of the device 5, when in an expanded state, generally approximates the volume of the fistula tract with minimal distortion of the fistula tract.

In some embodiments, the bodies 15 of the fistula closure device 5 are formed from materials other than a graft, wherein graft is defined as a transplant from animal or human tissue.

In some embodiment, the bodies 15 of the fistula closure device 5 are formed from materials other than an extracellular matrix ("ECM") material, wherein ECM material is defined as decellularized organic tissue of human or animal origin.

Furthermore, in some such embodiments, the bodies 15 of the fistula closure device 5 are formed from materials other than those that are remodelable, wherein remodelable is defined as the ability of the material to become a part of the tissue. Instead, in some embodiments, the bodies 15 of the fistula closure device 5 may rely heavily on the amount of induced cross-linking that allows control of the resorption rate. Cross-linking essentially destroys the remodelable properties of a material. While remodelable may not exclude resorbable material completely, in some embodiments, the bodies 15 of the fistula closure device 5 may be formed of material that is completely resorbable and has no remodelable requirements or capabilities.

In some embodiments of the fistula closure device 5, the device body 13 is formed of multiple bodies 15 to form a segmented body 13. The body 13 may include a distal occlusion member 50 (e.g., an umbrella-like member), the member 50 acting as an occlusion mechanism that is more of an occlusive cover rather than a plug or sealing member.

Figure 14A:
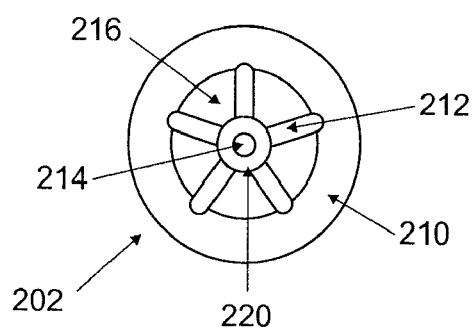
FIG. 14A is a superior view of another embodiment of a fistula closure device comprising a resilient annular collapsible distal end.
Figure 14B:
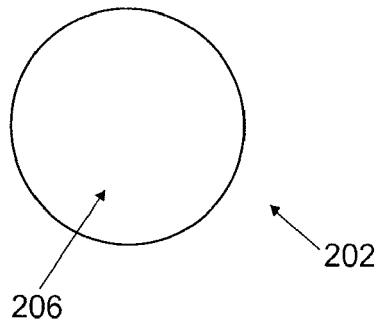
FIGS. 14B and 14C are inferior and side elevational views of the device in FIG. 14A.
Figure 14C:
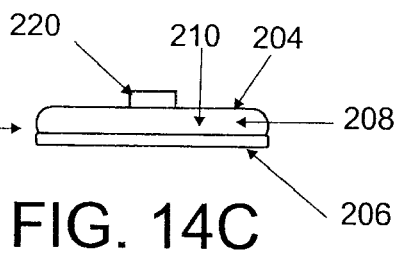

FIGS. 14A to 14C depict another example of a fistula closure device, comprising a generally disc-shaped sealing body 202 having a proximal surface 204, distal surface 206 and a outer side wall 208 therebetween. The sealing body 202 may be configured to be collapsed for delivery to the target location and to re-expand when deployed. In some examples, the sealing body 202 may comprise a resilient material that re-expands upon removal of any restraint acting on the collapsed body, such as the removal or withdrawal of a delivery catheter, or the cessation of suction or vacuum acting on the collapsed body. For example, the body may be molded (e.g. injection or blow molded) using polyurethane, polyvinyl chloride or other resilient polymeric material into its base configuration that may then be collapsed used suction or vacuum. In some examples, the sealing body 202 may comprise a shape-memory or superelastic material, including but not limited to nickel-titanium alloys or shape-memory polymers. In other examples, re-expansion may be facilitated by the infusion or inflation of a liquid or gas into the sealing body 202.

The sealing body 202 may comprise a generally flat and circular configuration as depicted in FIGS. 14A and 14B, but in other examples, may be thicker and non-circular as described previously, including oval or rectangular shaped devices. To facilitate sealing of the fistula tract, the proximal surface 104 of the sealing body 202 may comprise an seal 210. In the depicted example, the seal 210 is located along the peripheral edge of the sealing body 202, but in other examples may be spaced away from the edge. The seal 210 depicted in FIG. 14A comprises an annular configuration, but in other examples, the seal may have a polygonal, oval, star or square shape, for example, that may be the same or different shape as the sealing body 202. The seal 210 may be solid or may comprise a hollow interior. In some instances, a hollow interior may facilitate collapse of the sealing body 202 for delivery, or to facilitate deformation or conformation to the shape of target location. As further depicted in FIG. 14A, the sealing body 202 may also comprise one or more ribs or support structures 212. The number of support structures 212 may be in the range of about one to about ten or more, from about two to about eight, about three to about six, or about five support structures, for example. The support structures 212 may be evenly or symmetrical space apart in a radial configuration with respect to the center of the sealing body 202 or a midline of the sealing body 202. The support structures 212 may also be solid or hollow. In some examples comprising at least one hollow support structure 212 and a seal 210 that is at least partially hollow, the support structure 212 and the seal 210 may be in fluid communication through an access lumen 214 provided on the sealing body 202. The access lumen 214 may permit injection or filing of materials into the body 102, including but not limited to contrast agents (e.g. barium, contrast saline, etc.) or a bulking material such a silicone. The distal surface 206 may be generally smooth, which may facilitate passage of materials through the gastrointestinal tract past the implanted sealing body 202, but in other examples may comprises recesses, openings or projections. The proximal surface 204 may comprise recesses 216 located between the support structures 212 and/or the annular seal 210. In some variations, the recesses may reduce the degree of surface contact between the sealing body 202 and the surrounding tissue, thereby shifting sealing forces along the annular seal 210.

Figure 15:
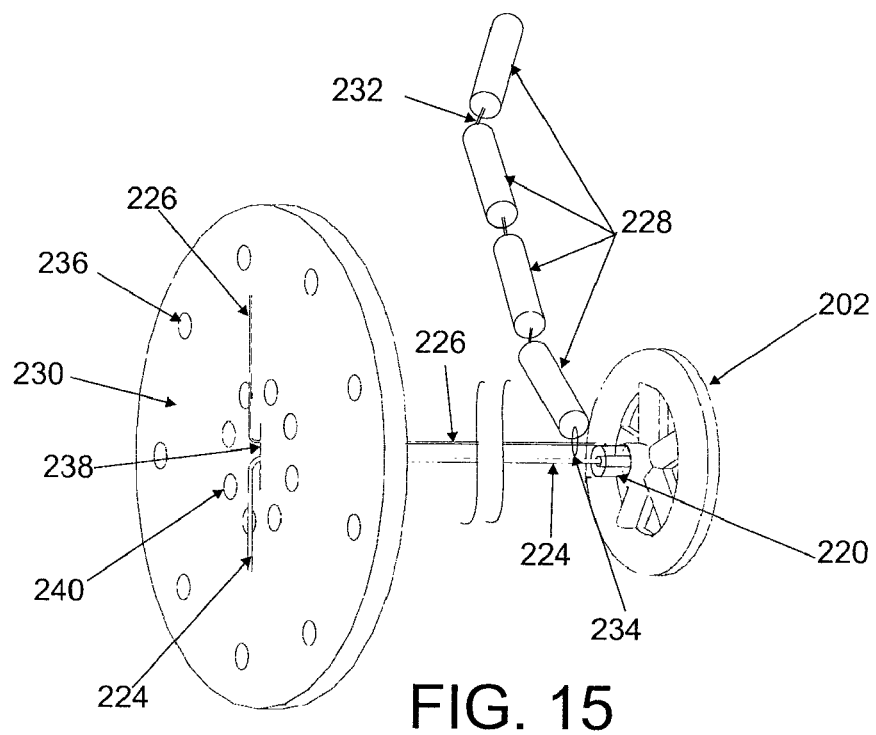
FIG. 15 is a schematic representation of the device in FIGS. 14A to 14C used with a proximal retaining structure and a plurality tethered, expandable members attached to the device.

The sealing body 202 may further comprise an attachment structure 120 to facilitate delivery of the sealing body 202. The delivery catheter, if any, may releasably engage the sealing body 202 at the attachment structure 220. The attachment structure 220 may also be the attachment site for one or more tethers or sutures that may be used in conjunction with the sealing body 202. In some further examples, the attachment structure 220 is located centrally with respect to the overall shape of the sealing body 202, but in other examples may be eccentrically located. The attachment structure 220 may be integrally formed with the access lumen 214, or may be separate from the access lumen, which may be used to inject materials into the hollow lumens and/or cavities of the support structures 212 and the annular seal 210, if any. In other examples, through lumens in the body may permit access to the intestinal lumen for fluid sampling, placement of sensors, and/or therapeutic agent delivery Referring to FIG. 15, the sealing body 202 may be a distal portion of a fistula closure device 100. In use, the sealing body 202 may seal the fistula tract by tensioning the sealing body 202 against the intestinal wall of a patient though one or more tethers 224 and 226 attached to the sealing body 202. The tethers 224 and 226 may be attached at the attachment structure 220 or other location of the sealing body 202, including but not limited to the annular seal 210 and/or the support structures 212. The multiple tethers 224 and 226 may be color coded to distinguish the various tethers during the implantation procedure. At least one of the tethers 224 may be used to apply tension to the sealing body 202 and seal the fistula tract. In some examples, a second tether 226 may be provided to as a guide element for delivery of the expandable members. In some variations, providing separate tethers 224 and 226 may reduce the risk of free-floating or unsecured expandable members 228 should the tensioning tether 224 rupture. FIG. 15, for example, depicts the second tether 226 that may be used to deploy one or more expandable members 238 along the fistula tract. At least one or both of the tethers 224 and 226 may be secured using a proximal restraining structure 230 that resists distal sliding or displacement of the tether 224 and/or 226 by providing an increased surface area or transverse dimension that resists collapse or entry of the restraining structure 230 into the fistula tract.

As shown in FIG. 15, the expandable members 228 may comprise generally elongate collagen plugs (or other biocompatible material) that are configured to expand, fill and conform to surrounding tissue structures. The plugs may have a generally cylindrical shape, but in alternative examples may have any of a variety of shapes, including spheres, rectangular blocks, conical or frusto-conical shapes, and the like. Not all of the plugs need to have the same size, shape, orientation and/or symmetry. As further illustrated in FIG. 15, the expandable members 228 may be interconnected by a plug suture or tether 232. The plug tether 232 may form a loop structure 234 at one end of the plurality of expandable member 228 that may facilitate delivery of the expandable members 228 along at least one of the tethers 226. The expandable members 228 may be slidably attached or fixedly attached o the plug tether 232 by a resistance interfit, but in other examples, one or more expandable members 228 may have an enlarged tether lumen to facilitate sliding or other relative movement with respect to the plug tether 232. In still other examples, one or more expandable members 228 may be glued to the tether, or the plug tether 232 may have a crossover configuration or stitching through the expandable member to resist relative movement or separation of the expandable member. For example, in some, all or at least the distalmost or free-floating expandable member, the plug tether 232 may be fixedly attached using any of a variety of attachment interfaces described above. In some further examples, the plug tether 232 may further comprise knots or other fixedly attached structures along its length to limit sliding or movement of an expandable member to a particular range.

The size and shape of the restraining structure 230 may be different depending upon the particular fistula being treated, but in some examples, the restraining structure 230 may have a diameter or maximum transverse dimension that is at least the same as the body 220, but in further examples, the diameter or maximum transverse dimension may be at least two times, three times, or four times or greater than the corresponding dimension of the sealing body 202. The restraining structure 230 may also comprise one or more securing apertures 236 that may permit the attachment of the restraining structure 230 to the skin or a bandage surrounding the dermal fistula opening. These securing apertures 236 may be spaced around the periphery of the restraining structure 230, closer to the outer edge rather than the center of the restraining structure 230. In other examples, the restraining structure 230 may comprise an adhesive surface that contacts the skin surrounding the fistula and resists movement. The tethers 224 and 226 of the device 200 may be secured to the restraining structure 230 by any of a variety of mechanisms, including a clamping structure, adhesive, or by a deformable slit 238 that provides a releasable friction fit interface for the tethers 224 and 226. The attachment site of the tethers 224 and 226 on the restraining structure 230 may further comprise access openings 240 may be used to infuse therapeutic agents into the fistula, and/or to permit passive or active fistula drainage, or the application of negative pressure therapy to the fistula. FIG. 16A depicts the restraining structure 230 without the attached tethers.

Referring to FIG. 16B, positioning of the sealing body 202 and tethers 224 and 226 may be performed using a delivery instrument 250 that comprises an elongate tubular element 252 that is configured with a distal end 254 that releasably attaches to the attachment structure 220 of the sealing body 202. The interface between the attachment structure 220 and the tubular element 252 may comprise a resistance interfit, but may alternatively comprise a mechanical interlocking fit such as a helical threaded interface, for example. In some variations, attachment of the sealing body 202 to the tubular element 252 may also be provided by tensioning the tether 224 that passes through the tubular element 252 and other portions of the delivery instrument 250. To prepare the sealing body 202 for delivery, the sealing body 202 may be collapsed or compressed around the distal end 254 of the tubular element 252 and held in that configuration using a cannula or introducer. In some examples, applying suction or a vacuum may facilitate collapse of the sealing body 202. Although delivery of the sealing body 202 may be performed through the fistula tract and toward the gastrointestinal site, in other examples, the cannula or introducer may be configured to pierce tissue so that delivery instrument 250 may be used to delivery the sealing body 202 and at least one tether 224 along a secondary tract other than the fistula tract. This secondary tract may be a pre-existing tract or a tract formed by the insertion delivery instrument.

As shown in FIG. 16B, other features of the delivery instrument 250 may include one or more connectors 256, 264 that permit the attachment or use of access lines 258 and stopcocks 260, 266, for example, which may facilitate the aspiration or infusion of materials, or the insertion of endoscopic tools or sensors during the delivery procedure. The delivery instrument 250 may include a hemostasis valve 262 or other fluid-sealed interface that permits passage of items such as the tether 224 while resisting fluid leakage.

The expandable members 228 may be provided in a rigid or flexible tubular catheter 270, as depicted in FIG. 16D. To expel or release the expandable members 228, a push element or actuator 272, depicted in FIG. 16C, may be used to serially release the expandable members 228 from the distal end 278 of the catheter 270. This may be performed by pushing the distal tip 274 of the actuator 272 through the proximal end 276 of the catheter 270 while holding the catheter 270 in place, or by holding the actuator 272 in place while withdrawing the catheter 270, for example.

To perform the procedure described above, a kit may be provided that contains the delivery instrument 250 along with the sealing body 202 and attached tethers 224 and 226. The sealing body 202 and attached tethers 224 and 226 may be coupled to the instrument 250 at the point-of-manufacture or at the point-of-use, and therefore may be provided in the kit either pre-attached or separate from the instrument 250. The kit may also comprise an actuator pre-filled catheter 270 with one or more expandable members 228 that are pre-attached with a plug tether 230. Additional catheters 270 with expandable members 228 may be also be packaged and provided separately. In further examples, the kit may also contain one or more other items, including but not limited to a guidewire (e.g. 0.038" guidewire), a peel-away sheath (e.g. 7F, 8F, 9F, 10F, or 12F sheath), one or more syringes (e.g. 0.5 cc, 1 cc, 5 cc, and/or 10 cc syringes), saline or biocompatible fluid, contrast media, a scalpel, one or more free needles, and non-resorbable sutures (e.g. 3-0 or 4-0 nylon suture) that may be used to attach the restraining structure 230 to the adjacent skin or to a bandage. A fistula tract dilator may also be provided in the kit.

In one exemplary delivery procedure, the fistula tract and surrounding area may be prepped and draped in the usual sterile fashion. Anesthesia may be achieved as needed using topical and/or injectable anesthetics. The fistula tract is then irrigated with sterile saline, hydrogen peroxide or other biocompatible irrigation fluid. In some further examples, portions of the fistula tract may be de-epithelialized using silver nitrate sticks, cautery and/or mechanical debridement using a scalpel, for example. The delivery instrument is removed from its aseptic packaging and placed onto a sterile field. To reduce the risk of dislodging the sealing body 202, tensioning of the attached sutures 224 and 226 may or may not contraindicated. Various extension tubes and stopcocks, if any, may be attached to the delivery instrument 250 at this time. Flushing, patency/leakage testing of the delivery instrument connections may be performed using saline or similar fluid. The integrity of the sealing body 202 may also be assessed using saline, contrast agent or a mixture of both and the application of positive and/or negative fluid pressure through the delivery instrument 250. Prior to delivery, the sealing body 202 is evacuated with negative pressure to collapse the sealing body 202. The same or a separate syringe of saline, contrast agent or combined fluid may be prepared as an inflation syringe for the sealing body.

The fistula tract may be traversed using a guidewire, with or without the assistance of imaging modalities such as plain X-ray, fluoroscopy, CT scanning, endoscopy, or ultrasound, for example. The peel-away sheath may be passed over the guidewire and through the dermal ostium of the fistula tract. A dilator may be used as needed to prepare the fistula tract for passage of the delivery instrument and/or endoscopic instrument. The position of the sheath may be verified with the same or different imaging modality. The procedure may be continued once the desired sheath tip location is achieved or verified, e.g. the distal tip is located beyond the intestinal or central ostium of the fistula tract. The guidewire (and dilator, if any) are then removed. The sheath may be flushed with sterile saline. The collapsed sealing body 202 is wrapped around the distal end of the delivery instrument 250 by rolling, rather than collapsing the sealing body 202 like an umbrella. The delivery instrument 250 is inserted into the sheath and advanced until the sealing body 202 is located beyond the distal tip of the sheath. The relative location of the delivery instrument 250 may be evaluated by imaging, by the distance between proximal ends of the sheath and delivery instrument, and/or by the loss of insertion resistance that may be tactilely felt once the sealing body 202 has exited the sheath. A 10 cc syringe, for example, may be attached to the delivery instrument and negative pressure may be applied to the sealing body 202 through one of the stopcocks, which then may be closed to maintain the sealing body 202 in a collapsed state. The syringe may then be removed and is replaced with a syringe of the same or smaller size. The stopcock is re-opened and the evacuation of the sealing body 202 may be confirmed pulling back on the syringe and assessing plunger displacement. A portion of the fluid in the syringe (e.g. 0.5 cc) may then be injected into the sealing body 202 to inflate it. The stopcock may be closed to maintain the inflation.

While maintaining the position of the delivery catheter (or the Touhy Borst valve), gentle traction may be applied to the tension tether attached to the sealing body 202 to fully seat the sealing body 202 to the delivery instrument 250. The Touhy Borst valve may then be loosened and the sheath may be partially retracted into the fistula tract, e.g. proximal to the central ostium. The sealing body 202 may then be deployed by disengaging or otherwise separating the lock mechanism between the Touhy Borst valve 262 and the connector 256. The remaining distal portions of the delivery instrument 250 may then be slowly withdrawn from the fistula tract. While maintaining slight tension on the tension tether 224 to hold the sealing body 202 against the central ostium of the fistula tract, the sheath may be slid proximal the desired length that is to be filled with the expandable members. Slight tension may be maintained on the tension tether 224 through the remaining procedure until the tether is anchored to the skin.

Insert the actuator 272 into the plug delivery catheter 270 until the suture loop 234 just exits the distal end 278 of the catheter 270. The actuator 272 is then withdrawn. While maintaining slight tension on the tension tether 224, thread the delivery tether 226 through the loop 234 at the distal end 278 of the delivery catheter 270. The catheter 270 is then advanced over the delivery tether 226 until the catheter tip 278 is located at the desired delivery location. The actuator 272 is reinserted into the catheter 270 until the distal end 274 of the actuator 272 contact the most proximal expandable member 238 in the catheter 270. The position of the actuator 272 is then maintained while the delivery catheter 270 is retracted to deploy the distalmost expandable member 238. The catheter 270 may or may not be relocated to deploy the remaining expandable members 238. Once deployment of all the expandable members 238 is completed, the Luer fittings on the proximal end 276 of the delivery catheter 270 and actuator 272 may be engaged and the catheter 270 and actuator 272 may be removed from the sheath. Saline may be optionally infused through the sheath to facilitate expansion of the expandable members 238. Using separately supplied catheters 270 and actuators 272, additional expandable members may be deployed using the above procedure to fill the fistula to the desired level. Sealing body 202 placement may be reconfirmed by imaging techniques to ensure that the sealing body 202 is located against the central ostium.

While maintaining tension on the tension tether 224, separate the restraining structure 230 from the sheath and remove the sheath from the fistula tract. While continuing to maintain slight tension on the tension tether 224 through the restraining structure 230, the delivery tether 226 may be sutured or otherwise attached to the surrounding tissue using a free needle passed through the restraining structure and tied to the tissue with the desired tension. At a location opposing the delivery tether 226 on the restraining structure 230, a free needle may be used pass through the restraining structure 230 and to suture the tension tether 224 to the surround tissue. Additional sutures, e.g. 3-0 or 4-0 nylon, may be used to further secure the restraining structure 230 to the surrounding superficial tissue as needed. Final imaging confirmation of the sealing body 202 placement along the central ostium may be performed at this point using the imaging modalities as previously described, but also including double-contrast x-ray studies and colonoscopy/enteroscopy. An absorbent dressing may be securely on top of the restraining structure 230 to absorb any excess drainage that may occur. Alternatively active drainage of the fistula/wound may be performed using wound drainage products or negative pressure wound therapy products. Prophylactic antibiotics may be optionally provided post-procedure.

While preferred embodiments of the present invention have been shown and described herein, it will be obvious to those skilled in the art that those examples are brought by way of example only. Numerous changes, variations, and substitutions will now occur to those skilled in the art without departing from the invention. It should be understood that various alternatives to the embodiments of the invention described herein may be employed in practicing the invention. It is intended that the following claims define the scope of the invention and that the methods and structures within the scope of these claims will be covered thereby.

What is claimed is:

1. A non-vascular fistula treatment kit, comprising:
   a collapsible member comprising a tether attachment structure, and wherein the collapsible member is configured for positioning within a body lumen;
   at least one tether attached to the collapsible member;
   a proximal anchor comprising a tissue contact surface and configured to be coupled and to maintain tension in the at least one tether;
   a bioresorbable material configured for placement in a non-vascular fistula tract; and
   a coupling member attached to the bioresorbable material, wherein the coupling member is configured to attach to the at least one tether at a location adjacent to the bioresorbable material such that the bioresorbable material may be positioned off-axis from the at least one tether, and wherein the bioresorbable material is not directly attached to the collapsible member.

2. The kit of claim 1, further comprising a delivery tool with an aspiration channel, wherein the delivery tool is configured for detachable coupling to the collapsible member.

3. The kit of claim 2, further comprising a delivery cannula configured to permit insertion of the delivery tool.

4. The kit of claim 1, wherein the bioresorbable material comprises a plurality of foam members, each foam member comprising a first end, a second end, and a body therebetween.

5. The kit of claim 4, wherein each foam member is an elongate foam member.

6. The kit of claim 5, wherein the coupling member comprises a looped end structure.

7. The kit of claim 1, wherein the bioresorbable material comprises a porosity of at least 90%.

8. The kit of claim 7, wherein the bioresorbable material comprises a cross-linking agent.

9. The kit of claim 1, wherein the collapsible member comprises:
   a first circular member comprising a suture attachment structure configured for attachment to the at least one tether; and
   a second circular member, wherein an outer perimeter of the second circular member is larger than an outer perimeter of the first circular member, wherein the second circular member is configured to couple to a surface of the body lumen at a distal opening of the fistula, and wherein the second circular member is configured to occlude the fistula at the distal opening.

10. The kit of claim 1, wherein the collapsible member is non-resorbable.

11. A non-vascular fistula treatment kit, comprising:
    an expandable member configured for delivery into an intestinal lumen and comprising a tether attachment structure and an arcuate member;
    at least one tether attached to the expandable member;
    a proximal anchor comprising a tissue contact surface and configured to be coupled and to maintain tension in the at least one tether;
    a plurality of resorbable members;
    and a coupling member attached to at least one of the plurality of resorbable members, wherein the coupling member is configured to attach to the at least one tether at a location adjacent to the plurality of resorbable members such that the plurality of resorbable members are positioned off-axis from the at least one tether, and wherein the plurality of resorbable members do not directly attach to the expandable member.

12. The kit of claim 11, wherein the expandable member has a disc-shaped face.

13. The kit of claim 11, further comprising a delivery catheter releasably attachable to the expandable member.

14. The kit of claim 11, wherein the plurality of resorbable members are located in a cannula.

15. The kit of claim 14, further comprising a cannula push member configured for insertion into the cannula.

16. The kit of claim 14, wherein the plurality of resorbable members are serially attached.

17. The kit of claim 14, wherein the coupling member is a loop structure.

18. The kit of claim 11, wherein the plurality of resorbable members are constructed of a material comprising a porosity of at least 90%.

19. The kit of claim 18, wherein the plurality of resorbable members comprise a cross-linking agent.

20. The kit of claim 11, wherein the arcuate member comprises:
- a first circular member comprising the tether attachment structure; and
- a second circular member, wherein an outer perimeter of the second circular member is larger than an outer perimeter of the first circular member, wherein the second circular member is configured to couple to a surface of the intestinal lumen at a distal opening of the fistula, and wherein the second circular member is configured to occlude the fistula at the distal opening.

21. The kit of claim 11, wherein the expandable member is non-resorbable.

* * * * *